US005753431A

United States Patent [19]

Chiang

[11] Patent Number: 5,753,431
[45] Date of Patent: *May 19, 1998

[54] CHOLESTEROL 7 α-HYDROXDYLASE GENE REGULATORY ELEMENTS AND TRANSCRIPTION FACTORS

[75] Inventor: John Young Ling Chiang, Stow, Ohio

[73] Assignee: Northeastern Ohio University, Rootstown, Ohio

[*] Notice: The term of this patent shall not extend beyond the expiration date of Pat. No. 5,558,999.

[21] Appl. No.: 187,453

[22] Filed: Jan. 28, 1994

Related U.S. Application Data

[63] Continuation-in-part of Ser. No. 135,511, Oct. 13, 1993, Pat. No. 5,558,999, Ser. No. 135,488, Oct. 13, 1993, abandoned, and Ser. No. 135,510, Oct. 13, 1993, Pat. No. 5,420,028.

[51] Int. Cl.$^6$ .............. C12Q 1/68; C12N 5/10; C12N 15/11; C12N 15/85
[52] U.S. Cl. .......... 435/6; 435/172.3; 435/240.2; 435/320.1; 536/24.1
[58] Field of Search ............. 435/172.3, 6, 240.2, 435/320.1; 536/24.1

[56] References Cited

U.S. PATENT DOCUMENTS 5,420,028   5/1995   Chiang ................................. 435/189
5,558,999   9/1996   Chiang ................................. 435/6

FOREIGN PATENT DOCUMENTS

92/13063   8/1992   WIPO .............................. C12P 21/00

OTHER PUBLICATIONS

Ness et al. "Effect of Thyroid Hormone on Hepatic Cholesterol 7αHydroxylase, LDL Receptor, HMG–CoA Reductase, Farnesyl Pyrophosphate Synthetase and Apolipoprotein A–I mRNA Levels in Hypophysectomized Rats", Biochem. and Biophys. Res. Comm., 172(3):1150–1156, (1990).

Lusis, Aldons J., "The Mouse Model for Atherosclerosis", TCM 3(4): 1335–143 (1993).

Dueland, Svein et. al., "Effect of Dietary Cholesterol and Taurocholate on Cholesterol 7α–hydroxylase and Hepatic LDL Receptors in Inbred Mice", Journal of Lipid Research 34: 923–931 (1993).

Dueland, Svein et. al., "Expression of 7α–Hydroxylase in Non–hepatic Cell Results in Liver Phenotypic Resistance of the Low Density Lipoprotein Receptor to Cholesterol Repression", Journal of Biological Chemistry 267(32): 22695–22698 (1992).

Karam et al. "Polymorphisms of Human Cholesterol 7α–Hydroxylase", Biochem. and Biophys. Res. Comm. 185(2): 588–595 (1992).

Breslow et al. "Transgenic Mouse Models of Lipoprotein Metabolism and Atherosclerosis", Proc. Natl. Acad. Sci. USA 90: 8314–8318 (1993).

Cohen et al. "Cloning of the Human Cholesterol 7αHydroxylase Gene (CYP7) and Localization to Chromosome 8q11–812", Genomics 14: 153–161 (1992).

Nishimoto et al. "Structure of the Gene Encoding Human Liver Cholesterol 7α–Hydroxylase", Biochimica. et Biophysica. Acta. 1172: 147–150 (1992).

Thompson et al. "Cholesterol 7α–Hydroxylase Promoter Separated from Cyclophilin Pseudogene By Alu Sequence", Biochimica et Biophysica Acta 1168: 239–242 (1993).

Li et al. "The Expression of a Catalytically Active Cholesterol 7α–Hydroxylase Cytochrome P450 in Escherichia coli", The Journal of Biological Chemistry 266(29): 19186–19191 (1991).

Molowa et al. "Transcriptional Regulation of the Human Cholesterol 7α–Hydroxylase Gene", Biochemistry 31: 2539–2544 (1992).

Nishimoto et al. "Structural Analysis of the Gene Encoding Rat Cholesterol α–Hydroxylase, The Key Enzyme for Bile . . . ", The Journal of Biological Chemistry 266(10): 6467–6471 (1991).

Jelinek et al. "Structure of the Rat Gene Encoding Cholesterol 7α–Hydroxylase", Biochemistry 29(34): 7781–7785 (1990).

Chiang et al. "Cloning and 5'–Flanking Sequence of a Rat Cholesterol 7α–Hydroxylase", Biochimica et Biophysica Acta 1132: 337–339 (1992).

Crestani et al. "Genomic Cloning, Sequencing, and Analysis of the Hamster Cholesterol 7α–Hydroxylase Gene (CYP7)$^1$", Archives of Biochem. and Biophy., 306(2): 451–460 (1993).

Ausubel et al. (1992), Short Protocols in Molecular Biology, Second Edition, (John Wiley & Sons, New York), pp. 9–17 to 9–23.

Lai et. al. (1991) TIBS 16, 427–430.

Sambrook et al. (1989) "Molecular Cloning: A Laboratory Manual, Second Ed." pp. 15.3–15.4, 15.14–15.19, 15.32–15.36, 15.51–15.52 CHS Press N.Y.

Wasylyk (1988) Biochem. Biophys. ACTA 951, 17–35.

Hylemon et al. (1992) J. Biol. Chem. 267(24), 16866–16871.

Pandak et al. (1991) J. Biol. Chem. 266(6), 3416–3412.

Pandak et. al. (1992) J. Lipid Res. 33, 659–668.

Crestani et al. (1992) FASEB J 6(4) A2626.

Primary Examiner—Nancy Degen
Attorney, Agent, or Firm—Foley & Lardner

[57] ABSTRACT

DNA regulatory elements that control cholesterol 7α-hydroxylase expression are disclosed, including bile acid responsive elements. A gene construct comprising at least one CYP7 regulatory element and a reporter gene is used to transfect HepG2 cells. Confluent transfected HepG2 cells are employed in an assay to detect a compound that modulates cholesterol 7α-hydroxylase enzyme regulation. A method for screening compounds that inhibit or stimulate expression of the enzyme is provided, as well as a method for detecting and isolating transcription factors of the cholesterol 7α-hydroxylase gene. A transcription factor of 57 KDa is identified which is useful in an assay for determining regulation of CYP7 expression.

26 Claims, 33 Drawing Sheets

FIG. 4

```
                                    GRE                            LFAI  HRE
RAT     -191 -----GAGTATTGCAGCTCTCTGT TGTTCT GGAGCCTCTTCTGAGAC-TA TGGACTTAGTT
             **************************      ************* *** **      *********
HAMSTER -252 TATCAAGTATTGAAGCTCTCTGCTGTTT *  GGAGCCTCTTCTGATAC-TA TGGACTTAGTT
             ****** ************ ** ***** *   ****** **  ** * *    *  *********
HUMAN   -187 ------GTATTGCAGGTCTCTGATTGCTT GGAACCACTTC TGATACCTG TGGACTTAGTT
                                                   PPRE/HRE
        -135 CAAGCCCGGGTAATGCTATT TTTTCTTCTTTTT-**  TCTAGTAGGAGGACA AATAG----
             *  ****    ***** ***      *        *    *************
        -192 CAAGGCTGGGCAATACTA---TTTTT-TTCTTTT  TT CTAATAGGAGGACA AATAG-TTAGT
             *  ****   * *  ** *   ****  *        *  ******** ****
        -132 CAAGGCCAGTTACTACCAC---TTTT----TTTT TTCTAATAGAATGAACAAATGCTAAT
             TGT3         HRE                     LFBI CAAT BOX                  TATA BOX
        -81  TGTTTGCT TTGGTCACTC-AAGTTCAA GTTTATT GGATCATGGTCCT--GTGCACA TATAAA -
             ****** *   * *** ** ******** ** **** *************       *** ****** *
        -136 TGTTTGCT TTGGTCA-TCCAAGTTCAA GTTTATT GGATCATGGTCCTATGT--**    TATAAAG
             ******* *  * * *  ********** ** **** ********** * * *        ******
        -78  TGTTTGCTTTG-TCAA-CCAAGTCAA GTTAATG GATC-TGGTACTATGT----- ATATAAAA

-23  -GTCTAGTCAGACCCCACTGTTTC-GGGACAGCCTTGCTTT-GCTAGGCAAAGAGTCTCCCCT-
             *************** ** *     **  ******** ***   *** ** **********  **
        -79  AGTCTAGTTTGAGCC-*--TTTCAGGGGCAGCCTTGCT-*G-GCTAAGCACAGACTCTCCTCT-
                **  *******    *                   *
        -23  AGCCTAGTTGAGTCTCT--TTTCAGTGGCATCCTTCCCCTTT-CTAATCAGAGA-TTTCTTCC

37   TTGGAAATTTTCCTG-----CTTTTGCAAAATG
             * ***********        *******  *****
        -23  TGGGAG*TTTTCCTG---CTTT-GCAAAATG
                *  *********      ***  *********
        38   TCAGAGATTTTGGCCTAGA-TTT-GCAAAATG
```

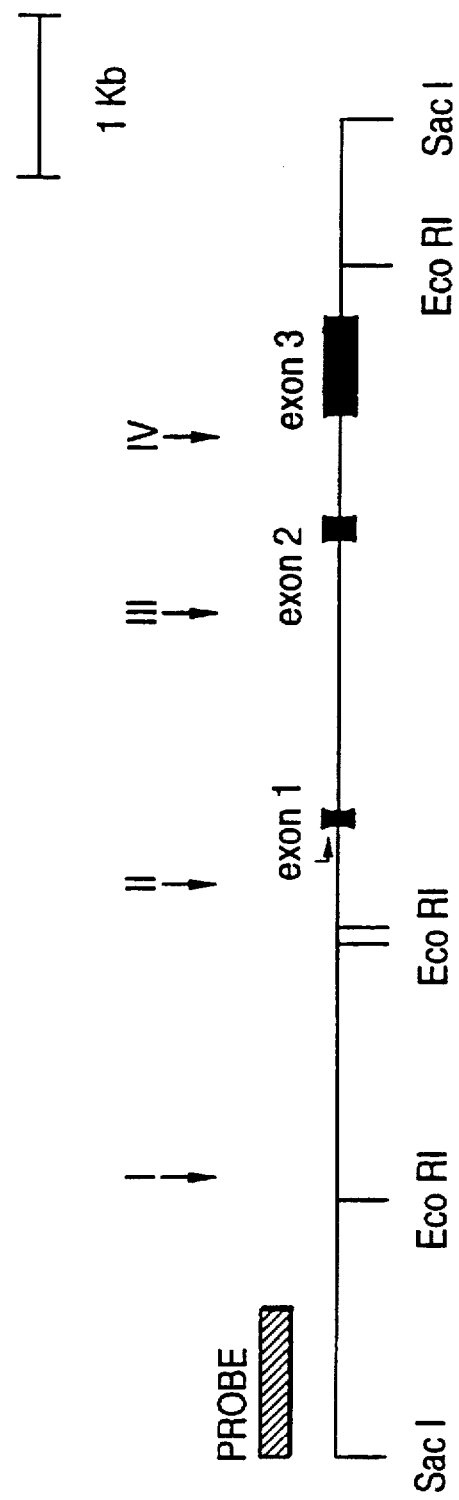
FIG. 5
FIG. 6

FIG. 7A

MOLECULAR-WEIGHT 57658     #LENGTH 505

```
  1 MMTTSLIWGIAIAACCCLWLILGIRRRQTG
 31 EPPLENGLIPYLGCALQFGANPLEFLRANQ
 61 RKHGHVFTCKLMGKYVHFITNPLSYHKVLC
 91 HGKYFDWKKFHFATSAKAFGHRSIDPMDGN
121 TTENINDTFIKTLQGHALNSLTESMMENLQ
151 RIMRPPVSSNSKTAAWVTEGMYSFCYRVMF
181 EAGYLTIFGRDLTRRDTQKAHILNNLDNFK
211 QFDKVFPALVAGLPIHMFRTAHNAREKLAE
241 SLRHENLQKRESISELISLRMFLNDTLSTF
271 DDLEKAKTHLVVLWASQANTIPATFWSLFQ
301 MIRNPEAMKAATEEVKRTLENAGQKVSLEG
331 NPICLSQAELNDLPVLDSIKESLRLSSAS
361 LNIRTAKEDFTLHLEDGSYNIRKDDIIALY
391 PQLMHLDPEIYPDPLTFKYDRYLDENGKTK
421 TTFYCNGLRKLKYYYMPFGSGATICPGRLFA
451 IHEIKQFLILMLSYFELEIEGQAKCPPLD
481 QSRAGLGILPPLNDIEFKYKFKHL*
```

FIG. 7B

MOLECULAR-WEIGHT 56880     #LENGTH 504

```
  1 MMTISLIWGIAVLVSCCIWFIVGIRRRKAG
 31 EPPLENGLIPYLGCALKFGSNPLEFLRANQ
 61 RKHGHVFTCKLMGKYVHFITNSLSYHKVLC
 91 HGKYFDWKKFHYTTSAKAEGHRSIDPNDGN
121 TTENINNTFTKTLQGDALCSLSEAMMQNLQ
151 SVMRPPGLPKSKSNAWVTEGMYAFCYRVMF
181 EAGYLTLFGRDISKTDTQKALILNNLDNFK
211 QFDQVFPALVAGLPIHLEKTAHKAREKLAE
241 GLKHKNLCVRDQVSELIRLRMFLNDTLSTF
271 DDMEKAKTHLAILWASQANTIPATFWSLFQ
301 MIRSPEAMKAASEEVSGALQSAGQELSSGG
331 SAIYLDQVQLNDLPVLDSIIKEALRLSSAS
361 LNIRTAKEDFTLHLEDGSYNIRKDDMIALY
391 PQLMHLDPEIYPDPLTFKYDRYLDESGKAK
421 TTFYSNGNKLKCFYMPFGSGATICPGRLFA
451 VQEIKQFLILMLSCFELEFVESQVKCPPLD
481 QSRAGLGILPPLHDIEFKYKLKH*
```

FIG. 7C

MOLECULAR-WEIGHT 57444    #LENGTH 505

```
  1 MMTISLIWGIAMVCCCIWVIFDRRRKAG
 31 EPPLENGLIPYLGCALKFGSNPLEFLRANQ
 61 RKHGHVFTCKLMGKYVHFITNSLSYHKVLC
 91 HGKYFDWKKFHYTTSAKAFGHRSIDPNDGN
121 TTENINNTFTKTLQGDALHSLSEAMMQNLQ
151 FVLRPPDLPKSKSDAWVTEGMYAFCYRVMF
181 EAGYLTLFGRDTSKPDTQRVLILNNLNSFK
211 QFDQVFPALVAGLPIHLFKAAHKAREQLAE
241 GLKHENLSVRDQVSELIRLRMFLNDTLSTF
271 DDMEKAKTHLAILWASQANTIPATFWSLFQ
301 MIRSPDALRAASEEVNGALQSAGQKLSSEG
331 NAIYLDQIQLNNLPVLDSIIKEALRLSSAS
361 LNIRTAKEDFTLHLEDGSYNIRKDDIIALY
391 PQLMHLDPAIYPDPLTFKYDRYLDENKKAK
421 TSFYSNGNKLKYFYMPFGSGATICPGRLFA
451 VQEIKQFLILMLSYFELELVESHVKCPPLD
481 QSRAGLGILPPLNDIEFKYKLKHL*
```

FIG. 8(A)

|  10        |  20        |  30        |  40        |  50        |      |
|------------|------------|------------|------------|------------|------|
| 1234567890 | 1234567890 | 1234567890 | 1234567890 | 1234567890 |      |
| GAGCTCTACC | CTTGCTCTGC | TATTGTACTT | TTTAATACAC | AGTTCAATCA | 50   |
| AATGTGCCAC | CAGAATATGC | ATGCTAACAG | CTGTAGTGGT | TGATTTTTCT | 100  |
| TTCTACTCTT | CTGTGTGTAA | GACCCCATGT | TTTATCAATT | ATTTTTTAAT | 150  |
| GATTTCTTTC | TTCATGCATA | TGTGTGGTTG | TCAGTGTGAG | TCTGTGTGTA | 200  |
| CAGCAGGTGC | ACAGGTATCC | ACAGAGGCCA | GAGGTTCCCT | GTAACTAGAA | 250  |
| TTACAGGCAC | TTGTGAACTT | TCCTGTATGG | GTGCTGGGAA | GCAATCTGAG | 300  |
| GTCTTCTGCA | AGGGATCTTA | ACCACTGACT | TTCTAGCCTG | CTTTGCCCAT | 350  |
| TTCTATTTAT | GATGACTGGA | AACTGGGCTT | AGGCCTTATA | TTCTCTGAGG | 400  |
| CCAAAATCAA | GTTCTTCCAA | ACTGCAGGAT | TTATGGTCTT | CTATAGTATC | 450  |
| CCACAGAAAT | GGAAAGAAA  | GTGACCCATT | AGAGCAGTAT | TAGAGTCGAA | 500  |
| ATAAACTCAA | CTTGGTATGC | CAGGACTTTG | GACAATAATA | ACCCTGTCTT | 550  |
| TTCAGGGCAT | CTATCTGTAC | TGCTGCAATA | GAAACTCCAC | AGGTCAGGGT | 600  |
| CACAGCTGTT | GTGTTTTACA | CAGTGTCCCC | AGGATTAGTT | CAGTGCCCAC | 650  |
| CATGCAATAG | GTGTCATGGT | GTGTGTGT   | GTGTGTGC   | GTGTGTCGTG | 700  |
| CTTGTGTGCA | TGTGTGTGAG | ACACACACAC | AGAGAGATAC | AAAGACAGAA | 750  |
| ACAGAAAATT | AATAAAATTT | TACCAACTAA | AATAGGGAAT | TAAAGAAAAG | 800  |
| GAGGAGAAAA | AGTTGGGCAT | TCAACACCAT | AAAGTCCAG  | TACTATGCTA | 850  |
| AGAACACCCA | GCTGTCCTCA | CACCCGGGCA | TGAAACTTCA | TGCACTGTTC | 900  |
| ATCAGAAAAT | CGTTACACA  | CATCCCCTTG | CAGTCTACTT | GTAGTTTTAA | 950  |
| CAACTTCAGA | GAGCACTAGC | ATTTCCAGCC | CCAGGTTAGA | AGCTTTGGTA | 1000 |
| GATGCTGTTT | GCGAGCACAG | GATAGCAGCA | AGAAGTGGAC | TTGTTAGAAG | 1050 |
| GAAAGCCAAT | GCCTATGTAA | CAACGAAAAC | TAAGTATGAA | TCTCGAATCT | 1100 |
| CCACTCTCGT | GTGTCTGTGT | CTCCATATAC | GTGCTTGGGT | GCCTGACATG | 1150 |
| GCAAGGTGTT | ACAAGTAAGG | GAGGAACAAG | AAAAGGACAG | GGTAGTGGAC | 1200 |
| ATCAGGATGA | ATGCCAGCCA | GGGCGACTGG | AGAGAGTCTA | CGCTGCTCTG | 1250 |
| AAGGTGGGTG | AAGAAGACCT | CAGGAAGCTT | TCTGAGGCTC | CGAGAGTGCT | 1300 |
| TTTCCCTTCC | CATGTTGAAA | CATCCTTATT | TGCAGAGAAT | TCCAGGTTCA | 1350 |
| TGGGAATTTG | TAAAGAGAAT | ACTAAGAGGC | CACCTGTGGC | TTCTCCTATT | 1400 |
| TTTGTCTGCT | GTCATTTATG | GGACAGGGTT | AGAGACCTGG | CTTGCTTGGC | 1450 |
| TATGAGGCTG | TTGCTTCCTC | GGTTACTCTG | CTGTGGTTGG | ATGCATTAGG | 1500 |
| GTTAGGCCCC | TCAAGAGCCA | TGTGTCATTT | TATAAAAGCA | ATATAAATAT | 1550 |
| ACTTAAGGTG | CACAAACCAT | TAGGAGGTCT | GAGATAATAG | ATTCTGAGAA | 1600 |
| AATCTATCCT | GCTGTGTAGC | AACTGATGTT | TATGATTATA | GTCCCAGACC | 1650 |

FIG. 8(B)

```
          10         20         30         40         50
    1234567890 1234567890 1234567890 1234567890 1234567890
    ACACGATAAA GGATCTGTGG ACTCTGTTTA GGGAGGTCAA AAAACTATTG   1700
    CAAATGGAGT CTATAGAGAA AACTAGACAG GACTCAATGC TCACCAATCG   1750
    AGAATTAGTT GATGAGCTGG GGTAGTGACT TAGTGGATAA GAACACGGTC   1800
    CTTTCAGAGG TCCTGAGTTA AATCCCCAGC AAACACATGG TGGCTCATAA   1850
    CCATCTATAT TGTGATTTGA TGCCCTCTTC TGGCATGCAG GTGTACATGC   1900
    AGACTCGTAT ACATAAAATA AATAAATCTT GAAAAAATGA ATACGTTGAA   1950
    TAAGTGTCCC CTCGGATAAC TTTCTGCAGA ATTTTAAGCA CATGTCAATG   2000
    GTAATAACAC ACACACAC ACACACAC ACACACAC ACACATAC            2050
    ACACACCATA CAGATATGTA TCTAGAGACA TACACATGTA CATTTTATCT   2100
    CTTTTATTTT CTTCTCCCCT CTTTGACATC AAGGAATAGA ATGCACTCAC   2150
    TGTGGCCTAG TGCCACACTC TACCTATTTC TTTGGCTTTA CTTTGTGCTA   2200
    GGTGACCCGA AAGGTTTAAA TATCAAAAAT GCTAATGGCT CGACATTTAC   2250
    ATCCCCAATT TCTCCTTTCT CCTTACCTCA GACTCTTACA TTCAGTTGAC   2300
    AATTTGACAT CGTCTCCTGG ATTTTCAAAT GTTCAGCACA CTGTACTGAT   2350
    GTACTGCCTT CCAAGGCAAC CGGCACGATC CTCTCCCAC TCCCAAGCAT    2400
    CCCTCCATGA GCCAGTGTTT GCTTATCTTC TTGACTCTTG TTTTAACCCA   2450
    ACTCCTCCCC TATTCACTCT GCTCTAATTC ATTCATTCTA TATTTTCGCA   2500
    CATCAGGCTC ATCCTTTGCT CAGGAACTTC ACTTTTGCTT TCCGGTCTCC   2550
    TGGAAATGTG TTTTCTTGGC TATTCCATCT CAAGACCATC TTTTCAGAAA   2600
    AGCTTTTCCT ATCAACATAT TTAAAGCCCT CTTCATCCCC CAGTAGCTCT   2650
    GGACACCTCA TTTTATGGAT ACACAACACA TATTTGCCAC CTGTCTCCCC   2700
    ATTAAAATAT AATCTTCAGT AGAGAAACTC CATATCTTGT TAATACCTGA   2750
    AACAAGAATA TCTTCAAAGA GTTCCTGGGA CATAAAAACG CTCAATTAAT   2800
    ATTTATGTTA AACAGGGATC TGGGGTATAT CACAGAGGTA GAGGGCTTAC   2850
    CTAGGAGGAG TTGGGCCATG GGTTCAACTT CCAGCACAGA ATGAAAGATT   2900
    ATGTTAAATA AAGTTGGGAA GGATGTATGC CAGTCTATGA GTAGTATAGG   2950
    AGGTAAATTA TGAATTCATA TTTACTTTTC GGACAAGAAG TGTTGTAGTC   3000
    TTTATTTGAA ATAAATACA TCTTAATTAC CAATAACAAT TGGTAAGGAG    3050
    TGAATTCTCA AGCTGTGGCT TCCTGGTAGA TGAGTCCTGG GAGGTTTTCT   3100
    ATTTCGATGA TGGTAGATAG GTAACCTGTC ATATACCACA TGAAATACCT   3150
    GTGGCTTTGT AAACACACCG AGCAGTCAAG CAGGAGAATA GTTCCATACA   3200
    GTTCGCGTCC CTTAGGATTG GTTTCGGGAT ACTTCTGGAG GTTCATTTAA   3250
    ATAATTTTCC CCGAAGTACA TTATGGGCAG CCAGTGTTGT GATGGGAAGC   3300
```

FIG. 8(C)

```
          10         20         30         40         50
  1234567890 1234567890 1234567890 1234567890 1234567890
  TTCTGCCTGT TTTGCTTTGC GTCGTGCTCC ACACCTTTGA CAGATGTGCT  3350
  CTCATCTGTT TACTTCTTTT TCTACACACA GAGCACAGCA TTAGCTGCTG  3400
  TCCCGGCTTT GGATGTTATG TCAGCACATG AGGGACAGAC CTTCAGCTTA  3450
  TCGAGTATTG CAGCTCTCTG TTTGTTCTGG AGCCTCTTCT GAGACTATGG  3500
  ACTTAGTTCA AGGCCGGGTA ATGCTATTTT TTTCTTCTTT TTTCTAGTAG  3550
  GAGGACAAAT AGTGTTTGCT TTGGTCACTC AAGTTCAAGT TATTGGATCA  3600
  TGGTCCTGTG CACATATAAA GTCTAGTCAG ACCCACTGTT TCGGGACAGC  3650
  CTTGCTTTGC TAGGCAAAGA GTCTCCCCTT TGGAAATTTT CCTGCTTTTG  3700
  CAAAATGATG ACTATTTCTT TGATTTGGGG AATTGCCGTG TTGGTGAGCT  3750
  GTTGCATATG GTTTATTGTT GGAATAAGGA GAAGGTATGG AAAGATTTTT  3800
  AAAAATTTGT CTTTTAGCTT ATTTCTAGTA TTCATTGCCT TCACTATTAT  3850
  GTAGTGCAAA AAATACTAAT GCATTAATAT TTTTAAATTT AAAATTTAAA  3900
  GACGTACTTC TTTGACTAAA TCTAGTAAGA TGTAGAGAGT CCCCCTTGGA  3950
  ACATTCACAT ATGCCACTGG TAATGCAGAT CTTGTGAAAT ATAACTAAAG  4000
  AAATCACAAG TCATCGATGT AAGTTTGTGT CTGCATGGGC GGAACAAACC  4050
  TAAGCTAAGA AGAGTAGTAT TTGGGAGGGA TCTTTCTGTG ACATGAACTG  4100
  AATAGACGCA CTGCCTCAGC AAACACACAT TCATTTGAAT TTTCCTCAGA  4150
  CTCAGTCTAA GCCTGGTGAG AGCACCAAGT GTGAGTCTGT CTGCCACTAA  4200
  CGTTTCCTTC CAGTGGTAAT CAGCTGTGTG GCTGTGAAAC CTTGGCGCCT  4250
  GCACATGACA GCCATTTGAA TAGTTCAAAG AACATTTAGG GACAGGATAT  4300
  TAAGATATTT TCTGTGATGT CAACATCAAA ATAGGAGAAT GCCCTGGCA   4350
  TTATCTTCAG AGAGGTAGAC TACTGTGCGT TGTCTTACTT TAAAGAAATT  4400
  TCTTTGCCCC TTTGGCTATT TTAATTCAAA CCTGAAAGTT TTCAGTTTTA  4450
  ATTAAACTGT TGATTTTCAT GCTAGGAAAG GAAATATCAA TTATACTTAA  4500
  TTGTTCTTAC AAGAAATAAA ATCATTTATG TCGGAGATA ATAAGCTCA    4550
  TAATTTTAAT AAAACATTTA AGAGAGAGAA AAAGAGTAGT GGATTATAGT  4600
  TCATTGTCTG TCAATGTTTA CCTGACCCAG TTTCATTTTA TAATTATCTA  4650
  ATTTTTCAAA TGAGATTCCT GTTCTTTCCA AATATCATTG CAGAATACTA  4700
  ACATTCTTTT TTTCAGAGTT GAGAATCAAA TGGAGGGTTT TTTCATCCTG  4750
  GCACAAGCTC CGCTCTTCAG TAACACCTCC AGCCCTCAGA ATGCCAATAT  4800
  TTTAAATTAT GTAGGTTGTT AAAACTTTAG TGCTGGGGCT GGGGATTTAG  4850
  CTCAGTGGTA GAGCACTTGC CTAGCAAGCG CAAGGCCCTG GGTTCGGTCC  4900
  CCAGCTCTGA AAAAAGAAA AGAAAAAAA AAAACTTTAG TGCTGTAGCC    4950
```

FIG. 8(D)

```
           10         20         30         40         50
      1234567890 1234567890 1234567890 1234567890 1234567890
      CTTTCTGTTA TTTGATGTTT CACATCTGTT AAAAAACAAA ACAAAACAAA  5000
      AAAAACAAGC AAATGGAACA TTTTAGGCAT TCTTTGGGGG AAATGATTCT  5050
      TAGAGCAAGT CTAATCATTA GGTGATAGTT TCATTTTTAC ACCAAGAACA  5100
      AGAATCTTGT TGGCTGTGTT AACACTTTAA GCCCTGTTGT AGGGAAAAAG  5150
      CAATCAGACA CAGGCACAGA AAAGAATTTG GATGAGTACT TGATGATGTA  5200
      TGTATATATG GTGAATAGAC TGATGGGTGG GCTGCTGGCT GGGTTGGTAA  5250
      GTGGGTAGAT TTTTTTTTAA AGATTTATTC ATTTATTATA TATCAGTACA  5300
      CTGTAGCTAT CTTCAGATAC ACCAGAAGGG CATCGGATCT CTTTACAGAT  5350
      GGTTGTGAGC CACCATGTTT TCCTAACCTC TCAAGTCTCT GTCTTCCAGG  5400
      AAAGCTGGTG AACCTCCTTT GGAGAACGGG TTGATTCCGT ACCTGGGCTG  5450
      TGCTCTGAAA TTTGGATCTA ATCCTCTTGA GTTCCTAAGA GCTAATCAAA  5500
      GGAAGCATGG TCACGTTTTT ACCTGCAAAC TGATGGGGAA ATATGTCCAT  5550
      TTCATCACAA ACTCCCTGTC ATACCACAAA GTCTTATGTC ATGGAAAATA  5600
      TTTTGACTGG AAAAAATTTC ATTACACTAC TTCTGCGAAG GTAATTAATT  5650
      CGTTATACAG ATTCTGTTTG TTTCCTGGTC TGTTGATGTA TTAGTGTATT  5700
      TAGTTGTTCC AATTTTGTTA GGTTGCAGAA TAGAGGTAAC ATAAAATCAG  5750
      GGCGTTTCTT AGTAATAAGC ATTAGACATT TAAGGCAGAT GTAAACCTGT  5800
      CATTGATGAT TCCGGAGACA GAGGACACTG CAGGAATCAG GAAGGTACAG  5850
      ATTCATAGCA CCACTCGTCC CTTAACAACA CCCTGAGCAG GGTGTTGGCA  5900
      CTCTTAGCCT TCAGTCCTTG TACACGCTT TCATTCCTAA GATATAGGCT  5950
      GTATATTTAA ACACGATTTG GAAGCCATCA AGAATCTGTT CTAGAGAAAA  6000
      CAGCATTTAA TGATCTTTTG CAAGAAAATA TCAGTTATAG TCTCTGTCAT  6050
      TAAGTACATT GTAATCTGGT TAAAGAGTAT CTACTAAGAA AGTAAAGGCA  6100
      GATTAGAACA ATACCAATGG ATGATGGGCC ATCCAGAGAA ATCCTACTGT  6150
      AAATGCTGGG ATTTAAACTT GACCCCAAGG AAGAGTATGA CTTGATTCTA  6200
      CCTTTGGAAT GTGCTGTAAA ATCATATTAG GGAAGGTTCC AGACAGAGAA  6250
      GTGGGATGTA TTTAATCTAT CTTCCAGCCC ACTCTCTAAC ACTAGCTAGC  6300
      TTTGGGCTTT AGACCCTCCC CATTTCATGG ATTCTATTTT CTACCACGCA  6350
      TTTGGACACA GAAGCATTGA CCCAAATGAT GGAAATACCA CGGAAAATAT  6400
      AAACAACACT TTTACCAAAA CCCTCCAGGG AGATGCTCTG TGTTCACTTT  6450
      CTGAAGCCAT GATGCAAAAC CTCCAATCTG TCATGAGACC TCCTGGCCTT  6500
      CCTAAATCAA AGAGCAATGC CTGGGTCACG GAAGGGATGT ATGCCTTCTG  6550
      TTACCGAGTG ATGTTTGAAG CCGGCTATCT AACACTGTTT GGCAGAGATA  6600
```

FIG. 8(E)

```
            10         20         30         40         50
   1234567890 1234567890 1234567890 1234567890 1234567890
TTTCAAAGAC AGACACACAA AAAGCACTTA TTCTAAACAA CCTTGACAAC  6650
TTCAAACAAT TTGACCAAGT CTTTCCGGCA CTGGTGGCAG GCCTTCCTAT  6700
TCACTTGTTC AAGACCGCAC ATAAAGCTCG GGAAAAGCTG GCTGAGGGAT  6750
TGAAGCACAA GAACCTGTGT GTGAGGGACC AGGTCTCTGA ACTGATCCGT  6800
CTACGTATGT TTCTCAATGA CACGCTCTCC ACCTTTGACG ACATGGAGAA  6850
GGCCAAGACG CACCTCGCTA TCCTCTGGGC ATCTCAAGCA AACACCATTC  6900
CTGCAACCTT TTGGAGCTTA TTTCAAATGA TCAGGTAACT TTCCAGTGAC  6950
AGAAATTGCA TTTTAAACTC AAAACCCAAA AAGACTTATA GAGCTTTCTG  7000
TGCTATCAAC AAAGAAAGTA ATACTCAATG TCCGTGTTTA GCATGTGCGT  7050
AACAGAAGCA GCAATTTTTA GGTGCACAGT CCCATCGAAA GGGATGTCCC  7100
AGAAGCCACA GAACTCAGAC AGGTTGGTGC TCCATTAGTA CAGGTTCCCT  7150
GGCCTAGTCT TGCTCCCTCA CCGATATGTT CCTCTTAATA TCAAATTAAA  7200
TCCCCGAGTG CAGTCGTCAC CACCATATAA ACATTTGAAA TGATGACTGA  7250
CTTGCAGGTG TGATAAGAGC AGTGACCATA CCTTACTAAT TCACTGGAAT  7300
TCATAGGCAA AGTAACACCA TCGATTTTGT ATTCATATAG GAGCTGCAGC  7350
CATATTTTAA ATAGCACAAC TACTTGTTAG TCAAGCATTC TGAGGCTCAC  7400
TGTAATCAGG TAAAGTAGGT TTAACTCAGC GTCCTACCAG TTCCAGGCAT  7450
TGAAATGGAA TATCCTTTAT CCCACCCATT CAAAACGTAA TATATAAATG  7500
GAAGCACAG TTTTGAAGGC CATGGTATGA TTTAGGGAAT TTACTCTCAT  7550
GGTCCAATCC CTTGTAATTG TATGCTAGGT GACATATCCT TCTGACTTAC  7600
TATGTTCATC GTATATTCAA TCCTTAGTTT ATAGAGACTG ACCAAAGCTC  7650
TGCTTTTGCA TAGCAAAGCT CCTTTTAATG CCCATTCCTA AACTCAAGGA  7700
CACGAATCCA GTTCAGTGCC CTTTTGCATA CTCCCTGGCA GACTCCCGTT  7750
GCCATACATC CTCCCTCGCT CGATTCCCAT GACCTCGCCC TTGCACACCC  7800
TGGTACTAGG ACCTTCCCTG GCGATACTTC CTACTACCTA TGCCACCTCA  7850
TTAAAGGAA GGGATAATTG CTATTTACTT GCAGTTCTCT GAATGAGGAC  7900
ATTTTCCCCA TACGGCTCTT TCCACAGGAG TCCTGAAGCA ATGAAAGCAG  7950
CCTCTGAAGA AGTGAGTGGA GCTTTACAGA GTGCTGGCCA AGAGCTC     7997
```

FIG. 9A

```
   1  TTTTGGTTA  TCTTTTCAGC  CGTGCCCCAC  TCTACTGGTA  CCAGTTTACT  GTATTAGTCG
  61  ATTTCATGC  TGCTGATAAA  GACATACCTG  AAACTGGACA  ATTACAAAA   GAAAGAGGTT
 121  TATTGGACTT  ACAATTCTAC  ATCACTTGGG  AGGCCTCACA  ATCATGATGG  AAGGAGAAAG
 181  GCACATCTCA  CATGGCAGCA  GACAAGAAAA  GAGCTTGTGC  AGGGAAACTC  CTCTTTTTAA
 241  AACCATCAGA  TCTCATGAAA  TTTATTCATT  ATCATGACAA  TAGCACACAGA AAGAACTGCA
 301  CCCATAATTC  AGTCACCTCC  TACCAGGTTC  CTCCCACAAC  ACGTGAGAAT  TCAAGATGAG
 361  ATTTGGATGG  GGACACAGCC  AAACCATGCC  ACACTACCAT  GCCTGACTTC  CTTTCCATTT
 421  TTGTATATTT  GCTTGTTCTT  CATTTGCCCG  AGAAGTAACT  CTAAAGGGCT  GTATTATTTG
 481  GATATTAGAT  TGGCATTTTA  TCTGACTGGG  ATATCTTGCT  GTGATTGTCC  ATGTATAAGA
 541  TCAGCTTTTC  TATAAGCCAT  ATTTTTAAAA  AGATATATTA  ATTTTTAAA   AATCCACCTG
 601  TCTAAATAAA  TGCACAAAGC  CCCCCAAAAA  CCTAGATTCT  AAGAAAAATC  TATGTACTGC
 661  CATACACACT  TTGATATTAA  TATTTATGGT  GATAAATTAC  ACACAAAAAA  TGTGTGATCT
 721  CTGTTTAAAC  AGGCAAAAAC  AAAAAACACA  TGAAATAAAT  CTATGCCATC  TATAGCCAAA
 781  ACTGGAAACA  ACCCACATAT  CCATCAATAG  GAAATCAGTT  AAATAAATTA  TAGTACATTT
 841  ATCCAATGGA  AGATTAAGCA  CATATTCAAT  ATAATTATTT  ATACACACAT  ATAGATACAC
 901  ACATGTATAA  ATATAGAGAA  TACTGTGGGT  GTATGTGTGT  GTGTGTTTAT  ATACATATAT
 961  ATACACACAC  AGTACTGTTG  CCTACCCTCT  TTTGTCTTAA  TTCTGTGAAC  TCTCATTCAC
1021  TCTGCTTCAG  TAGGATACCT  CCTTCTTTTT  GGTTCTTAGA  CTCACCAAGT  TGATCCTTGA
1081  CTCAAGACAT  TGCATTTGCT  CCTTCCTCTT  CCTGGAATAT  CCTTCCTTCT  GATATTCACA
1141  TGAGTAGTCT  CTTCTTGTCA  TTCAGATCTC  AAATGTCACA  ATTCAGAGA   GCCCATCTCT
```

FIG. 9B

```
1201 GATCATCATA TCTAAAGTTG TCCTCATTCC CCCATAGCTT TCTATACCAT GTTTTATTTT
1261 TTTCATAACA TGTATTTTAT TACTCCTTTC TCCATTGGAA TAGAATCTCC ATTAGATTAG
1321 GAAATCTGCC TATCTTATTA ATGCCTGCAA CTGGAATACT TTTGAAGAGT TCTTGGCACG
1381 TAATAAATAC TCAACTAATA TTTTGTGTA CACAGAAATA AAGTTTGGAA GAACAGATGC
1441 CAAATTGTTA CTAGTGGTTA CTTCTGAGTA AAGGAGTAGC ATGGTAGGTA AATTATTAAT
1501 AGATGTTCAC TTTCCACCAA GATATGTTTT AGTTAGTCTT AACTTACTTG AAATGAAATT
1561 TATTACTTTA ATAATTAGAA ACATTGATAA ACATTTTAGT CACAAGAATG ATAGATAAAA
1621 TTTTGATGCT TCCAATAAGT TATATTTATC TAGAGGATGC ACTTATGTAG AATACTCTCT
1681 TGAGGATGTT AGTGAGTAA CATGTTACTA TATGTAGTAA AATATCTATG ATTTTATAAA
1741 AGCACTGAAA CATGAAGCAG CAGAAAATGT TTTCCCAGTT CTCTTCCTC TGAACTTGAT
1801 CACCGTCTCT CTGGCAAAGC ACCTAAATTA ATTCTTCTTT AAAAGTTAAC AAGACCAAAT
1861 TATAAGCTTG ATGAATAACT CATTCTTATC TTTCTTTAAA TGATTATAGT TTATGTATTT
1921 ATTAGCTATG CCCATCTTAA ACAGGTTTAT TGTTCTTTT TACACATACC AAACTCTTAA
1981 TATTAGCTGT TGTCCCCAGG TCCGAATGTT AAGTCAACAT ATATTTGAGA GACCTTCAAC
2041 TTATCAAGTA TTGCAGGTCT CTGATTGCTT TGGAACCACT TCTGATACCT GTGGACTTAG
2101 TTCAAGGCCA GTTACTACCA CTTTTTTTT TCTAATAGAA TGAACAAATG GCTAATTGTT
2161 TGCTTTGTCA ACCAAGCTCA AGTTAATGGA TCTGGATACT ATGTATATAA AAAGCCTAGC
2221 TTGAGTCTCT TTTCAGTGGC ATCCTTCCCT TTCTAATCAG AGATTTTCTT CCTCAGAGAT
2281 TTTGGCCTAG ATTTGCAAAA TGATGACCAC ATCTTTGATT TGGGGGATTG CTATAGCAGC
2341 ATGCTGTTGT CTATGGCTTA TTCTTGGAAT TAGGAGAAGG TAAGTAATGT TTTATCTTTA
```

FIG. 9C

```
2401 AATTGCTCTT TGATTCATCC ATTTAATTTT TTTACCTTCA TTTTTATACA GTAAATTTGG
2461 TTTCTATAC  TTACACATAT TAGCATTATC TTCCTTATGT TTTAAATGAA AAATTTGATT
2521 TGAATTTTA  AAGTAATATC TTTTTACTA  TATCTCACAA GACATATGAC AGCTTCCCTT
2581 TTTAGTATTG GCATATACCG ATGGTAATAT ATAAATGTAT ATTGGTGTTA AACATAACTG
2641 ACAGAAATTG TATAAGGTCT CTATGTACAT TTATATGTGT ATCTAAAGAG GAAGCCCAGA
2701 TTAGTAAGGA TACAAGTAGC AAGTGGGAAT CTACAATGGA AAGGATTGCT TTCTCTCACA
2761 TGGCTTCAAT AGATACTCTT GCTTAAATAA ATGTTCTCTT TTAAGCTCAT TCTGTGCAT
2821 CGCATAGACT CAGCCCTAAGC CTGAACAAGA GCATAGAGCC TGAGCTGATC ATTCTATTAC
2881 TGTTTTAAA  TAAATGTTAA TCAACTGTGG AAGTTTGCTG AGTGTATGTG
2941 ACATCGATTT CATTATTTA  CAACTGGTTC GAAAAACAAA TACAGTCAGA
3001 TCCAGAACCA TAGTTTATTT AACTTCTAAT TGGCTCAAGG AGTAATGTG  GGGAGGCATA
3061 TAGATATTCT CTGCTATGTC AATCTCAAAA AGAGAAAATA ACCCTAACCA TCTTTCAGCT
3121 TTGTAGATTG CTATGTGTTT TCTGCCCTTG CAGTTTCTTT CAGGCCCTGAT AGTTTTTACT
3181 TTTAATTAAA CTACTTATCT TCAAACTAAG AAAAGAAAGG TAATTACTTT ATACTGTATT
3241 ATTCTATCAA GAGGTACAGA AGTTTATGTT GGAAAATAAG TTTACATGTT CTAATAAAAA
3301 CATTTAAAG  GAGCACTGAA TTACAATAGA TGATTCCGTC AGTGTTTATC TTACTCAATT
3361 TCATTTTATA ATAAGCTGAT TTCTCACATG AGATTCTTCT TCTCTGAAAC CATCCTTATA
3421 GAATATAATA TAGATATCTT TAAACTAGGA ATATTTTCAA AACCTCAGTT CTGAAATCCT
```

FIG. 9D

```
3481 CCCTTATTCA GTGATCTGTG TCTTTAAAGA AATAATCAA AAGAAACATT TTGAGATATT
3541 TAGAAAAATG ATGCTTAGCA AAGTGATAAA CACTAGAAATG TAGTTTTGTT TCCGCACTGA
3601 CAACAAGAAT CTTGTTGGTC TTGTAAATCC TTTGCCTGT ATCACTGGGA AAAGTGATGA
3661 GCACATAGTA GACGGGTGCT TGTTGAATGT GTATATGGAC GGATGCATGA ATGGATGGAT
3721 TTAGTAATCC TTTCCACCAA CATATCATGT TACTAGGTTA ATATAACCTA TTACTGTAGT
3781 AAAAGAGCAG GGCCCATCCA ACAAAAGAAA TATCTATAAA CTATAGGGTT TCAAAGTTTG
3841 AAGTCAGTGG GAAAATTTT AAAACCTGAT GTAAGTAAAA ACCCAAAACT GTAATCATCC
3901 ATGTCTATCA TACACTGTGT TCTGACAGGC AAACGGGTGA ACCACCTCTA GAGAATGGAT
3961 TAATTCCATA CCTGGGCTGT GCTCTGCAAT TGGTGTGCCAA TCCTCTTGAG TTCCTCAGAG
4021 CAAATCAAAG GAAACATGGT CATGTTTTTA CCTGCAAACT AATGGGAAAA TATGTCCATT
4081 TCATCACAAA TCCCTTGTCA TACCATAAGG TGTTGTGCCA CGGAAAATAT TTTGATTGGA
4141 AAAATTTCA CTTTGCTACT TCTGCGAAGG TAAGCAGTTT TACATTTATA TACCATTCTG
4201 TTTGTCTTCT ACCTTTTTAT GTGCTTGTCT ATTGAGAAAT TTGATGTAC TTAGATTTTA
4261 TGATAAAGGT GTTGAAGAGA GTTATCCTTA TGTGGAGATT CTTAGAAACA TAAATAAATT
4321 ATACGTAGCT TCTTAGTAAT AATCATTTAG AAAGTCAAAA TAGGTATAGA TTTCCGTCAT
4381 TTGCTTTGCA CGAGCTAGCT AGGGTGAAAT ACAGATTAAA TGCTCTACTG AGACAGGTGG
4441 CACTGTACGA ATAAGATAGA TTAAAATTCA TCACATCAGC AATGTCTATG CAGAGCGAAG
4501 TGACGGAAAC CTAACATTCA GCAGTTGTCT CACCACACTT GTGCCACACA GTGTTTCATT
```

FIG. 9E

```
4561  TTGATAAGGA ATTGGCAAGA TATTTTAACA TCATTTAGAT GTAATAAAAG AAGATCTGTT
4621  ACTGAGAAAA AAAACCAATA ACTACTTACT TACTGCAAAT AAATATTAGC TTTGGTCTTT
4681  GTGACTAAGT AGCTTAAAGT TTGGTTAAAA TACATCTACA GCTGGACACA ATGGAACACA
4741  CCTGTAGTCC CTGCTATTTG AGAGGCTGAG GCAGGAGGAT CGCTTGAGTC CAGGAGTTTG
4801  AGGCTGCAGT GAGCTATCAT TGTGTCACTG CACTCCAGCC TGGGTGACAA TGTGAGACCC
4861  CATCTCTAAA AGAAAAAGAA AAAGAAATCT ACAAATAATA TAAAAGATAA CTAATGATTT
4921  TAAAACATTA TCAATTAGTT TATGTGCAAT AGCTGTAAAT AAGTGCAGTA GCATAAGAAA
4981  TAAGACATAG ATGACTTGAG TGATCCAGGG GAGTGCCACT GAAGTTGGCT TTAAAGGAAA
5041  GGTACAGTTT GGTCATTTAT TTGTAAAGTG CTATGAACTT GTACAAGGA AAGCCAATTT
5101  CCCGTGTTTA CCAAGTAAGG AACTATGAAA GTATCTAATC CGTTTTTCAG TCATTTACTA
5161  TGACTAGGTC AGGTTTAACT TCTTTTTCTG CATGTTTTAT TTGCTATCAG GCATTTGGGC
5221  ACAGAAGCAT TGACCCGATG GATGGAAATA CCACTGAAAA CATAAACGAC ACTTTCATCA
5281  AAACCCTGCA GGGCCATGCC TTGAATTCCC TCACGGAAAG CATGATGGAA AACCTCCAAC
5341  GTATCATGAG ACCTCCAGTC TCCTCTAACT CAAAGACCGC TGCCTGGGTG ACAGAAGGGA
5401  TGTATTCTTT CTGCTACCGA GTGATGTTTG AAGCTGGGTA TTTAACTATC TTTGGCAGAG
5461  ATCTTACAAG GCGGGACACA CAGAAAGCAC ATATTCTAAA CAATCTTGAC AACTTCAAGC
5521  AATTCGACAA AGTCTTT
```

FIG. 10A

```
   1 GAATTCTACT CTTTAAAGGG GTGAATATTA TGGTACTTGA ATTTTATCTC AAGAAAAATG
  61 AATAAAAAGT AACTAAATCA TTGAAAATAT CTGATGGCAT GGGGTTTGTG GGGTAACTGG
 121 CATTCCACAG TGATTTTCAA AGGGCTTGTG CTGTTTTCAT TTTGCTTTGT TTTAGTTATG
 181 GAGCCCTTCC TTGAAACAAA CTTCATACTA CAGTCCTCTT TCATGAAGCA GAAGAGGGCA
 241 GTGGGCAGAG CTCTCCCTTTG GCTTTCTCCC CCACCACAAC AGGGAGCCCT GGAGCTCTAG
 301 GAGAGAAAAT CTGAAATATA AAGGGCATGC ATGTGAGCTG TGGAGTCCCA GAGCCCTGGG
 361 TTTGCATCCT AGATCTGCAA CTCCCGTGAA TTGAGTTTTG GGAAGTTGCT GAAACTCTGA
 421 CCTCCTGTTT TCTCATGGTA TTGTTGTAAG GGTTAAATGA GACAATGTAT GTGAAGACCC
 481 TGGCCCCACA GTAGAGGCTC TGCACACATT TCAGCGATAC TTTCCTCATG TATTTCCAAA
 541 AATGTTTTCT CATTTTCTTA AAATGTCAGA AAGAAGACAA CAGAACTTAC TTGCCTTTTA
 601 CAACAGAACA AATGGAGCAA GTCAGAGGTC AAGGTGCTAA CATTCTTCAT GGTTCCTCAC
 661 CACCTTTGT TCTGTTAGCC TATAGGGAAA AGTCTTCTTT CTCATCTCAT TATCTGCAGG
 721 GGAAAATAGT ACTTCAGCAA GTGATCCAGT CTCCAGGGCC ATTAACATAC CCTCCTAGGA
 781 AGAGGTTTGT TCTACTCTCT CTGTGCTCCA TGTCTAAGAA AAGGTTAATT CCTCAGCCTT CTGTGCTGGC
 841 GCTAGGGAAA GTCAGGAAAG TGAAAATAGT ACCCCAGCTA AAGCCGAAAA ATGAACTGCC CTGTGCTGGC
 901 CTGAGAAGAC AAGACCAGCT TCCTCAATGG CTCAAGATTT GGTTTCCTTC AATATGTCCT
 961 TTTGGAAATA TGTCCATGAC ATCGGAGAGA TAAAAGGAGC CAGGATTGCT CACATTCAGG
1021 AAAAAGCTC CACTATCTT CTCTCTCTCC CTCTTTCTCT CCCTCCCCCT GACTGCCCTC
1081 TTCTCTATCT CTCTCTCTCC CTGAGCTGGC AAGGTTAATT GGTCGCAGAA AGCCGAAGAA
1141 ACAAGTGGGC CTCCTGGAAC AAAGTTCAAA AAGCCGAAAA CGGGAAGAAA ACTAACCACA
1201 AAAGTAAAGG AACCACTTAG CCTTCTTTGA TTCCAGGCCC CCAAGCCTGT CTTTAACTTG
1261 GATGAATGA GTTCTTCCTG TGCTACAGCA CCGCATAGTA GGGGCTGCCC TGGCCCTGAA
```

FIG. 10B

```
1321 GCCAGAGCTT CACCATATTC AGTCATCTGT ACATTGAGGC AACAGTGCCT GCTTCATGGT
1381 GCTACCCTGT GGATTAAATG AAGCAAGTTT TTGATGATCT TGACACTGAA TATTGATGCA
1441 TTGGTCAGAC TTTTCTGAT AGTAAAAAAT GGTGGTTTCT TGTTGTCAGA AATCAAATCA
1501 ATATATTGT TCTCCTGTTG ATTAGCTATG TCCCCTAGAG GGCAGCGACT TTGCCTGTCT
1561 TATTTATCTC TGCATCTCCA GCACTTAAAA GGTGCCTTGC ATAAGGTACA TATTAAGTTC
1621 ATATGAATGA ATGAATGAAA TGCATATGAT TTATTCATAC CCAGTTGGTG GTGTGTTTAC
1681 CCTTTCCTAA ACCTGTAGTC AGATGGCCTT TGAATCCCCT GTACTTCTTG TGAGGTACTG
1741 TGCTGTAAAG GTGGACTATC ACACTTCAGT TCAGAGCAAT CTGGGCTTGA ATCCTGGATT
1801 TGCCAGTTTA TTAACTATAG CAAACATTTT TGAGCATACA TTGTGCCAAG TGCTAGGCTA
1861 ACTGTCTTAC ACACTTCGTC TTATTTCGTC TTAATATCTA TGAGTCATGC ACTATAATCA
1921 TCCCCATTTT ACAGATAAGA AAGCAAAGAC TTGGAGAGGA AAAGCATCTT GTTCAAAGGT
1981 AAATACTTAA TGGCCAAGCC AACATGCAAA TCTAGATTA ATTGCAGCTT CCTCTTCATC
2041 TACCATTCGA ACTAATTCAA GCTATGTAAT ATTTCCCACT GAACCTTCTT GCCCTCTACTT
2101 CCTCATCTTT AACATGGTCA AAATACCTGT CCTGCCCAAG TTAGTTATTT CATTAAAGTA
2161 GAAAAATACA AGAGAAGCTT TTAAAATGTG AAACCTCAAA TGAATGTAAA ATTATGATGA
2221 TTCCTTTAGA ATTTGTCAAC ACCTTCTTTT CTCTACTCCT GCTAGGCATT TACAATCTCA
2281 AAACCATGTA TTTAAGATGC AAAACTATAT TTGTATTTGC CATAACTGGT TTCTTTCCCT
2341 ATGGCTTCAT GAAAATGTGG CTCGAATGTG TTTATTATGA AAGCCCCAAA TTAATCACGA
2401 CAAGACTTCA CCAGCCCATT CCACAATAGA CTCCCATTAC TTTGCCCTGA CTTAGAAACC
2461 TCATATACAG TCTTGATTCA GTACAGCTCT GTGATGCTCT TGGAAAATGC AAAGTGCTTT
2521 CTTAATTGAG GCAATCTGTG TCCCACTACA GAGAGGTGGT TTAACTTGTG AATTC
```

FIG. 11A

```
   1 AGAGCAACCT GGGCAACATA GCAAACCCT GTCTCTGCAA ACAATAAAAA GAAGAAAATT
  61 AGCTGGGTAT GGTGGCACAT GCTATAGTCG CAGCTACTCG AGAGGTTGAG GTGGGAGGAT
 121 CAGTTCAGCC TGGGAGGTTG AGGCTGCAGT GAGCCAGATC ATGCCACTGC ACTGCAGCAT
 181 GGGCAACAGA ATGAGACCCT GGCTAAAAGA AAACAAAATA AAAATTCAG ACACAGGTTG
 241 AATCATTGAT AACAGCATAG TGGTAACAGA AAGAAAGTTT GGGAAATTTT TATCTGATCA
 301 GCTTCCCATA CCCTGTTCAT CTTTGTGTTA TGCACTGCCA GGCTGTCTGT AGGTTCAGAC
 361 TCTATATCAT ATGACCTTCA AACACTTGGT TTGTTCTTCT CCTTCCTTCC TCCCTTCTTC
 421 TTTCATTTTT TATCTTTTTT TCTTTTAAAA TGTTTAGATA GTATAATAAG GAACTGCTGA
 481 GGCTTCCAG TGCCCTCCCTC AACATCCGGA CAGCTAAGGA GGATTTCACT TTGCACCTTG
 541 AGGACGGTTC CTACAACATC CGAAAAGATG ACATCATAGC TCTTTACCCA CAGTTAATGC
 601 ACTTAGATCC AGAAATCTAC CCAGACCCTT TGGTAAAGTC GCAGTGTGCC CGAATTGAAA
 661 TTCAATATCC AGGTGATAGC TACCTAGATC TAAATAAAGA GGAAATTTAC AATGGTAGAA
 721 TTGATTTTCT CATAGTAGTC ACAGGAAATG TCTGACTTAA TTGTGTTAAA TATTCATATA
 781 TTTTGGAAAA TTTAGATAGT GGTCTGAATT TTTCATTTTA GTCCTGATAT TTGCCATCAC
 841 ACAGTCTTTG CTAGATTATA TTTGCAGTCA TGATAATAAA CCTGCCACTT TTTTTTCTT
 901 AAAAGCACC TCCTCCCAAA TCCAGAAAT TGGAGGCTAA TATATTGATT ATTCTAGTTT
 961 CTTCTGGGAA CCCTTCTCTC TCTAGCTCTG CCTGACTAAG GAACTAATCG TTCAAGCAGG
1021 ATAGGAAGGT ATCACAAGGC TTCCTTAGCT GCATTAAGCT CCTGTTCCTT ATTACTTTCT
1081 GATTCAATGT GGAGTATTTG CTAAATCACT AATGGGGTAG AATTAAAAAG AAAATTACTC
1141 TTTGGAGCTT CCAGGTTTAG AAAGAGATAA ATTTCTTTAA AACTAGCTTA AAGGCGGTTT
```

FIG. 11B

```
1201 TCTTTGTATT TTTATTGCAG ACTTTTAAAT ATGATAGGTA TCTTGATGAA AACGGGAAGA
1261 CAAAGACTAC CTTCTATTGT AATGGACTCA AGTTAAAGTA TTACTACATG CCCTTTGGAT
1321 CGGGAGCTAC AATATGTCCT GGAAGATTGT TCGCTATCCA CGAAATCAAG CAATTTTGA
1381 TTCTGATGCT TTCTTATTTT GAATTGGAGC TTATAGAGGG CCAAGCTAAA TGTCCACCTT
1441 TGGACCAGTC CCGGGCAGGC TTGGGCATTT TGCCGCCATT GAATGATATT GAATTTAAAT
1501 ATAAATTCAA GCATTGTGA ATACATGGCT GGAATAAGCT GACACTAGAT ATTACAGGAC
1561 TGCAGAACAC CCTCACCACA CAGTCCCTTT GGACAAAATGC ATTAGTGGT GGCACCACAC
1621 AGTCCCTTTG GACAAAATGCA GTAGAAAATGA TTCACCAGGT CCAATGTTGT
1681 TCACCAGTGC TTGCTTGTGA AATCTTAACA TTTGGTGAC AGTTTCCAGA TGCTATCACA
1741 GACTCTGCTA GTGAAAAGAA CTAGTTTCTA GGAGCACAAT AATTTGTTTT CATTGTATA
1801 AGTCCATGAA TGTTCATATA GCCAGGGATT GAAGTTTATT ATTTTCAAAG GAAAACACCT
1861 TTATTTTATT TTTTTTCAAA ATGAAGATAC ACATTACAGC CAGGTGTGGT AGCAGGCACC
1921 TGTAGTCTTA GCTACTCGAG AGGCCAAAGA AGGAGGATGC TTGAGCCCAG GAGTTCAAGA
1981 CCAGCCTGGA CAGCTTAGTG AGATCCCGTC AGATATGTAT TCTAATTGGC
2041 AGATTGTTTT TTCCTAAGGA AACTGCTTTA TTTTTATAAA ACTGCCTGAC AATTATGAAA
2101 AAATGTTCAA ATTCACGTTC TAGTGAAACT GCATTATTTG TTGACTAGAT GGTGGGGTTC
2161 TTCGGGTGTG ATCATATATC ATAAAGGATA TTTCAAATGT TATGATTAGT TATGTCTTTT
2221 AATAAAAAGG AAATATTTTT CAACTTCTTC TATATCCAAA ATTCAGGGCT TTAAACATGA
2281 TTATCTTGAT TTCCCAAAAA CACTAAAGGT GGTTTT
```

FIG. 12A

```
   1  GAATTCTAAA CACATATTAA TATCAATGAC TTATATGTAT GTATATATAT ATCTAATATA
  61  GATAATGTAT CTAGGATAT  ATATATATGT ATATTTATC  TTTCTTCCTT TTATTCTTTC
 121  TTCTCCCCTC TCTGTGTCAAC ACCGAGGAAT AGAATGCACT GTGGTGTCAT ACTCTGCTTA
 181  CTCAGCCTCT TATTGACCTC TGAGTCAATA CAGTGCTGAT GTACATCTCC AAATGCCCTC
 241  TTTTCTCCTA ACCACAGACT TTTACATTCA GTAATCAATT TGACATTGTC CCATGATTTA
 301  CAAATGTTCA CAATAGTATA TGACCTATT  GCTGCCTTCC AAGGTCCTCT CCCACTCCCA
 361  AACATCCCAA TATGAACCAG CTTTTGCCTA TCTCTTGTC  TCTTACTTTA ACTCAATGTC
 421  ATTCCCTATT CACTTTGCTG TAATAGATGC TACCCTGATT CTGGTTTTA  GCACCTTAAT
 481  TTCGCTCTCT GCTCAGGAAC TCTGCCTTTG TACCCTTCCCTC TTCTGGGAAC GCTTTTCCTT
 541  TGCTGTTATA TCTCTTCAAA ACAGCTTCTC TATTCAATAT CTTCAAGCTG CCTTCAGCCC
 601  TCAACAGCTC TCCCTACCTC ATTCTAGTCC CTCCACTAGA ATAGAATCTT CATGAGAGTA
 661  GCGAACTTCC CTATCTTGCT AGTACCCAAA GGCAGAAAAA TCTTTAAAGA GTTCCTGGGA
 721  CATAGAAAAA GTGCTCAATT AATATTGTA  TTAAATAGGG ACCTCAGGTG TAACTCCGTG
 781  GTAGAGCGTT TGCCTTAGAG AAGTAGGGCC ATGGGTTCAA ATTCCAGCAC AGAACAAAAA
 841  ATTGTGCTGA ATAAAGTTTG GGAGGATGTG TAGCAGTTTA TAGTGCAAGT GGCATAAGCA
 901  GTAATAATG  AATTTGTATC CACTTTTCTA GCAAGAAGTA TTTTATTCTT TATTGAAGG
 961  ATAACAATTG GTAAAGACTG CATTCTCAAA ATAAACTATG GCTTATGGCT ACGTGGAAGA
1021  TGAGATAGGG AGAAGGTTTT TTTTGATGA  TGGCAAAATA ACATGTCATA GTCCACACGA
1081  AACACCTGTG AAGTTGTAAA CACACCTAGC AATCAAACAA GAAAATTGTC CCACCCTATT
1141  ATCATTCTTT TGGATTGGTT GTGGCATATT TCTGGAAAAT GATTTAAATT AATTCCTTCT
```

FIG. 12B

```
1201 AAGGTAACA ACACAAACAA CCACTATCAT GACGAAAAGC TTCTGCCTGT TTCAGTTTAC
1261 ATCATGCTCA ATGTCTACAA CAGACGTGCT CATCTTCAGA GTGTTTACCT CTGCTTTTTA
1321 CACACATTGA AGCACAATGT GAGCTGCTGT CCCTGGGTCT GAATGTTATG TCAGCACACA
1381 AGGACAGAG CTTCGGCTTA TCAAGTATTG AAGCTCTCTG CTTGTTTTGG AGCCTCTTCT
1441 GATACTATGG ACTTAGTTCA AGGCTGGGCA ATACTATTT TTTCTTTTTT CTAATAGGAG
1501 GACAAATAGT TAGTTGTTTG CTTTGGTCAT CCAAGTTCAA GTTATTGGAT CATGGTCCTA
1561 TGTGTATAAA GAGTCTAGTT TGAGCCTTTC AGGGGCAGCC TTGCTGGCTA AGCACAGACT
1621 CTCCTCTTGG GAGTTTTCCT GCTTTGCAAA ATGATGACCA TCTCTTTGAT TTGGGGGATT
1681 GCTATGGTAG TGTGCTGTG TATATGGGTT ATCTTTGACA GAAGGAGAAG GTATGTCTTT
1741 TAGCTTATTT CTAGTGTTT CACTATTATA CAGTTCCAAA AAAATACTAC TACATTAGTA
1801 TTTTATTTA AAATTAAAG CCATGCTTCT CTGACTAAAC CTGACAAGAT GTAGAGTTTC
1861 CCTTTGAATA TCCACATACA CTGATGGTAA TGCTGATCTT GTTAAACATA ACTAAAAAAA
1921 TTATAAGTAT TGATGCATGT TTGTGTGCAC TTCTGTGGAG TACACCTAAG CTGGGAAGGG
1981 TGCATTTGGC AAGGGTGACG TTTGGAAAGG ATCTTTCTCT CACAATAACT GGTTATGCAT
2041 ATGCTCTTCT GGGTTCTCTG TTACATCAAC ATTAAAAATAC AGGAATACCC TTGGCATATC
2101 TTTGGCAAGG TAGACTGTGT CTGCTGTCTT AGTTTGTCT ACTTCTTTGC CTTTTGAGTT
2161 ATTTGAATT ATGCCCTGATC GTTCCAGTT TTAGTTGTCT TAATGCTAAG AAAGGACAAA
2221 TCAATTATAT TTAGTTATTC TAACAAGAGA TAACTAGTTT ACGTTGAAAA ATAAATTATC
2281 TTATAATTC TAATAAAAAC ATTTAAGAGA GTTAGAAATC AGCGAATTAT AGCTGATGAT
2341 CTGCCAATGT TTACCTCACT CAACTTCATT TTAGATACTT TTTCAAGTGG GATTCCTATT
```

FIG. 12C

```
2401 CTCTTCAAAT ATCCGCACAG AATTATAGTC CCCTTCTTTC AGAGTGGGGG GAATCAAATG
2461 AAAGGTTTCA TGTGTGCTAG GCAAGAGCAC CACCGTTGAG CCACACCTCC AGACCCCACA
2521 ATGCCAACAT TTTTAAACTA TGTAGAGTTT AAAAAACTTT AGTTCTGTAG CCTTTCTAT
2581 TAGCTGGTGT TTCATGTCTT CAAAGAAAAG GAAAACTGAA ACATTTTAGA CATATGGACA
2641 AATGATTCCT TGAACAAGTC TAAGCACTGA TGATAGCTTC TTTCTACACG TGAGATCAAG
2701 AATCTTGTTA GCCCTGTTGA TACTTGTAGC CCTGTCACTT GGAAAAGCAA TCAATTTTAT
2761 GATCTAGAAA ATAGAGCTTG CCTAAAGATC AGAGTGCAGA GCTAGTCACA CTAGTCAGCC
2821 ATACAGGTTA GGCAGTGGTG GCACATACCT TTAATCCCTG CAGCCACTCA AGTACCCAT
2881 AGAAGCTGGG TGGTGGTGGT GCACACCCTT AATATAAGGT GGAGCACACT TTAATGTAAG
2941 GTGGGTAGAG TCAGGAGTGC AGTGTATTCA GTCTGCAGTC ACACTGAGAA CAATATCACC
3001 CCAGTCTTGT TAGAGGTAAG AACTCTCTAG TGATTGGCTG CTTGCTCTT CTGATCTTCA
3061 GTTTGAACTT CTGTCTCTGG GTTTTTATTA TTCGTGCTGC AGACATAGAC ATAGCAAACA
3121 ATTTAATGAG TGATTGATGA ATGTAGATAT GTATGTACAT ATTGTGCTGG ATAGACTGTA
3181 GATGGGTTGG TGGATGGGTT GATGAGTGGG TAGATTTAGT AATCACCTTC ACCAATATCT
3241 TAGTAGGCTA AAAAGCCCAC TGTTTTAGTA AAAGAGTGGG GTATCCAACA AAGAAGTATC
3301 TATAAACTGT AGTTATGTGG TAGAAATAAG GGGTAGAAAC CAGTAAAAAT TCGGCTTATG
3361 TACAAATGCT AAACATGTAA TTTCCTAAAC CTCTCAATCT GTCTCACAGG AAAGCAGGTG
3421 AACCTCCTTT GGAGAATGGG TTGATTCCAT ACCTGGGCTG TGCTCTGAAA TTTGGCTCTA
```

FIG. 12D

```
3481 ATCCTCTTGA GTTCCTGAGA GCAAATCAAA GAAAGCACGG TCATGTTTTT ACCTGCAAAT
3541 TAATGGGGAA ATATGTTCAC TTCATCACAA ACTCCTTGTC ATACCATAAG GTGTTATGTC
3601 ATGGAAAATA CTTGATTGG AAAAATTTC ATTACACTAC TTCTGCAAAG GTAACTAGTT
3661 TTTACAGATT TTGCTTGTTT ACTAGCCTGT TTATTATTA GTTTATTTAG TTGTTCCAAT
3721 GTTATTAGAT TGTAGGATAA AGGGAACATA AAATCAGGAA GTCTCTTGGT ACTAAGCATT
3781 AAAAAGTCAA GGTAAATGTG AATTTGTGAT TGATGATGAC ATACACAAAT TAAGCACTTT
3841 GTAAGTACTT TCTGAGCCAG AAGACACTAC AGGAAGGCAC AGACTCATAA CATCCATGCT
3901 GCCATCTACA CAACACTCAG AGCACTCAAT TACCACATCA TGCACACGAA CTCGTTCGTT
3961 AAGAAGTCGA CAGTATATTT AGCATCATT CAGATGTTAT CAAGAATCTC TATTCTAGAG
4021 AAACAACAC TTAGCTGAAT TTTTACAAGA AAATATTAGA CATGGTCTCT GTCTTAAGTA
4081 GATTAAAGTC TGGCTAAAGT GCATCTGCAG AGAACAAAAG GTAAAGATAA AATCAATGGC
4141 CCATTAGTCC AGAGAAGCTT ACCTGAAAAT CTGGGATTTA AACTTGACCT TAAAGGAAGA
4201 GTATGTCTTA AGTTTGACTT TGAAAAATGT TATGAAATTG TATGGGAAG GCTAGACAGA
4261 GAAGTATGAT ATACTTTAAT CCATCTTCCT GCCATTTCCT AACACCCAGG TTTAGCTGCT
4321 CCCCCTCTGA CGAATTTCAT TTTCTACCAG GCATTTGGAC ACAGAAGCAT TGACCCAAAT
4381 GATGAAATA CCACAGAAAC CATAAACAAC ACTTTTACCA AGACCCTCCA GGGAGATGCT
4441 TTGCATTCAC TCTCTGAAGC CATGATGCAA AACCTTCAAT TTGTTCTGAG GCCTCCTGAT
4501 CTTCCTAAAT CAAAGAGTGA TGCCTGGGTC ACCGAAGGGA TGTATGCCTT CTGCTACCGA
4561 GTGATGTTTG AAGCTGGATA TCTAACTCTG TTTGGCAGGG ATACTTCAAA GCCAGACACA
4621 CAAAGAGTGC TTATCCCTGAA CAACCTTAAC AGCTTCAAGC AATTTGATCA AGTCTTTCCG
```

FIG. 12E

```
4681 GCGTTGGTGG CAGGCCTCCC TATTCACTTG TTCAAGGCGG CACATAAGGC CCGGGAACAG
4741 CTGGCTGAGG GCTTGAAGCA TGAGAACCTC TCTGTGAGGG ACCAGGTCTC GGAACTGATA
4801 CGTCTACGCA TGTTTCTCAA TGACACTCTC TCTACCTTTG ATGACATGGA GAAGCCCAAG
4861 ACACACCTCG CTATCCTCTG GCCCTCTCAG GCAAACACTA TTCCTGCAAC CTTCTGGAGC
4921 TTATTCAAA TGATCAGGTG GATAGCAATT TGAGTGTTTA TTCTTCATAG TGACAGAAAT
4981 TAACAATTTT TAATAAACCC CCCAAAAGAC TAGCAGAGCT TTCTTTGCTG TTGGTCAAGA
5041 ATGTGATACT CAGTGCCTGT GTTTGACATA TATATATAAC AAAAGTAGCA TTTTGTAAGA
5101 ATATAGTCTC ACCAGAAAGG GATGTCCCAG AAGCCGCAGA ACTTAGATCT GCTGGCACTT
5161 GTCATTAAAG GTCCCCTTGC CCAGTCTTGC TTTTAACTCC ATAGTGTTCT TCTTAGTGTC
5221 AAGTAAATC TATGACTGCA GTCTTCATCA CAACTTTAAA TAATGACTGA CTTGTCAATG
5281 TGGTAAGTGC AGAGGCCACA CCTTACTAGT TTGAACATTC CTGTTTTCTG CGGCCTCACA
5341 GATTACAGC AGAGTTGCAA CATCAATTTC ATATTACCTA TGAACTACAA CCATATTTA
5401 AGTTCAACAA CTACTTGTTA GTAACATTTC TGAGGCTCAG TTCACTTTAA CCAGATAAAG
5461 GAGATTTCAA ACAGCTGCCA ACAAATTTCC ATGCACTGAA TGGAAGTATT CTTTATCGCA
5521 CAGTTCAAAA ATAATAACAT AAATATTCTG AAGCTGTGGT ATGAATTAA AGAGTAAATT
5581 TGAATTCTA CTTGGGAATT CACCAATACC CTGTAATTGT ATGTTAGAGG AAGTATTCGG
5641 AATGAATTAC TCTACTCATC ACACGAATGT CTAGCCCCTA. TTAGAATCAT TGGTTTATAG
5701 AGATCTGACC AAAGCTTTGC TTTTACATAG CAACGCCCCT TTAATGCTTC TTCATAAATT
5761 CAAGGACATG AATCCAGTTC AGAATACAGT ACAAGTAAAT GACAATGCCC TTTGCATGTT
5821 CCTGGAACCA CTTCCCTTTT CATGCTCCCA TGCTAACGCG ATCACCTCAT TAAAAGAAAT
```

FIG. 12F

```
5881 GGAGTTCTTA TTTACTTGCA GCTCTCTGAA TAAGGCAATA TCTTCCATAT GTCTCTTTTC
5941 ATAGGAGTCC TGACGCATTG AGAGCAGCCT CTGAAGAAGT GAATGGAGCA TTACAGAGTG
6001 CTGGTCAAAA GCTCAGCTCT GAAGGGAATG CAATTTATTT GGATCAAATA CAACTGAACA
6061 ACCTGCCAGT ACTAGGTGTG TTCCCTATGC TATCCCCTCAC TAACATGTCA CTAGTAACAA
6121 TGCTCAACAT ATAATGAATG TACTATATTC TTGATATTTT TGCAACGCTG CAACAGTCTA
6181 ATAACTAGGG TCATCTTTCAT TTTTCTAAC AAACAAGGAA CTGAGACCCA GAGCGTGGGA
6241 CAGTGGCAAC CCTGGCATAG AACATTTGAT ACTCAGTTGC TCTAGGTCCT TGGCCTCCTT
6301 TCTTAGTCCT CCAAAACCAC AAACCCAGGG TTAAGGAAGC ATGGAATTAA TGTGAACAAA
6361 GCAACACCAC TGGTTTGGGC GATGAGACTG AGGCTTTTCT TCCTTTGTTT CTGTATTTTC
6421 TAGAATGCAG TAGTACCATG TATTACAGTA AAACAGCCAT ATTTTTGTGT CCTGTTCTGT
6481 AAAGGACAGA AGCCCCCATA TGCTTTGAGG GCAGTTTAGT TTATTAGAAG CAACAGAGCC
6541 TAGATTCAGC ACTGCCTGGT TTGGGACCTC CCTTTAGACA CCTCCCTTTT CTCACCTGTA
6601 AATAAAGGCT AAGTAAGCAT TTGTGACTGC ATACTCAGTC ATGGCCTGAA TCCTGGGAAC
6661 AAGGCAGCTA GCAGCTAGAG GCTGGAAAAC AGGACTGGAC CTCAGCAGCT CTACTGCATT
6721 ACTTCCCCTA GAAGCAGGGT GTGGCTACAC AAAACCAGAC AGATAATGTA TGGCTGAATG
6781 TAGATTCATG AAATGCTTGG AAAGACATT ACTTATCAGT ATGTTTAATT CCCAAAATGG
6841 TCAGCAACAA TTCACACAAA ATTGATTATA AGTTTTTTCA ATTGCTTAG CTGTTTAGTG
6901 TCCAGTAGAA ATAAGATTAC TATTCTATAA AGTGACAGAT GTTCATCTAG TTCCCATTGA
```

FIG. 12G

```
6961  TGGTGAAGAA CATTATGTCA TCCCAAAAGA TCGTTAACTT AGATCGTGT TCTCTACCTT
7021  CCTGATGTTG TGTGACCCCC AACTGTGAAA TTATTTCAT TGCTACTTCA CAACTATAAT
7081  TTTGCTTCTG TCATGAATCA TAAAGCAAAT ATCTGTGTT TCTGATGGTC TTAGTGACC
7141  CCTGTGAAAG GGTCATTTGA CTCTACCCCC TACATGGGGT GTGATCCACA GGTTGAGAAG
7201  CACTGACTTA GATTCTCAGA TTGCAAGTAG AGCAGCAGAA TTTCGAAGAA CAGCAGTGGC
7261  GACAGAAGCT GCTTTGGGCA GTTGTCATTT GTTAGCTTTC ATTGGCTCAT TTTGTATACA
7321  GATTTCGGA AGTATTTCAG ACTTTATGTT ATGTAGCCTT TAGAGGCAAC AGTTCAGGAC
7381  TGGAGAGATG GCTCAAGGGT TAAGAGCACT GGCTGTTTT TCAGAGGACC CATGTTTGAC
7441  TCACAGCACA CACATGGTGG CTCACAGCCA TGTTCCAAAG GATCTGATGT
7501  CTTCTTCTGA CCCTCTGCAGA CACCAGGCAT GCATACATGC AGGCAAAATA CCCATCAATA
7561  TAAAAATAAA TAACTGGGAA ATATGCAAAT TCTTTAATAT TCTTTAATCTT CTCTCCCCAA
7621  CTGCCATTTC CCATGCTCCA CCCTCCATCCC TTCCCTCCTC TCTTACTTCT TTTGTTTGGA
7681  ATTCTTTAGA TAGCATCATC AAGGAGCTC TGAGGCTTTC CAGTGCATCC TTGAATATCC
7741  GGACTGCTAA GGAGGATTTC ACTCTGCACC TTGAGGATGG CTCCTATAAC ATCCGAAAAG
7801  ACGAACATCAT CGCTCTTTAT CCACAGTTAA TGCATTTGGA TCCTGCAATC TACCCAGACC
7861  CTCTGGTAAG TTTTTCTGCT CATCAAAGTT ATGTATCGAG GTGACAGTCA CCCAGGAATG
7921  TATTTGTAAT TACAGCTTTG ATTTGATCAT TAAAGTGAAG CCATAGGGAT TGTCCCTCTT
7981  TATTGCGGCA AATATTCATG TTTGGAAAC TTTGGGTAGA GGCAAGAGTT TTGAACTTTT
8041  ACACCTAATA TTCATTTCAT AGTTTCTGCT AGACTATGTT TTCAGTCATA ACAAAACTAC
8101  CACCTTTTTT CCCCCTCACA AAGTACCCTC TCCCAAATTT ACACTAATGG AGGTAATGC
```

FIG. 12H

```
8161  ATTGACTTG ATCCTTAGAG TAGTGTTTA GAGCCATTTT GCTTCTTTTG TCTAACTGAA
8221  GAATTAGTCT ACAGGTAGAA CAGGAGGTCC CTAGAGCTTC TTGGTCCACC AGCTCTTCAT
8281  AAGCTCTTTC CAGTATCACC TGGTTCAGTG CTTGGTGTTT GCTAACTTGT AGAGGATGGA
8341  TTTATTAGTA GAAAATTACT CTTTGGATCC TCCAGGTCAA GAAGGCAACA ACTTTCTATC
8401  ATAATAGCTC ATTGGCTTCT TGTCTCTTTG TTGCAGACTT TTAAATATGA TCGATACCTG
8461  GATGAGAACA AGAAGGCAAA GACCCTCCTTC TATAGCAATG GAAACAAACT AAAGTATTTC
8521  TATATGCCAT TTGGATCCGG AGCTACAATA TGCCCTGGGA GACTATTGC TGTCCAAGAA
8581  ATCAAGCAAT TTTGATTCT GATGCTTTCA TACTTTGAAC TGGAGCTTGT GGAGAGTCAT
8641  GTCAAGTGTC CTCCTCTAGA CCAGTCCAGG GCAGGCTTGG GGATTTTGCC ACCATTAAAT
8701  GATATTGAGT TTAAATATAA ACTGAAACAT CTGTGACATG TGGTTGGAAG AAGAGGACAC
8761  TGGATGATGT TGCTGGACTG CAGCGAGTCT CACTAAACAA GCCCCTTGGGA CAAATGCTCT
8821  CCTTTGCTTC CCAGCAACTG ACTGTGCCTA TGGTACCCCC GGCACCACTC
8881  TCTGTTCTCA CTGCCCTGAGT TCCTGGGTGT TCAGATAGCT GAGGTCAGAG TTTCACCACT
8941  CTTAGAAGCA ATGTCTTTTG TTTTTATTTT CAAAATGAAG ATACTCCAAT TGGCAGATTT
9001  TTTTTCCTAA GGAAATTGCT TCATACTTTT ATGAAAACTG ATTAATTATG AAAAGGCTTC
9061  AAATTCACGT TTTAGTGAAA CTGTTATTTT TTTCACTAGT GAAGTCTTC ATGTGTGAAC
9121  ATATACTATA AAAACATTTT AAGGATCAT ATCATGCTTT GCATAAAGGG AAAGAAAAT
9181  ATTATTCAAC TTTTTTTTT GGTTTTTCTA GACAGGGTTT CTCTGTGTAG CTTTGGAGCC
9241  TATCCTGGCA CTCACTCTGT AGAGCAGGCT TGGTCTTGAA CTCACAGAGA TCTGCCTGCC
9301  TTTGCCTTCC GAGTGCTGGG ATTAAAGTCG TGCGTCACCA ATGCCCTGGCT ATTTAACTTT
```

FIG. 12I

```
9361  TTCGATGTCT AGTGGTGAGA GCTTTGAAAA TGATGCTACT GTGTTGGGAA TACTATGGGA
9421  AATTTGATG  CTTCGCTGTT ACATTAAAT  TTATTGCTGC TGGAAATTGT CACCCCAGTT
9481  TTCAATGCC  CCTCTCTCTC CCTTTTAATA TTCACACTGA TGAGCAGAGT TTTTAGAGA
9541  TTAAAAGAC  CTCCCCAGAG CCCTGTCTCT GATGTTTTTA AGCCTTTAAT CTCAGTACTC
9601  AGGAGGCAGA GGCAGGCAGA GCTCTGTGAG TTCGAGGCCA GCCTGATCTA CAGATCGAGT
9661  TCCAGGCAAG CCGGGCTAC  AGAATGAGAC CTTGTCACTA AAAGAAATAA ATAAGGTCAA
9721  TTTTATGTCA CAACTGATTA TGAATCATTG TAAAGGATAA ATTGAAAAAA AAGAACTCCA
9781  CGGGAATGAC CATTAAAATG GTCTATTTTA GCTAAAATTA ACTATGAATT ATGTGGAGTT
9841  CATTAAGTGT ATGTTGACGT TTTAAATGT  CTTATGTTTT ATCTCTGAAT
9901  GTCTTGTAGA TGGAGAGCAA TATATGTTCC TAAATACTGA GTCAATAAGG TTTTATCTAT
9961  GTACTTTAAG AGCATTATTA GCTGTGTCAT TTTTACTGAT ATATCTAATA TATTATATG
10021 TAAATTATAT TTATCTTTTA TCTTATACTA CAAATATAAG TAAATATTTT AAAACCAGTA
10081 ACTTTAAAAT TACCTACCTT TCAGAAATGA AAATAAGAAC ATTTGTGCTT TAACCTTTGA
10141 AATAGAATGT TTATTCATCC ACTGATAAGT TAAAATAATT TTATCTGATT TGTTTCAAGA
10201 AACTCAAAAA TATTCAAAGT AATCATGCAC TCAAAGGTCT TCGTAAGGTT ACAGAAAATT
10261 CAATAAAATC TTTTTGTGT  AGGGACTGAG TCAGGGTCTA GAAGATGCTT GGCAGGTACT
10321 CCAGTAGTGA GCTGGATCCA GAAGATTCCT TAAACTTTAA AATCTTAACA CTAAGTATTA
10381 TCACAGAGTT ATTACCTAAG TAGAATATTT TTCCTTTCCT TTTCAATTGA CAGAGTCCCA
10441 CAGCAACACA GCTGGCTGTA ACTCTTCACA TAGCTTGCGC AGGCTTTGAA CTCACTGTAC
10501 TCCTGCCTTT CCTTTTCTAG GAAATATTT  TCCACATCAA GAAAATTTAA TTGTTCCGAT
10561 GAGGTATAGA GTAACAAATT TCTGTTTATAT ATTCATCTGT ATTAAACTGA ATTC
```

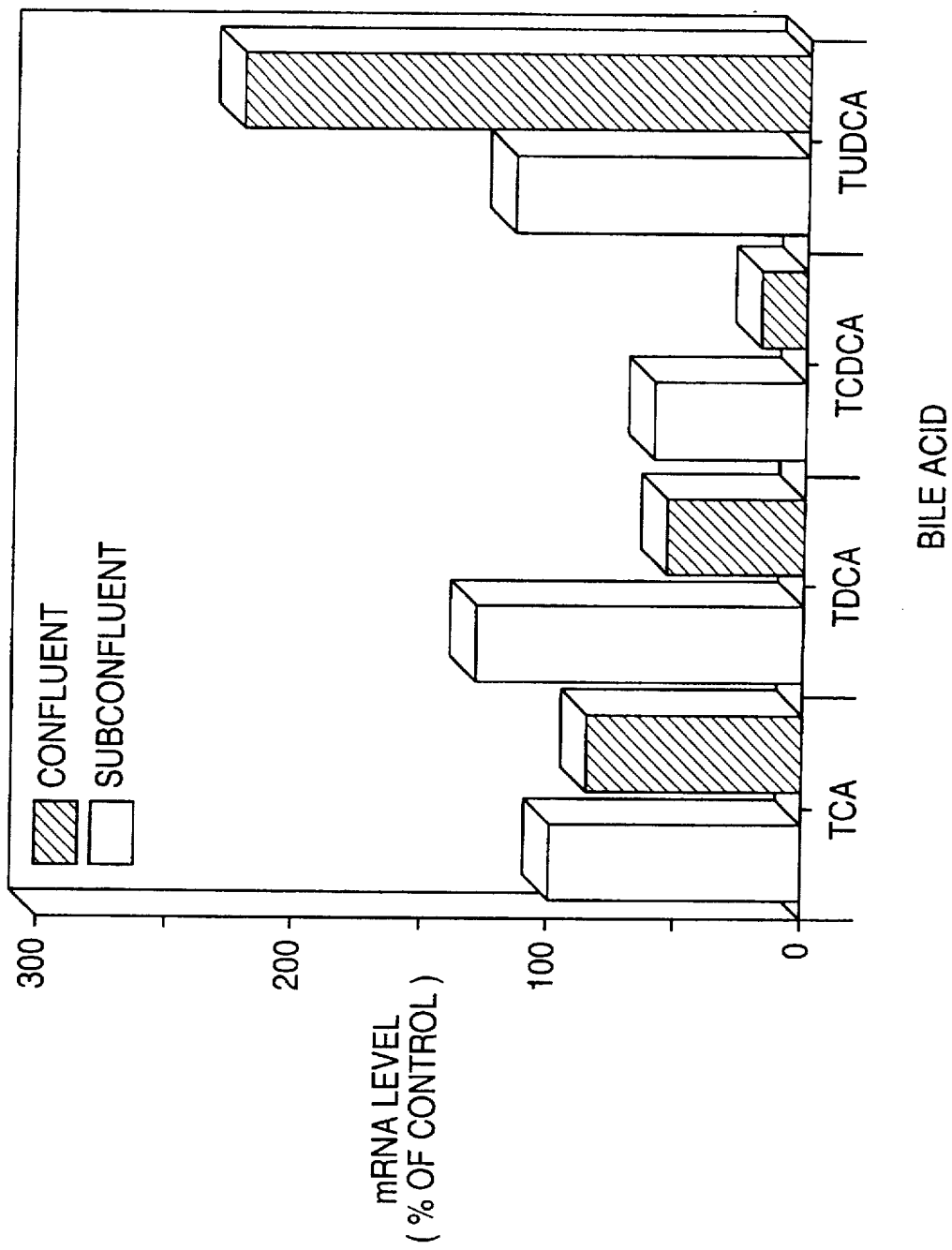

500
CHOLESTEROL 7 α-HYDROXDYLASE GENE REGULATORY ELEMENTS AND TRANSCRIPTION FACTORS

CROSS REFERENCE TO RELATED APPLICATIONS

The present application is a continuation in part application of U.S. patent application Ser. No. 08/135,511, now U.S. Pat. No. 5,558,989, "CHOLESTEROL 7α-HYDROXYLASE GENE REGULATING ELEMENTS AND METHODS FOR USING THEM," Chiang, J.; U.S. patent application Ser. No. 08/135,488, now abandoned, "GENOMIC DNA OF HUMAN CHOLESTEROL 7α-HYDROXYLASE AND METHODS FOR USING IT" to Chiang, J.; and U.S. patent application Ser. No. 08/135,510, now U.S. Pat. No. 5,420,028, "TRUNCATED HUMAN CHOLESTEROL 7α-HYDROXYLASE, METHOD OF PRODUCTION AND USE THEREOF," Chiang, J.; all three of which were filed concurrently on Oct. 13, 1993. The disclosures of each of these applications are expressly incorporated herein by reference in their entirety.

Work related to subject matter described in this application was provided by research supported in part by NIH Grant GM 31584.

BACKGROUND OF THE INVENTION

High serum cholesterol is commonly associated with an increased risk of heart attack, atherosclerosis and circulatory disorders. In addition, a variety of diseases are caused by disorder of cholesterol catabolism, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7) commits cholesterol to bile acid synthesis and catalyzes the first and rate-limiting step of bile acid synthesis in the liver. Thus, by increasing synthesis of bile acids, this enzyme plays a key role in the liver by depleting hepatic cholesterol pools, resulting in increased LDL uptake and a lowering of serum cholesterol levels.

Bile acids are physiological agents which are important in the solubilization of lipid-soluble vitamin, sterol and xenobiotics. Bile acids are synthesized exclusively in the liver and are secreted to the intestines where they are modified to secondary bile acids. Most bile acids are reabsorbed in the ileum and recirculated to the hepatocytes via the portal vein.

The feedback of bile into the liver is known to inhibit cholesterol 7α-hydroxylase and thus inhibit the overall rate of bile acid synthesis. Cholesterol 7α-hydroxylase therefore has been a subject of intense studies to elucidate the regulatory mechanisms of bile acid synthesis in the liver.

It is known that an interruption of bile acid reabsorption, such as caused by the bile sequestrant, cholestyramine, or by a bile fistula, stimulates the rate of bile acid synthesis and cholesterol 7α-hydroxylase activity in the liver. It is believed that cholesterol 7α-hydroxylase activity in the liver is regulated primarily at the gene transcriptional level by bile acids cholesterol, hormones, diurnal rhythm and other factors.

Generally, the regulation of eukaryotic genes is thought to occur at several locations, including the promoter sequences, located upstream of the transcription start site; enhancer or repressor sequences, located upstream of the promoter; within intron sequences, non-coding sequences located between exons or coding sequence; and in 3' sequences, located downstream from the coding region. The promoter sequence is unique to each gene and is required for the accurate and efficient initiation of gene transcription. Enhancers and/or repressors regulate promoter activity and determine the level of gene transcription during development and differentiation of a particular tissue.

The promoter of most eukaryotic genes contains a canonical TATA box which binds a TFIID TATA box binding protein. TFIID complex and associated transcription activators (TAFs) interact with the basal initiation factors and RNA polymerase II to activate promoter. The transcription complex assembly and initiation are regulated by transcription factors bound to enhancer elements located in the promoter and other regions of the gene (Pugh and Tjian, J. Biol. Chem. 267, 679–682, 1992). Tissue-specific transcription factors and nuclear steroid hormone receptors are known to play an important role in the regulation of gene expression in different tissues during development and differentiation.

However, the mechanisms underlying the regulation of cholesterol 7α-hydroxylase CYP7 gene expression at the molecular level are not understood. An understanding of regulation of CYP7 gene expression would permit development of therapeutics for treating patients with defects in bile acid synthesis and cholesterol metabolism due to altered (deficient or excessive) gene expression.

In order to study the mechanism of regulation of human cholesterol 7α-hydroxylase at the molecular level, it is therefore important to determine the correct gene sequence of its coding and promoter regions. An elucidation of its gene structure and its promoter/enhancer activity is sought in order to assay for an agent that modulates cholesterol 7α-hydroxylase enzyme regulation.

Beyond knowledge of the promoter sequence, a cell line is sought that is suitable for transfecting with a CYP7 regulatory element/reporter gene construct to determine the regulatory activity of a particular promoter region. Such a cell line then could be employed in a method for screening compounds for inhibiting or stimulating CYP7 expression by its direct or indirect interaction with the regulatory region, as reported by the reporter gene.

A method for detecting and isolating the CYP7 transcription factors also is sought. Further, upon determining a transcription factor, an assay is desired to discover other endogenous factors or exogenous agents that interact directly or indirectly with the transcription factor. Such an assay is useful to determine factors or agents that modulate the activity of the transcription factor and thereby affect expression of cholesterol 7α-hydroxylase protein.

SUMMARY OF THE INVENTION

An embodiment of the invention provides a DNA sequence that comprises at least one regulatory element of cholesterol 7α-hydroxylase expression. In an advantageous embodiment, the DNA sequence comprises at least one regulatory element of cholesterol 7α-hydroxylase expression in either rat, human or hamster.

Another embodiment of the invention provides a rat CYP7 promoter region, deposited as clone R7αB24 on Jan. 28, 1994, at the American Type Culture Collection, ATCC, 12301 Parkland Drive, Rockville, Md. 20852, U.S.A., under accession number ATCC 69546.

An advantageous embodiment provides a DNA sequence comprising a regulatory element of a CYP7 gene which is selected from DNA fragments in the group consisting of human CYP7 gene fragments from about -158 to about +32, from about -3643 to about -224, and from about -223 to about +32; and rat CYP7 gene fragments in the group consisting of from about -160 to about +32, from about -3643 to about -224, and from about -224 and +32.

Another embodiment provides a DNA sequence comprising a regulatory element of the cholesterol 7α-hydroxylase (CYP7) gene selected from DNA fragments in the group consisting of from about -191 to +64 (SEQ ID NO: 25) of the rat CYP7 gene, from about -252 to +3 (SEQ ID NO: 26) of the hamster CYP7 gene and from about -187 to +65 (SEQ ID NO: 27) of the human CYP7 gene, or functionally active parts thereof.

Another advantageous embodiment provides DNA selected from fragments of DNA identified in Table 1, columns 1-3.

Another advantageous embodiment of the invention provides a gene construct containing at least one of the foregoing regulatory elements and a reporter gene.

Another embodiment provides a method for determining whether an agent inhibits or stimulates CYP7 gene expression. Yet other embodiments provide methods for detecting, substantially isolating and using in an assay a transcription factor of the cholesterol 7α-hydroxylase gene.

BRIEF DESCRIPTION OF THE DRAWINGS

FIGS. 2A, 2B and 2C provide maps of the human CYP7 gene and clones λHG7α26 and λHG7α5. FIG. 2A shows the gene map of human CYP7. FIG. 2B shows the gene map of the λHGYα26 clone. FIG. 2C shows the gene map of the λHG7α5 clone. Heavy boxes represent exons I, II, and III. The arrows indicate regions for which nucleic acid sequences now are determined. These sequences are shown in FIGS. 9, 10 and 11 (SEQ ID NOS 32, 33 and 34 respectfully).

FIG. 5 shows a diagram indicating the positions at which transcription factors bind to the CYP7 proximal promoter. The following abbreviations are used: HNF, hepatocyte nuclear factor; TRE, thyroid hormone response element; C/EBP, liver specific enhancer binding protein; and TFIID, TATA box binding site representing general transcription complex.

FIG. 6 shows the DNase I hypersensitivity sites (I, II, III and IV) in the SacI fragment of the rat CYP7 gene. Heavy boxes are exons. A 5'-probe was used for hybridization.

FIGS. 7A, 7B and 7C (SEQ ID NOS 28, 29 and 30 respectfully) show the amino acid sequences of human, rat and hamster CYP7. FIG. 7A shows the human amino acid sequence, FIG. 7B shows the rat amino acid sequence and FIG. 7C shows the hamster amino acid sequence.

FIGS. 8(A)–8(E) show (SEQ ID NO: 31) the nucleotide sequence of the region of the rat CYP7 gene taken from deposit R7αB24 and indicated by arrows in FIG. 1. The transcription start site "G" is located at nucleotide position 3644. Exon I (3644–3784), Exon II (5400–5640), Exon III (6348–6934) and Exon IV (7928–7997).

FIG. 9 (SEQ ID NO: 32) shows the approximately 5.5 kb nucleotide sequence of the λHG7α26 clone indicated by arrows in FIG. 2B.

FIG. 10 (SEQ ID NO: 33) shows the approximately 2.6 kb nucleotide sequence of the λHG7α26 clone indicated by arrows in FIG. 2B.

FIG. 11 (SEQ ID NO: 34) shows the approximately 2.3 kb nucleotide sequence of the λHG7α5 clone indicated by arrows in FIG. 2C.

FIG. 12 (SEQ ID NO: 35) shows the nucleotide sequence of the region of the hamster CYP7 gene indicated by arrows in FIG. 3.

FIG. 13 shows the effect of bile acid conjugates on the expression of cholesterol 7α-hydroxylase mRNA levels in confluent (striped block) and subconfluent (solid block) cultures of HepG2 cells, determined by Northern blot hybridization as described in Example 3.3. The endpoint of the sequenced promoter region terminates at position -3643, while the full length of this sequence rat clone is 7997 (SEQ ID NO: 35) total nucleotides long.

DETAILED DESCRIPTION OF THE PREFERRED EMBODIMENTS

It was found, surprisingly, that DNA fragments comprising nucleotides downstream from about -187 (SEQ ID NO: 27) of the human CYP7 gene, downstream from about -191 (SEQ ID NO: 25) of the rat CYP7 gene, and downstream from about -252 (SEQ ID NO: 26) of the hamster CYP7 gene are regions that exert regulatory control of transcription of the human, rat and hamster CYP7 gene, respectively.

In particular, it was found that a bile acid responsive element is located within a fragment between nucleotides -160 and +32. According to the invention, a second bile acid responsive element is located in the region between nucleotides -3643 and -224. This was shown by transfecting hepatoma Hep2G cells with promoter/reporter constructs that contain these genetic elements within the promoter region of the construct. Thereafter the transfectants were exposed, for example, to bile acids taurodeoxycholate ("TDCA") and taurochenodeoxycholate ("TCDCA") and transcriptional activity of the reporter gene was repressed. More specifically, transcriptional activity in HepG2 cells transfected with construct pLUC-3600 was repressed by about 75%. When transfecting with pLUC-224 or pLUC-160, the transcriptional activity was repressed by about 45% or about 35% respectively, (FIG. 15(A)).

Advantageously, a fragment located in the region between -160 and +32 was pinpointed to interact with at least one BARP. This fragment specifically is a direct repeat without spacing, and hence was designated as "$DR_0$". $DR_0$ in the rat is (SEQ ID NO: 36) TCAAGTTCAAGT, and correspondingly in the human, is (SEQ ID NO: 37) CCAAGCTCAAGT. $DR_0$ is a bile acid responsive element (BARE) that binds to a bile acid responsive protein (BARP) factor in the nucleus of liver cells or its nuclear extracts. Accordingly, a consensus "core" nucleotide sequence that emerges from the two species of the molecule is (T or C)CAAG(T or C).

As described in Example 2.3 (b), gel shift experiments detect a BARP that binds or interacts with a bile acid responsive element 7α-TRE, for both human and rat, and human and rat $DR_0$ element. This BARP was characterized and possesses a molecular weight of about 57,000 Daltons, with an experimental error of about ±7000 Daltons.

Figure 14:
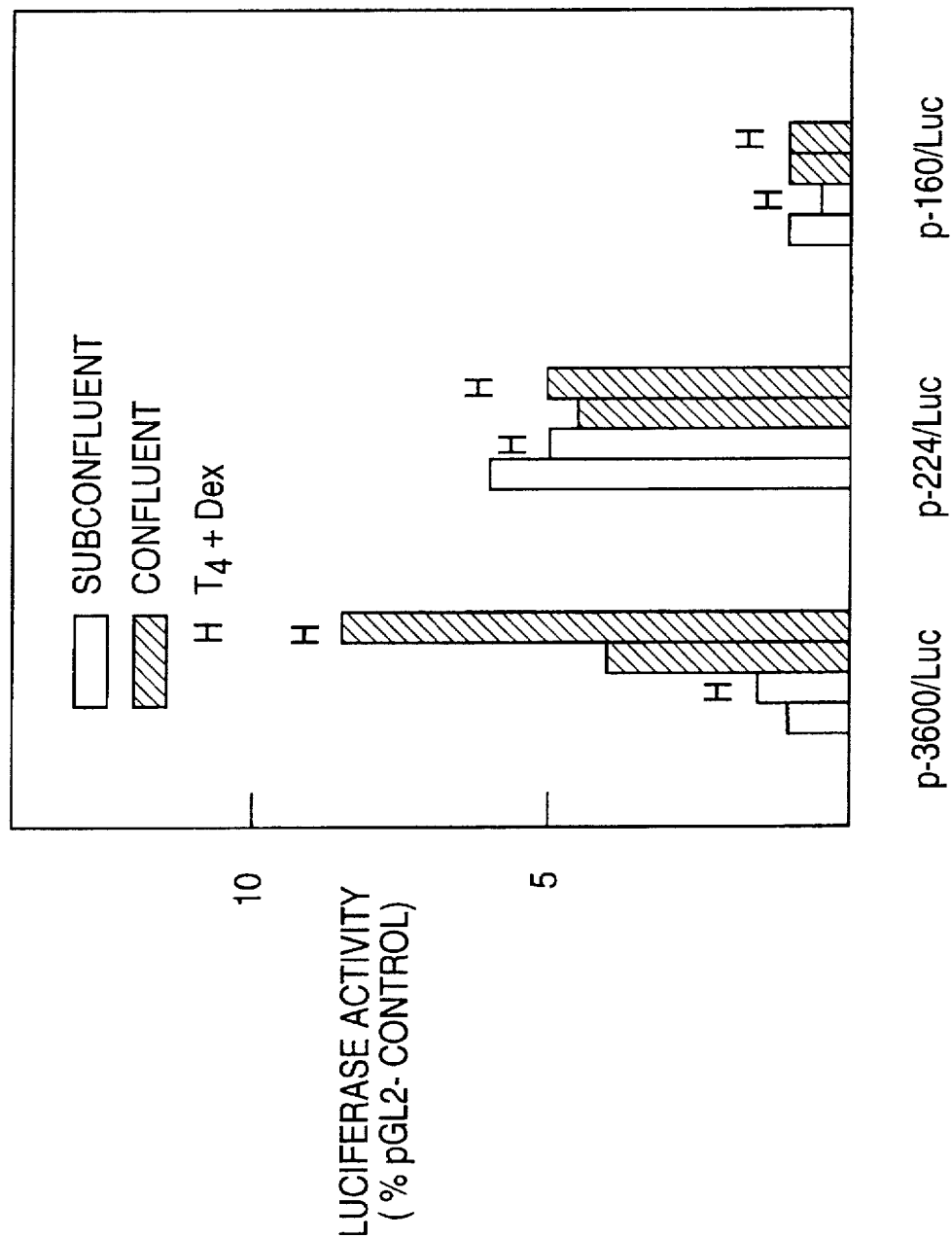
FIG. 14 shows the effect of promoter (observed in control cells), or of added thyroxine ($T_4$) and dexamethasone (Dex) on the transcriptional activity of cultures of confluent (A) or subconfluent (B) HepG2 cells, transiently transfected with CYP7/LUC constructs.

Additionally, a thyroid and steroid hormone responsive element is located between −3643 and −224 of the rat CYP7 gene. This was demonstrated by increased transcriptional activity of pLUC-3600 upon stimulation with 1 µM T4 and 0.1 µM dexamethasone by 2.5-fold in confluent cultures, as demonstrated by FIG. 14.

According to the present invention, the term "regulatory" means a characteristic ability of a DNA fragment to exert transcriptional control of a CYP7 gene in the presence of a factor that either down-regulates the CYP7 expression, e.g., bile salts or mevinolin, or up-regulates CYP7 expression, e.g., cholestyramine, bile fistula or cholesterol. Thus, a "regulatory element" refers to a DNA fragment disclosed in accordance with this invention that has regulatory activity with respect to CYP7.

Advantageously, an embodiment of the present invention provides a bile acid responsive element of a rat CYP7 gene which are selected from the group comprising DNA fragments from about −160 and about +32, and between about −3643 and about −224. A further embodiment comprises a bile acid responsive element of a CYP7 human gene which is selected from the group comprising fragments from about −158 to about +32, from about −3643 to about −224, from about −223 to about +32.

Another embodiment provides that a thyroid and steroid hormone responsive element within a fragment between about −3643 and about −224 of the rat CYP7 gene.

Figure 4:
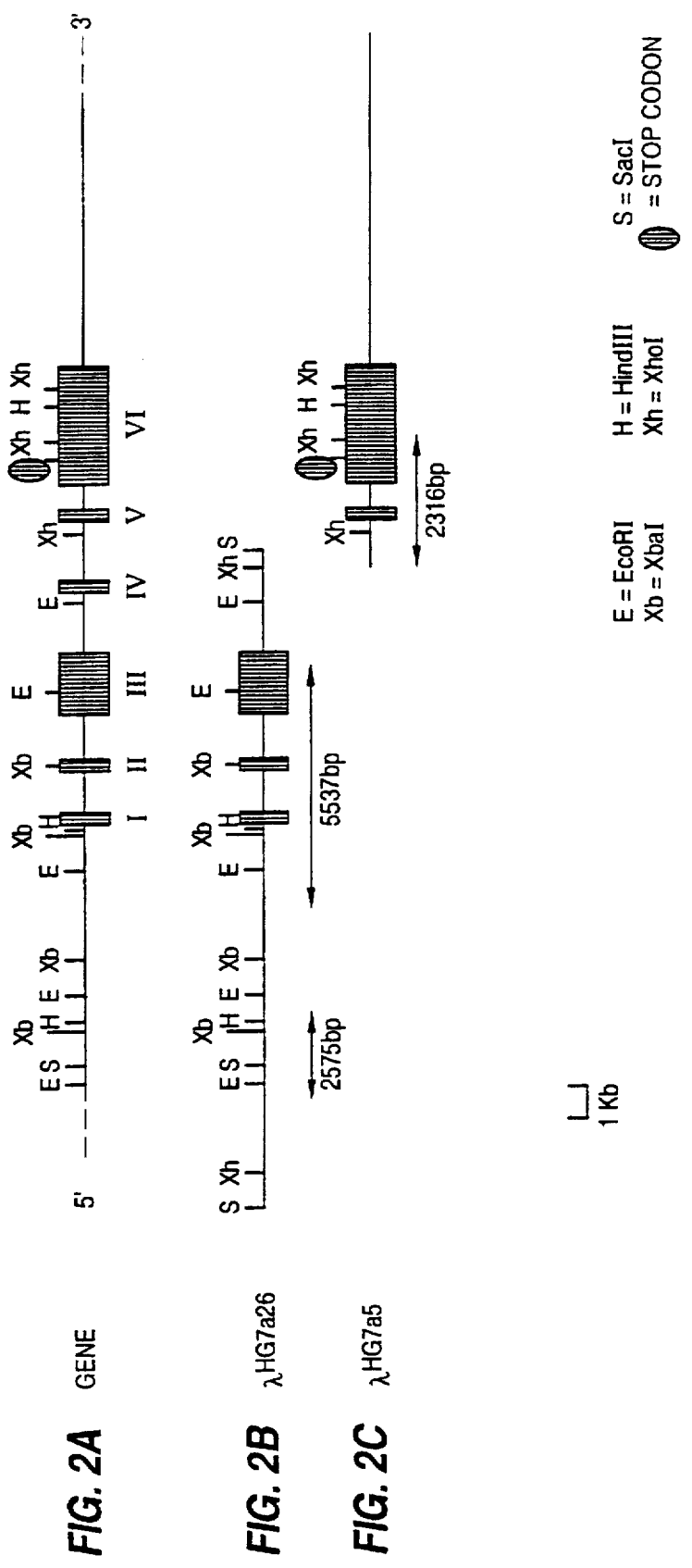
FIG. 4 shows an alignment of the proximal promoter regions of rat, human and hamster CYP7 genes (SEQ ID NOS 25, 27 and 26 respectfully). The following abbreviations are used: GRE, glucocorticoid response element; LFA1, liver factor 1; HRE, steroid/thyroid hormone response element; PPRE, peroxisome proliferator response element; TGT3, TGT3 element; and LFB1, liver factor B1. Transcription start sites "G" are indicated by a "*". Translation start codons "ATG" are underlined. The numbers indicate the nucleotide positions in each gene.

Another embodiment of the present invention provides a regulatory element of a CYP7 gene selected from the group comprising DNA fragments, from about −191 to about +64 of the rat CYP7 gene, from about −252 to about +3 of the hamster CYP7 gene and from about −187 to about +65 of the human CYT7 gene, and regulatory DNA fragments spanning a region within these fragments (subfragments), such as fragments shown in FIG. 4 (SEQ ID NOS 25, 26 and 27 respectfully).

Yet another advantageous regulatory element of the rat CYP7 gene is selected from the group of DNA fragments having regulatory activity and consisting of any of the eight fragments of DNA described in the first column of Table 1. The corresponding regulatory elements of hamster and human gene are closely homologous, as shown in FIG. 4 (SEQ ID NOS 25, 26 and 27 respectfully), and as listed in Table 1. Thus, an advantageous human CYP7 regulatory element is selected from the group consisting of any of the fragments of DNA described in the second column of Table 1 or human 7α-TRE, while an advantageous hamster CYP7 regulatory element is similarly selected from the group consisting of any of the eight fragments of column three of the Table 1. DNA fragments which begin at about the downstream nucleotides and end at about the upstream nucleotides as recited in Table 1 are also contemplated.

In addition to a regulatory element selected from the fragments described above (comprising from about −191 to about 64 (SEQ ID NO: 25) of the rat CYP7 gene, from about −252 to about 3 of the hamster CYP7 gene and from about −187 to about 65 of the human CYT7 gene, and fragments described in Table 1), it is contemplated that other substantially homologous sequences will have CYP7 regulatory activity and thus can be used as regulatory elements in accordance with this invention. Exemplary substantially homologous sequences include: substantially homologous sequences having at least about 80%, advantageously about 90% and more advantageously about 95% nucleotide sequence homology with respect to the described fragments; sequences having at least about 82%, and advantageously at least about 90%, homology between a pair of corresponding rat and hamster DNA sequences, such homology to the sequence from about −101 to about −29 of the rat CYP7 gene and the sequence from about −161 to about −86 of the hamster CYP7 gene, for example; and sequences having homology of at least about 71%, advantageously at least about 90%, between any pair of corresponding rat and human DNA sequences, for example, about −101 to about −29 of the rat CYP7 gene and the sequence from about −104 to about −30 of the human CYP7 gene.

TABLE 1

Regulatory elements of rat, human and hamster CYP7 gene

| I. Rat (from transcript. start site) | II. Human | III. Hamster (from start codon) |
|---|---|---|
| −101 to −29 | −104 to −30 | −161 to −86 |
| −81 to −37 | −78 to −36 | −136 to −92 |
| −161 to −127 | −159 to −124 | −208 to −184 |
| −149 to −131 | −147 to −128 | −206 to −188 |
| −171 to −154 | −169 to −152 | −228 to −211 |
| −101 to −82 | −104 to −79 | −161 to −137 |
| −73 to −56 | −71 to −54 | −128 to −111 |
| −86 to −71 | −89 to −68 | −146 to −126 |
| −160 to +32 | −158 to +32 | — |
| −224 to +32 | −223 to +32 | — |
| −3643 to +32 | −3643 to +32 | — |

Further embodiments of the present invention include a recombinant construct comprising at least one of the above-mentioned regulatory elements, advantageously a fragment disclosed in Table 1. Advantageously, for example, a regulatory element can be operably attached to a structural gene encoding CYP7, or to a reporter protein. Operably attached means that the regulatory element is positioned with respect to the structural gene such that it exerts control of the transcription of the structural gene.

A construct according to the invention can be provided in a vector capable of transforming a host cell. A host cell transformed or transfected with such a vector also comprises an embodiment of this invention, as well as a method for expressing a selected structural gene, advantageously CYP7 or a reporter gene, using host cells of this invention. Such a method of expression comprises the steps of culturing a host cell transformed with a recombinant DNA vector comprising a gene construct comprising at least one regulatory element operably attached to the selected structural gene, wherein culturing is performed in a medium that is suitable for accommodating the desired expression, and producing the gene product.

A reporter gene allows quantitative determination of gene expression in the presence of inhibitory or stimulatory compounds. A host cell transformed with a recombinant DNA vector comprising a gene construct of at least one regulatory element operably attached to the selected structural gene provides an expression system useful in a conventional method to screen a compound for its ability to inhibit or stimulate structural gene expression. Thus, an example of a screening method provides contacting the host cell with a test compound and detecting an inhibition or stimulation of gene expression. A test compound can comprise, for example, a physiological agent derived from substances endogenous to a human or, an exogenous compound.

Regulatory elements, advantageously those fragments identified in Table 1, are used to control expression of structural genes, such as the CYP7 gene, and various reporter or indicator genes. Reporter genes include, but are not limited to, *E. coli* β-galactosidase, galactokinase, interleukin 2, thymidine kinase, alkaline phosphatase, luciferase and chloramphenicol acetyltransferase (CAT). Those skilled in the art readily will recognize additional reporter genes.

A representative construct of regulatory element and reporter gene ("promoter/reporter construct") is made according to Example 2.6, which employs, for example, the rat regulatory element −101 to −29. Any of the other regulatory elements according to the invention, preferably those described in Table 1, can be substituted for that rat fragment −101 to −29, by using conventional genetic engineering methods.

According to the present invention, CYP7 constructs, such as the promoter/reporter construct, are transfected into a hepatoma cell line, advantageously, human hepatoma cell line HepG2. HepG2 liver cells express cholesterol 7α-hydroxylase normally, which makes these cells good candidates for the study of CYP7 regulation. Northern blots of normal HepG2 cells that were exposed to several bile acids, including tauro- or glyco-conjugates of cholate, deoxycholate, chenodeoxycholate or ursodeoxycholate, exhibited responsive changes in CYP7 mRNA levels as compared to non-responding control cell lines that were not exposed to those bile acids.

HepG2 cell lines are useful in screening methods provided according to the present invention. By observing expression of CYP7 in HepG2 cultures transiently transfected with CYP7 promoter/reporter gene constructs, the activity of a particular promoter region can be ascertained. Further, an agent can be added to the transfectant, and its effect on transcription can be ascertained readily.

More advantageously, a host HepG2 cell line according to the present invention that is transfected with promoter/reporter gene is both "confluent" and stable. Confluent cells are defined as cells that are at least about 4 days old, preferably 5 days, relative to the initiation of transfection. Confluent cell lines alternatively can be recognized by their uniform growth pattern, where cells tend to "adhere" to one another.

Preferably, stabilized HepG2 transfectants are employed in an assay according to the invention to provide more consistent results. A transfected cell line is stabilized using known methodology, as described by Dai et al., *Biochem.* 32:6928 (1993).

According to the present invention, it was discovered that the age of HepG2 transfectant cultures had a significant effect on the cells' response to steroid/thyroid hormones or bile acid conjugates. Both the endogenous cholesterol 7μ-hydroxylase mRNA and transcriptional activity of the CYP7 chimeric promoter/reporter gene constructs transiently transfected into HepG2 cells responded to hydrophobic bile acids in the adult phenotype only. Younger cells were much less responsive to hormones and produced no response to bile acids, possibly due to an underdeveloped or undeveloped bile acid transport system and/or an immature steroid hormone receptor system.

Results obtained by an assay method employing confluent HepG2 cells that were transiently transfected with rat promoter/reporter constructs according to the invention identified two regions in the CYP7 gene that are responsive to bile acid repression. One bile acid responsive element (BARE) is located in the highly conserved proximal region of the promoter, from nucleotide −160 to +36, while another BARE is located in the region between −224 to −3643.

The inventive regulatory elements are also useful for detecting and isolating a transcription factor of CYP7. To detect a transcription factor, a regulatory element according to the invention, advantageously an element from Table 1, is contacted with a biological sample suspected of containing a transcription factor. Binding between the fragment and a transcription factor and the step of isolating the transcription factor are accomplished by conventional methods.

For example, to isolate a transcription factor, the following steps can be employed. First, a footprinting assay is performed to determine whether a particular gene fragment, such as a regulatory element according to the invention, binds to a nuclear transcription factor. The footprinted sequence that is revealed is used to identify DNA-protein interactions by electrophoretic mobility assay (EMSA). If a band shift is detected in EMSA, the shifted sequence is confirmed by Southwestern blot. The Southwestern blot, by SDS-polyacrylamide gel electrophoresis separates nuclear proteins. A separated protein then is incubated with a shifted DNA sequence to identify a nuclear transcription factor. The DNA sequence then is used to screen an expression cDNA library for cDNA clones encoding a transcription factor. In an alternative method, a DNA fragment of the invention can be fixed to an affinity column and used to isolate a transcription factor present in nuclear extracts (See Example 2).

An identified transcription factor can be cloned and expressed in relatively high amounts and then employed in screening compounds for the ability to influence gene expression via the specific transcription factor. For example, the effect of a bile acid or its derivatives on the function of a BARP identified according to the invention is studied by a cotransfection assay. In this assay, a CYP7 promoter/luciferase construct according to the invention, advantageously pLUC-160 and an expression plasmid containing a BARP cDNA, are cotransfected into HepG2 cell cultures. Next, an investigator determines transcriptional activity of the chimeric gene constructs (by way of the reporter gene) in the presence of test agents or endogenous factors and in control cell lines. Additionally, HepG2 cells can be transfected with a BARP, so as to express it in high amounts. Then, EMSA and footprinting assays also are performed to study the activity of a BARP.

The following examples illustrate the invention and, as such, are not to be considered as limiting the invention set forth in the claims. Either human or hamster regulatory elements can be substituted for rat regulatory elements in the following examples.

EXAMPLE 1

CLONING AND NUCLEOTIDE SEQUENCING OF THE CYP7 GENES 1. (A) The Rat Gene

Figure 1:
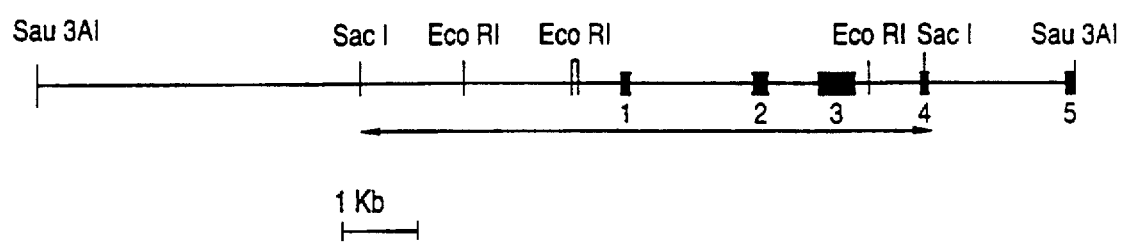
FIG. 1 illustrates the rat CYP7 gene map. Boxes indicate exons. The arrows indicate the region for which a nucleic acid sequence of clone R7αB24 (shown in FIGS. 8(A)–8(E)) now is determined.

A rat genomic library (Clontech, RL1022j) was screened with a rat cholesterol 7α-hydroxylase cDNA previously isolated by Li et al., *J. Biol. Chem.* 265, 12012–12019, (1990). After screening about 1 million plaque-forming units (pfu), a positive clone, λR7α2 was plaque-purified. This clone contains a 13 kb insert that spans 8 kb of the 5'-flanking region as well as the transcription region covering exons 1 through 3 and a partial exon 4 (FIG. 1). The nucleotide sequencing of an 8 kb (SEQ ID NO: 31) SacI fragment is shown in FIGS. 8(A)–8(E) and includes the 3643 bp 5'-flanking region and coding region from exon 1 to exon 4. This fragment includes about 2 kb of the 5'-upstream region, the sequence of which was published recently by the inventor (Chiang, et al., *Biochim. Biophys. Acta*, 1132, 337–339, 1992). Many putative regulatory elements, including liver-enriched hepatic nuclear factors (HNFs) binding sites, steroid/thyroid hormone response elements, and ubiquitous transcription factor binding motifs (NF1, OTF-1), were identified in this gene fragment.

It was shown previously that high cholesterol diet up-regulates transcription of the cholesterol 7α-hydroxylase gene, translation of CYP7 mRNA, and increases enzyme expression and activity in rat liver (Li, et al. *J. Biol. Chem.* 265, 12012–12019, 1990). It is especially noteworthy that steroid regulatory elements (SREs) similar to those found in the LDL receptor, HMG-CoA reductase, and HMG CoA synthase genes are located in the upstream region of the rat CYP7 gene promoter. These SREs are not present in the human or hamster CYP7 gene promoter. These SRE's are −1222-ATCCT<u>CTCCCCACT</u>CCCAAG <u>CATCCCTCCATG</u>-1191 (SEQ ID NO: 1), −1151-CAACTC <u>CTCCCCTATT</u>-1335 (SEQ ID NO: 2). Repeats 1 and 2 in the rat CYP7 gene are similar to the consensus SRE1 (CACC(C/G)(C/T)AC), which represses gene expression in the presence of oxysterols. The repeat 3 of the LDL receptor SRE has 11 bases identical to the sequence between −1151 to −1335 of the rat CYP7 gene. This sequence has been demonstrated to bind Sp1 which is a positive transcription factor in the LDL receptor gene (Dawson, et al. *J. Biol. Chem.* 263, 3372–3379, 1988).

1 (B) The Human Gene

A human genomic library, which had been constructed with Sau3A1 partially digested human placental DNA ligated into a BamHI site of the EMBL-3 Sp6/T7 phage vector (Clontech, Palo Alto, Calif.) was screened using a 1.6 kb EcoRI-PstI fragment of a human cholesterol 7α-hydroxylase cDNA isolated previously as a hybridization probe. Human CYP7 cDNA was isolated previously by Karam and Chiang, BBRC 185:588 (1992). Hybridizations were carried out at a high stringency condition of 68° C., 1% SDS and 0.1×SSC, 800,000 pfu of phages were screened. After four cycles of screening, seven positive clones were plaque-purified. Three clones comprising the largest inserts (λHGα26, λHGα5 and λHGα52) were isolated and analyzed by restriction mapping. FIG. 2A shows the complete gene map of human CYP7. Clone λHGα26 (FIG. 2B) contains a 15 kb insert which spans about 8.0 kb of the 5'-upstream flanking sequence and exons I to III (FIGS. 9 and 10 SEQ ID NOS 32 and 33). Clone λHGα5 (FIG. 2C) contains sequences from intron IV, exons V and VI to an 8.0 kb 3'-flanking sequence (FIG. 11 SEQ ID NO: 34).

Cloned bacteriophage λHG7α26 and λHG7α5 were deposited Aug. 25, 1993 at the American Type Culture Collection, ATCC, 12301 Parkland Drive, Rockville, Md. 20852, U.S.A., under accession numbers ATCC 75534 and 75535, respectively.

Five EcoRI fragments of the clone λHGα26 were excised from the phage DNA insert by restriction digestion and shotgun subcloned into the phagemid vector pBluescript II KS+ (Stratagene, La Jolla, Calif.). The clones were size-selected. EcoRI fragments were isolated from CsCl purified plasmids and used for sequencing. Nested deletions were generated by ExoIII/Mung Bean nuclease digestion according to the manufacturer's instruction (Stratagene, Calif.) using the conditions of a 37° C. incubation for 1 min intervals. This condition resulted in an average deletion of about 200 to 250 bp/min. DNA sequencing of the nested deletions was carried out by the dideoxy chain termination method using T7 sequence version 2.0 (USB, Cleveland, Ohio) and $^{35}$S-dATP. Sequence data were obtained from both strands and the overlapping deletion clones and analyzed using DNASIS software (Hitachi America, Calif.).

The nucleotide sequences of a 5.5 kb EcoRI fragment (FIG. 9 SEQ ID NO: 32) and a 2.6 kb EcoRI fragment (FIG. 10 SEQ ID NO: 33) were determined. The 5 kb fragment contains the sequence from −1886 of the 5'-upstream region to a partial exon 3 (FIG. 2B). Included in FIG. 9 (SEQ ID NO: 32) also is the 347 bp 3'-end sequence of a 3.5 Kb EcoRI fragment located immediately upstream of this 5.5 kb fragment (FIG. 2B). As shown in FIG. 2A, the 2.6 kb fragment is located further 5' upstream of the 3.5 kb EcoRI fragment. Thus, a 4823 bp 5'-upstream flanking region sequence of the gene now is determined.

Molowa et al. (*Biochem.* 31, 2539–2544, 1992) published a 1.7 kb upstream sequence of a human gene. A comparison of the sequence of the present invention to that of Molowa et al. in the overlapping region (1604 bp) revealed that sequences from the transcription start site to about −460 are identical, however, further upstream the sequence vary significantly. A total of 52 sequence discrepancies were found, which are far too many to attribute only to the presence of polymorphisms in the human gene. Cohen et al. (*Genomics*, 14, 153–161, 1992) reported a 723 bp upstream sequence and suggested sequencing errors by Molowa et al. Thus, the sequence of the present invention, from the transcription start site (nt+1) to −587, is identical to those reported previously by Molowa et al., Nishimoto et al., (*Biochem. Biophys. Acta*, 1122, 147–150, 1993) and Thompson et al., (*Biochim. Biophys. Acta.* 1168, 239–242, 1993).

The present invention identifies seven mismatches in Cohen's sequence from +1 to −123. A conversion of at T to C nucleotide −469 was identified to be a Mae II polymorphism (Thompson et al., 1993). The 5'-flanking sequence of the present invention agrees very well with that reported by Thompson et al. (1993). Only one mismatch at nucleotide −1193 (C vs A) was found in the overlapping region from +1 to nucleotide −2235.

Figure 3:
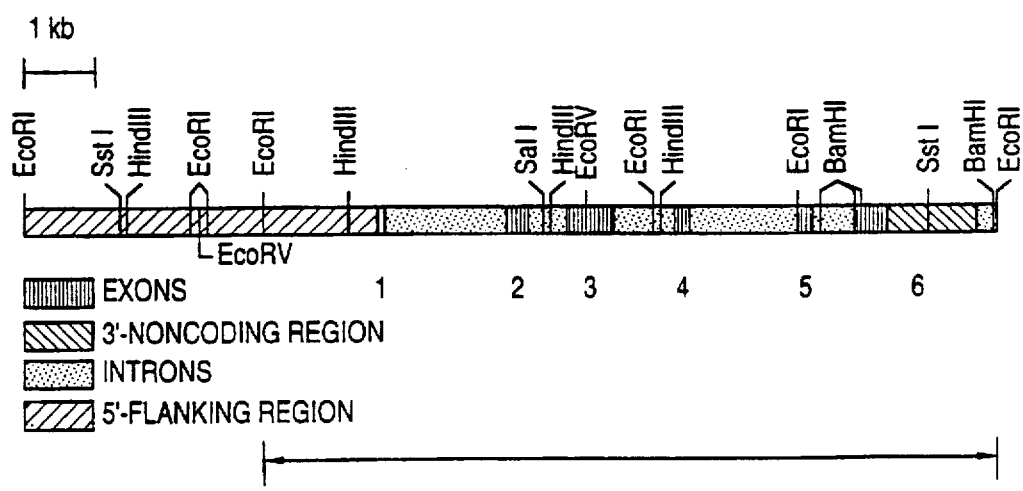
FIG. 3 illustrates the hamster CYP7 gene map. The arrows indicate the region for which a sequence (shown in FIG. 12 SEQ ID NO: 35) now is determined.

The present invention further identifies transcription factor binding motifs in the human gene, however, SRE-like sequences were not found in the human promoter region. 1. (C) The Hamster Gene A hamster liver genomic library constructed in the λDASH II vector (Stratagene) was screened with a 2.5 kb Eco RI fragment of the rat pBSK7α12 comprising the entire coding sequence of the rat cholesterol 7α-hydroxylase cDNA. About 1 million plaque-forming units were screened and one positive clone was identified and plaque-purified. The phage DNA was purified by CsCl gradient centrifugation and cDNA insert was restriction-mapped using rat probes (FIG. 3). EcoRI fragments of the DNA were isolated and subcloned into a pBluescript II KS+ vector. Nested deletions were generated with an ExoIII/Mung Bean deletion kit. The DNA sequences of these deletions were determined by the dideoxy chain termination method using Sequenase. In some instances 17-mer synthetic oligonucleotides were designed and used as sequencing primers.

Sequences were determined on both strands with overlaps. cDNA sequence analyses were carried out with DNASIS software.

FIG. 12 (SEQ ID NO: 35) shows the 11 kb DNA sequence of the hamster gene. It covers the sequence from nucleotide-1650 of the 5'-flanking region through all six exons and five introns (Exon I: nucleotide 1651–1730; Exon II: 3511–3650; Exon III: 4351–4937; Exon IV: 5945–6075; Exon V: 7690–7865; Exon VI: 8437–8736). The amino acid codons interrupted by introns are identical in each of these three homologous genes. The DNA sequence of the exon-intron junctions follows the canonical GT-AG rule typical of eukaryotic genes. The precise intron sizes determined by DNA sequencing are consistent with those of the rat. The intron 3 of the hamster gene is 1007 bp, which is about 1 kb shorter than that estimated for human intron 3. A putative polyadenylation signal (AATAAA) is located 371 bp upstream from the 3'-end of the gene, indicating that the isolated genomic clone should include the entire coding exon 6.

EXAMPLE 2

REGULATORY ELEMENTS AND TRANSCRIPTION FACTORS

Cloning of the CYP7 gene from three different species allows the analysis of the CYP7 gene structure and organization. Alignment and analysis of the highly conserved proximal promoter region of these homologous gene suggests that many regulatory elements are conserved and are likely to play important roles in gene regulation. Mapping of these transcription factor binding sites is essential to the isolation of transcription factors involving in the regulation of liver-specific CYP7 gene transcription. These sequence elements and protein factors are potential models for designing compounds and for screening for activators or repressors of the gene, such as described in a parent U.S. application Ser. No. 08/135,488, to Chiang, J. The following discussion relates to the regulatory elements and transcription factors of the rat gene promoter.

2.1. Alignment and Analysis of the CYP7 Genes

The proximal promoter regions of the rat, human and hamster genes were aligned. Sequence identity is about 82% between rat and hamster, 77% between hamster and human and 71% between human and rat (FIG. 4 SEQ ID NOS 25, 26 and 27 respectfully). Several liver-enriched transcription factors, HNF3, HNF4, HNF1 and C/EBP, and thyroid/steroid hormone response elements are highly conserved in these homologous genes (FIG. 5). Sequences that are further upstream of these genes have diverged considerably. In contrast to the report that the −400 proximal promoter of the human gene had no promoter activity (Molowa, et al. Biochem. 31, 2539–2544, 1992), this conservation indicates that the proximal promoter is important in transcriptional activation function and contains essential regulatory elements.

2.2. Footprint Analysis of the Rat Gene

DNase I hypersensitivity sites of the rat gene were mapped by digestion of rat liver nuclei (20 $OD_{260}$) with DNase I at 37° C. for time periods up to 4 minutes. DNA was isolated from nuclei at each time interval and digested with SacI, fractionated on a 0.8% agarose gel and transferred to nylon membranes. A 5'-probe of Sac I-EcoRI fragment (−3643 to −2265) was used for indirect end-labeling and was labeled with an activity of at least $1 \times 10^9$ CPM/µg. Four DNase I hypersensitivity sites (HSI, HSII, HSIII, HSIV) were mapped. HSI is mapped near a "CA" repeat region around nucleotide-1,500. HSII is located in the proximal promoter region. HSIII and HSIV are located in intron I and intron II, respectively (FIG. 6).

DNase I footprinting technique then was applied to map the transcription factor binding sites in the gene promoter (Heberlein,U, England, B and Tjian, R Cell, 41, 965–977, 1985). Transcription factor binding sites in the gene are protected from DNase I digestion. Two fragments were mapped: a Hind III-Xba I fragment (−346 to +36) in the proximal promoter region near the hypersensitivity site II and an upstream fragment Xba I-Hind III(−1530 to −1205) in the hypersensitivity site I. Probes were made from plasmid DNA digested with a restriction enzyme to generate a 5'-overhang, filled in with the Klenow fragment of DNA polymerase I and $^{32}$P-labeled dCTP, and then digested with a second restriction enzyme. Probes were purified from a native 5% polyacrylamide gel. Footprinting reactions included 2 µg of poly(dI-dC), 10% polyvinyl alcohol, 50 mM KCl and 20 fmol of probe in a volume of 50 µl. Reactions were stopped with EDTA and SDS, then phenol extracted, ethanol precipitated and run on polyacrylamide sequencing gels.

The footprinted areas are summarized as follows:

Footprints (FP) mapped in hypersensitivity site II:

FP I (Nucleotides −81 to −37): TGT3, 7α-TRE, HNF1/LFB1, CAAT, Box elements
5'-TGTTTGCTTTGGTCACTCAAGTTCAAGTTATT-GGATCATGGTCC-3' (SEQ ID NO: 3)

FP II (Nucleotides −149 to −131): HNF4/LFA1 element
5'-CTATGGACTTAGTTCAAGG-3' (SEQ ID NO: 4)

FP III (Nucleotides −171 to −154): GRE half site
5'-TGTTCTGGAGCCTCTTCT-3' (SEQ ID NO: 5)

Footprint mapped in hypersensitivity site I: FP IV (Nucleotides −1448 to −1410): NF1 elements
5'-TCACTGTGGCCTAGTGCCACATCTACCTATT-TCTTTGGCTTTAC- TTTGT-3' (SEQ ID NO: 6)

Footprint I covers a sequence from nucleotide −81 to −37 and consists of four elements: TGT3/HNF3, 7α-TRE, LFB1/HNF1, and CAAT box (reversed). Footprint II covers sequence from −149 to −131 and contains an LFA1/HNF4 site. Footprint III covers sequences from −171 to −154 and contains a consensus glucocorticoid response element (GRE) half site. In the hypersensitivity site I, a footprint covers −1554 to −1505 and contains a bipartite and a half-site of the NF1/CTF element. Most of these sequences are liver-enriched transcription factor consensus motifs and are highly conserved in all three species. It is especially interesting that Footprint I contains overlapping binding sites for at least four transcription factors, HNF3α/3β, 7α-TRE, HNF1/LFB1, and C/EBP. The TRE-like sequence (SEQ ID NO: 7) (TGGTCANNNNAGTTCA) located in the center of the cluster may be the binding site for Type II hormone receptors such as the $T_3$ receptor ($T_3R$), the retinoic acid receptor (RAR), the retinoid X receptor (RXR), the vitamin $D_3$ receptor ($VD_3R$), or the peroxisome proliferator activating receptor (PPAR) (Stunnenberg, HG, BioEssays, 15, 309–315, 1993). This gene fragment has been shown to be essential for major promoter activity and could confer taurocholate repression of promoter activity in rat primary hepatocyte cultures. It is likely that the element in footprint I identified in the present invention is a bile acid response element (BARE) of the CYP7 gene.

2.3. Gel Mobility Shift Analysis of the Rat Gene

The electrophoretic mobility shift assay (EMSA) is used to detect specific DNA-protein interactions in the identified footprints. Oligonucleotides corresponding to PPRE/TRE, 7αTRE, and TGT3 were synthesized and annealed to form double-stranded probes. DNA fragments corresponding to Footprints I, II, and IV were generated by PCR using primers that flank the footprint sequences. Probes are labeled with $^{32}$P dCTP by the Klenow fragment of DNA polymerase I. Probes were gel purified before use. Binding reactions were done in 20 µl comprising 10% glycerol, 10 mM HEPES, pH 7.9, 2 µg of poly(dI-dC), 1 µg of nuclear protein extracts and 20,000 CPM of probes at 30° C. for 15 min, followed by electrophoresis on 4% native polyacrylamide gels (Carthew, R. W., et al. Cell, 43, 439–448, 1985).

The footprint I probe shifted at least 4 bands when it was reacted with liver nuclear extract. Cold competitor specifically prevented band shifts. The footprint II probe shifted two bands whereas Footprint IV probe shifted only one band with liver nuclear extract. Since Footprint I contains several transcription factor binding elements and is the possible bile acid receptor or binding protein (BAR) binding site, double-stranded oligonucleotides were synthesized corresponding to the TGT3 and 7α-TRE elements in Footprint I.

EMSA revealed that the TGT3 element shifted two major bands, which may be due to the binding of HNF3α and HHF3β, whereas the 7α-TRE element shifted two different bands. Protein factors that bind to the 7α-TRE probe could be competed out with a 100-fold excess of its cold competitor or a rat growth hormone gene TRE element. However, TGT3 and PPAR/TRE oligonucleotides did not compete with the 7α-TRE probe. These results indicate that the 7α-TRE like element identified in the CYP7 gene promoter binds to one or two specific liver protein factors. In addition, the 7α-TRE of the human CYP7 gene (FIG. 4) also shifted one band in human liver nuclear extracts.

Furthermore, EMSA was performed using liver nuclear extracts isolated from rats treated with a diet supplemented with 0.25% deoxycholate, 1% cholate, 5% cholestyramine or 1% cholesterol for two weeks. Only nuclear extracts from deoxycholate-treated rat liver abolished the gel shift of the 7α-TRE oligonucleotide. Deoxycholate or sodium cholate treatment reduced both cholesterol 7α-hydroxylase activity and mRNA levels by 80% and 60%, respectively, whereas cholestyramine or cholesterol treatment stimulated these parameters by 330% and 180%, respectively.

These results suggested that deoxycholate may inhibit the binding or synthesis of a positive nuclear transcription factor, (i.e. factor A) to a bile acid responsive element (BARE) or inhibit the synthesis of factor A in nuclei as well as repress CYP7 gene expression. Alternatively, deoxycholate may bind to a negative regulator, BAR, which forms a complex with the positive factor A and prevents the binding of factor A with BARE. BAR and nuclear transcription factor A may compete for the same binding site, BARE. These factors are likely members of the steroid/thyroid hormone supergene family, since the recognition sequence is similar to the cognate response element. Interactions between this transcription BAR with adjacent liver-enriched transcription factors (HNF3α, HNF3β, HNF1, C/EBP) can affect the expression levels of the CYP7 gene.

2.3 (a) Effect of Bile Acids on EMSA: Further Results

A gel shift experiment was performed to further confirm that the 7αTRE and the $DR_0$ elements are bile acid responsive elements. Liver nuclear extracts isolated from rats treated with dietary supplements specified above were used. Deoxycholic acid and sodium cholate treatment significantly suppressed both cholesterol 7α-hydroxylase activity and mRNA levels by about 80% and 60%, respectively. On the other hand, 5% cholestyramine or 1% cholesterol stimulated activity and mRNA level by 330% and 180 respectively.

The rat 7αTRE element shifted one band in human nuclear extracts, while the human 7αTRE shifted one band in all rat nuclear extracts that were treated with cholestyramine, sodium cholate and cholesterol. In deoxycholate-treated rat liver nuclear extracts, however, human 7αTRE did not shift any protein band. All other nuclear extracts showed similar band patterns (no shift) as that of the control (non-treated rat) extracts. From the gel generated by this experiment, it was observed that 7αTRE shifted two bands whereas rat $DR_0$ shifted one. Thus, rat $DR_0$ element appeared to bind the transcription factor more specifically than did 7αTRE. Accordingly, the rat $DR_0$ element was selected for use as a probe to demonstrate the presence of transcription factor on a Southwestern blot, discussed below.

2.3 (b) Characterization of a DNA-Binding Protein

A Southwestern blot, which illuminates DNA-protein interactions, was performed to reveal nuclear protein factor (s) that bind to the rat $DR_0$ element, which appears to bind a transcription factor more specifically than 7α-TRE. This rat probe predominantly bound to a polypeptide of about 57,000 ±7000 Daltons which showed a similar band width in all rat liver nuclear extracts tested, including extracts from non-treated rats and rats treated with cholestyramine, sodium cholate, cholesterol and deoxycholate.

The rat $DR_0$ revealed a second band shift of 116,000 daltons in all of these extracts as well. This second shift is believed to constitute a dimer of two 57 KDa peptides. The 57 KDa polypeptide was also present in nuclear extracts of rat spleen, rat kidney and human liver, although the band was less pronounced in the human liver extracts.

Methods of substantially isolating transcription factors according to the invention, for example, can employ DNA fragments according to the invention in conjunction with methodology taught by Singh et al., Cell 52:415 (1988) and Kadonaga et al., PNAS USA 83:5889 (1986). Each of these publications is incorporated by reference herein in their entirety. Yet another approach to identify and clone genes for proteins that interact with DNA-binding protein employs yeast two-hybrid system to study protein-protein interaction (Fields and Song, 1989; Chien et al. PNAS 88:1958 (1991)). The Chien publication is incorporated by reference herein in its entirety.

2.4 Recognition site affinity chromatography

One approach to isolating a transcription factor provides the advantage of isolating a protein complex that includes both a DNA-binding protein and other associated protein factors that interact with the a DNA-binding protein. The success of purification of transcription factor is dependent, generally, on parameters including the quality of nuclear extracts, the amount of transcription factors present in the extracts, and the binding affinity of the DNA-affinity column. Also, the binding site sequence selected for use in the column is optimized by EMSA, DNase I footprinting, mutational analysis and by sequence comparison of homologous binding site.

A BARE consensus sequence, such as that identified by the present invention can be utilized advantageously in an affinity column. The rat or human 7αTRE or $DR_0$, which recognized a single binding protein in EMSA of either human or rat nuclear extracts, is suitable for DNA affinity column chromatography and identifies a 57 KDa bile acid responsive protein.

Affinity chromatography is performed according to the following protocol. First, cell-free nuclear extracts are obtained from either HepG2 cells or human liver tissues. Fresh human liver tissue is advantageous for isolating nuclear extracts, however, it sometimes difficult to obtain. Nuclear proteins are extracted with high salt and crude extracts are precipitated with ammonium sulfate, dialyzed and then subjected to gel filtration column (i.e., Sephacryl S-300, Pharmacia) or a heparin-agarose affinity column (Sigma Chemical). Column fractions are assayed for transcription factors by EMSA and pooled fractions are applied to a sequence-specific affinity column.

A DNA affinity column is prepared which employs double-stranded BARE consensus oligonucleotides according to the invention, which are provided with a 5' overhang of nucleotides "gatc". The oligonucleotides are concatemerized by phosphorylation with T4 polynucleotide kinase and ligated by T4 DNA ligase (Jackson et al., *GENE TRANSCRIPTION: A PRACTICAL APPROACH*, ed. Hames and Higgins, I.R.L. Press 189–242 (1993). The disclosure of the relevant section of this book concerning affinity chromatography methodology is expressly incorporated herein by reference in its entirety. The ligated, concatemerized DNA is covalently attached to a CNBr-activated Sepharose Cl2B gel (Pharmacia) (Kadonaga, 1986 supra)

A transcription factor preparation isolated by the column is subjected to SDS-polyacrylamide gel electrophoresis. Thereafter, the gel is stained with silver staining to demonstrate the preparation's purity, and the DNA-binding properties of the purified transcription factor measured using EMSA and DNase I footprinting.

Once a transcription factor is purified, it can be used to raise antibodies, which in turn are used as a screening probe to isolate cDNA clone encoding the transcription factor. For example, the purified 57 KDa BARP is used to raise antibodies against itself, which are used as a screening probe to isolate its cDNA. 2.4 (a) Screening using recognition-site sequences An alternate method of isolating a BARP includes directly cloning cDNAs encoding a BARP from human liver cDNA expression libraries (Promega, Clontech), which are screened for a fusion protein recognizing specific nucleotide sequences. This technique is perhaps simpler than affinity chromatography, but it yields cDNA(s) that encode a DNA-binding protein, not protein itself.

Binding site probes of a BARE consensus sequence according to the invention are prepared by 5'-end labelling a double-stranded oligonucleotide with $\gamma$-$^{32}$P ATP using T4 polynucleotide kinase. T4 DNA ligase is then used to concatamerize oligonucleotides. Human liver $\lambda$gt11 cDNA expression libraries will be screened following routine procedure described by Sambrook et al., *Mol. Cell Biol.* 9:946 (1989).

Fusion proteins are induced by overlaying the plates with IPTG-treated nitrocellulose filters and incubating for 6 hours at 37° C. Filters are soaked in 6M guanidinium chloride in binding buffer and washed in the same buffer but gradually reducing the concentration of denaturant to 0.188M, and finally in buffer without denaturant. Filters are placed in binding buffer, and blocked in non-fat mild solution and incubate with binding site probe at 4° C. overnight. Filters are washed and autoradiographed at −70° C.

Positive plaques are picked, replated and screened until plaque-purified. cDNA is sequenced by dideoxy chain termination method using Sequenase Kit (USB Co.) and analyzed with DNA analysis software. Amino acid coding sequences are analyzed for sequence motifs and compared against GenBank database for characteristics of DNA-binding proteins, such as possessed by a zinc finger, leucine zipper or member of a nuclear receptor gene family. 2.5 Characterizing transcription factors To overexpress a BARP for footprinting and transient transection assays, its cDNA is isolated according to the protocol of 2.3 (b) and subcloned into a pMT eukaryotic expression vector (Kaufman et al., 1989). For gel shift assay, cDNA will be subcloned into pGEM4 (Promega). Plasmid is linearized and in vitro transcribed by SP6 RNA polymerase. The resulting RNA is translated in a rabbit reticulocytes lysate system in the presence of $^{35}$S-methionine.

EMSA is performed as described herein. In vitro synthesized protein is incubated with $^{32}$P-labeled probe and electrophoresed in low ionic strength polyacrylamide gel. Two filters are placed against the dried gel, the first of which blocks the $^{35}$S radiation.

CYP7 promoter/luciferase constructs and pMT plasmid carrying a BARP cDNA are transiently cotransfected into HepG2 cells by calcium phosphate coprecipitation method as described previously. pRSV-βgal plasmid is used as an internal standard for normalization of transection efficiency. A test agent or endogenous factor is added in culture media and incubated for a period of time. Cells are lysed, then luciferase activity is measured, as described previously.

| Electrophoretic Mobility Shift Assay of DNA-protein Interactions | |
|---|---|
| Sequences of double-stranded probes | # of bands shifted |
| 1). FP I probe (−100 to −29): (SEQ ID NO:8)<br>5'-CTAGTAGGAGGACAAATAGTGTTTGCTTTGGTCACTCAAGTTCAAGTTATTGGATCATGGTCC-3'<br>GATCATCCTCCTGTTTATCACAAACGAAACCAGTGAGTTCAAGTTCAATAACCTAGTACCAGG-5'<br>3'- | four to five |
| 2) FP II probe (−161 to −127): (SEQ ID NO:9)<br>5'-CCTCTTCTGAGACTATGGACTTAGTTCAAGGCCGG-3'<br>3'-GGAGAAGACTCTGATACCTGAATCAAGTTCCGGCC-5' | two |
| 3). FP IV probe (−1454/−1394): (SEQ ID NO:10)<br>5'-TCACTGTGGCCTAGTGCCACATCTACCTATTTCTTTGGCTTTACTTTGTGCTAGGTGACC-3'<br>3'-AGTGACACCGGATCACGGTGTAGATGGATAAAGAAACCGAAATGAAACACGATCCACTGG-5' | one |
| 4). PPRE/TRE element probe (nt −101/−82):<br>5'-GAAGATCTAGTAGGAGGACAAATAG 3' (SEQ ID NO:11)<br>3' CATCCTCCTGTTTATCAC 5' (SEQ ID NO:12) | two |
| 5). 7α-TRE element probe (nt −73/−56 in FP I):<br>5'-GATCCTTGGTCACTCAAGTTC 3' (SEQ ID NO:13)<br>3' GAACCAGTGAGTTCAAGTTCCTAG 5' (SEQ ID NO:14) | two |
| 6). TGT3 element probe (nt −86/−71 in FP I):<br>5'-GATCCAATAGTGTTTGCTTTGGT 3' (SEQ ID NO:15)<br>3' TCACAAACGAAACCATCCTAG 5' (SEQ ID NO:16) | two |

2.6 Promoter/Reporter Gene Constructs

To determine the promoter sequences responsible for regulation of cholesterol 7α-hydroxylase, deletions of the rat CYP7 promoter were ligated upstream of the luciferase reporter gene (Luc). The promoter fragments were generated by the polymerase chain reaction using the primers listed with a rat CYP7 genomic clone as the template. The fragments were blunted by filling in with the Klenow fragment of DNA polymerase and then digested with Xho I. The fragments were then ligated into the pGL2-basic vector (Promega) which had been digested with SmaI and Xho I, and transformed into $E.\ coli$ HB101 cells. The resulting plasmids (pLUC-224, pLUC-160, pLUC-101, and pLUC-3600) are used to transfect primary hepatocytes or hepatoma cells for the study of luciferase gene expression under the control of the CYP7 promoter. The results show that pLUC-224 had two-fold higher luciferase activity than pLUC-160 and pLUC-3600 when transfected into rat primary hepatocytes. pLUC-3600 had transcription activity similar to that of pLUC-160. In addition, 50μM taurocholate inhibited the expression of luciferase activity in these hepatocytes, indicating that these CYP7 gene promoter fragments do contain a BARE, which confers bile acid regulation.

To determine if the sequence from −101 to −29 of the CYP7 gene promoter can function as an enhancer element, the region was cloned into the pGL2-Promoter vector (Promega). The vector is similar to pGL2-basic, with the addition of the SV40 early promoter between the multiple cloning site and the luc gene. The rat sequence was amplified by the polymerase chain reaction to flank the sequence with a BamHI site and a BglII. The fragment was ligated in both orientations to the pGL2-Promoter, which had been cleaved with BglII. The resulting plasmids are named pLUC-101/-29 and pLUC-29/-101.

Chloramphenicol acetyltransferase (CAT) reporter gene constructs were made by using the polymerase chain reaction and primers to amplify the region −415 to +36 of the rat CYP7 gene and to incorporate an XbaI at nucleotide +36. The blunt ended, Xba I digested fragment was ligated into a promoter-less pCAT basic vector (Promega) which had been digested with Sal I, blunt-ended and digested with Xba I to yield -415CAT. A longer construct named -3643CAT was made by digesting -415CAT with Hind III and inserting a 3.2 kb Sac I-Hind III genomic fragment. The 3.6 kb insert was removed from -3643CAT and ligated into a pGL2-basic vector (Promega). This plasmid was used to generate nested deletions with Exo III and S1 nuclease.

---

Promoter/Reporter Gene Constructs
PCR primers used for PCR of fragments

+30
L1: 5'-AGATGG<u>CTCGAG</u>ACTCTTTGCCTAGCAAA-3' (SEQ ID NO:17)
        XhoI

−224
L3: 5'-CAGCACATGAGGGACAG03' (SEQ ID NO:18)

−160
L4: 5'-CTCTTCTGAGACTATGGAC-3' (SEQ ID NO:19)

−101
L8: 5'-GA<u>AGATCT</u>AGTAGGAGGACAAATAG-3' (SEQ ID NO:20
    BglII

Sequence of promoter fragments inserted in pGL2-basic vector pLUC-224:    5'-CAGCACATGAGGGACAGACCTTCAGCTTATCGAGTATTGCAGCTCTCTGTTT
GTTCTGGAGCCTCTTCTGAGACTATGGACTTAGTTCAAGGCCGGGTAATGCTATT
TTTTTCTTCTTTTTTCTAGTAGGAGGAGGACAAATAGTGTTTGCTTTGGT
CACTCAAGTTCAAGTTATTGGATCATGGTCCTGTGCACATATAAAGTCTAGTCAGA
CCCACTGTTTCGGGACAGCCTTGCTTTGCTAGGCAGGCAAAGAGT<u>CTCGAG</u>-3' (SEQ ID NO:21)
                                                                                                                                          XhoI pLUC-160:    5'-CTCTTCTGAGACTATGGACTTAGTTCAAGGCCGGGTAATGCTATTTTTTTCT
TCTTTTTTCTAGTAGGAGGACAAATAGTGTTTGCTTTGGTCACTCAAGTTCA
AGTTATTGGATCATGGTCCTGTGCACATATAAAGTCTAGTCAGACCCACT
GTTTCGGGACAGCCTTGCTTTGCTAGGCAGGCAAAGAGT<u>CTCGAG</u>-3' (SEQ ID NO:22)
                                                                                                                                                         XhoI pLUC-101    5'-GAAGATCTAGTAGGAGGACAAATAGTGTTTGCTTTGGTCACTCAAGTTCA
AGTTATTGGATCATGGTCCTGTGCACATATAAAGTCTAGTCAGACCCACT
GTTTCGGGACAGCCTTGCTTTGCTAGGCAGGCAAAGAGT<u>CTCGAG</u>-3' (SEQ ID NO:23)
                                                                                                               XhoI pLUC-3600:    3.6 kb 5' flanking sequence to +36

Sequences of promoter fragments inserted in pGL2-promoter vector:

pLuc-1010/-29:    −101
GAAGATCTAGTAGGAGGACAAATAGTGTTTGATTTGGTCACTCAAGTTC
−29
AAGTTATTGGATCATGGTCCTGTGCACAT<u>CCTAGGGC</u>-3' (SEQ ID NO:24)

pLuc-29/-101:    Reversed direction of the above sequence

Promoter/CAT gene constructs:

-415CAT:    sequence from -415 to +36
-3643CAT:    3.6 kb 5'-upstream sequence to +36

---

EXAMPLE 3

HepG2 CELLS TRANSFECTED WITH PROMOTER/REPORTER GENE CONSTRUCTS 3.1 HepG2 cell cultures HepG2 cells were obtained from ATCC (Bethesda, Md.) and grown in Dulbecco's Modified Eagles Medium/F12 (50:50) supplemented with 10% heat inactivated fetal bovine serum, 1 mM Minimum Essential Medium (MEM) sodium pyruvate, 1×MEM non-essential amino acids, 25 mM Hepes, 100 U/ml penicillin G and 100 mg/ml streptomycin in a humidified incubator with 5% $CO_2$ in air at 37° C. Forty-eight hours prior to the isolation of RNA, the media were replaced with fresh media containing bile salts but without fetal calf serum. The monolayers were grown to either subconfluent (50 to 70% confluent) or confluent. Viability of the cells was checked by Trypan Blue exclusion test. About 40 million cells were lysed by the addition of 4M guanidinium thiocyanate, 0.5% N-lauroylsarcosine, 25 mM sodium citrate, pH 7.0, and 0.1M 2-mercaptoethanol, phenol extracted, and ethanol precipitated. Poly (A+) RNA was isolated using PolyAT tract mRNA isolation system III according to the manufacturer's instructions (Promega, Madison, Wis.). A PstI fragment of human cholesterol 7α-hydroxylase cDNA was labeled with $^{32}$P and used as a hybridization probe, according to the method of Karam et al., *Biochem. Biophys. Res. Commun.* 185:588 (1992). Human actin cDNA was used to hybridize the same membrane and served as an internal standard for the normalization of RNA level which were quantitated by scanning each lane with a laser scanner.

For transient transfection assay, cells were split and plated for at a density of $10^6$ cells/60 mm Petri dish and grown to subconfluence (about 30% confluence) or to confluence.

3.2 Clarifications concerning the rat CYP7 promoter/reporter gene constructs utilized Constructs pLUC-3600, pLUC-224, and pLUC-160 were constructed according to the description in section 2.4 above, with the following minor corrections to their nomenclature noted for the sake of exactness. First, as shown in the sequences listed above, the promoter sequences of all three constructs share the common endpoint, nucleotide +32 of the CYP7 DNA sequence, as opposed to nucleotide +36. The latter 4 nucleotides upstream of +32 include non-CYP7 bases that are a part of the exogenously-added Xho splice site. Second, as stated above, construct pLUC-3600 comprises a fragment encompassing the entire 3643 kilobase promoter region up until +32 of CYP7 gene. Accordingly this construct known figuratively as pLUC-3600 denotes a construct that contains a fragment between −3643 and +32 of CYP7.

Accordingly, three chimeric gene constructs, pLUC-3600, pLUC-224, and pLUC-160, represent deletion mutants generated by PCR using primers or by restriction digestion as described herein above. These three constructs were used for transient transfection assays in HepG2 cells.

3.3 Characterization of cholesterol 7α-hydroxylase mRNA in HepG2 cells

HepG2 liver cells express cholesterol 7α-hydroxylase normally, which makes these cells good candidates for the study of CYP7 regulation. To assess the suitability of these cell lines suitable for use in a transfection assay of the CYP7/reporter chimeric gene constructs, it was necessary to prove first that cholesterol 7α-hydroxylase activity could be regulated in these cells.

To characterize HepG2 cells, expression of cholesterol 7α-hydroxylase mRNA was measured in HepG2 control cells and cells treated with bile acids. Northern blot hybridization of poly (A+) RNAs isolated from confluent cultures of HepG2 cells, that were treated with media containing 100 μM of tauro- (T) or glyco- (G) conjugate of cholate (CA), deoxycholate (DCA), chenodeoxycholate (CDCA) or ursodeoxycholate (UDCA) and incubated. Cholesterol 7α-hydroxylase cDNA hybridized to two mRNA species of 3 kb and 1.8 kb, in agreement with Hassan et al., *Biochem. Pharmacol.* 44:1475 (1992). Both of these RNA species apparently are 7α-hydroxylase mRNA because the two bands changed responsively in parallel.

In subconfluent cultures, only TCDCA could repress mRNA level. In contrast, tauroursodeoxycholate (TUDCA) significantly increased mRNA level in subconfluent HepG2 cells. Glyco-conjugates of bile acids had similar effects as the tauro-conjugates. At this concentration, bile acid did not reduce viability of HepG2 cells.

FIG. 13 summarizes the effects of bile acid conjugates on 7α-hydroxylase mRNA level in HepG2 cells. When 100 μM taurocholate (TCA) was added, mRNA level was not changed significantly, while TDCA and TCDCA reduced mRNA level by 50 to 80% in confluent cultures. mRNA levels are expressed as % of mRNA level in cells without treatment of bile acids. Values are averages of three experiments. Thus, cholesterol 7α-hydroxylase mRNA level in HepG2 cells is regulated by bile acids. The inhibitory effect of bile acids follows the hydrophobicity indexes of bile acids, TCA<TDCA<TCDCA, as described by Heuman et al., *Lipid Res.* 30:1160 (1989). The results are also consistent with those observed in primary cultures of rat hepatocytes, as described by Hylemon et al., *J. Biol. Chem.* 267:16866 (1992).

3.4 Transient Transfection of HepG2 cells with rat CYP7 promoter/reporter constructs CYP7 promoter/reporter constructs were transiently transfected into HepG2 cells using the calcium phosphate-DNA coprecipitation method, with 0.5 ml of coprecipitate containing 5 μg of test plasmid (pLUC-3600, pLUC-224, and pLUC-160) and 1 μg of β-galactosidase expression plasmid, pCMVβ (Clontech), as an internal standard for transfection efficiency. After 4 hours, cells were shocked with 15% glycerol in TBS for 90 seconds, washed three times with TBS and further incubated for 42 hours in serum free medium containing 200 μM tauro-conjugates of bile acids. Cells were washed twice with phosphate-buffered saline, lysed and harvested with 400 μl of reporter lysis buffer (Promega) according to manufacturer's instruction.

Luciferase activity was assayed by mixing 20 μl of cell extracts to 100 μl of luciferase assay reagent (Promega) at room temperature and measuring light emission during the initial 10 seconds of the reaction. A luminometer (Lumat LB9501, Berthold) was used for this purpose. Luciferase activity was corrected for transfection efficiency.

3.5 Results: Transcriptional activity of CYP7 promoter/reporter constructs in HepG2 cultures The promoter/reporter chimeric gene constructs according to the invention were transiently transfected into HepG2 cells to demonstrate the effect of bile acids on transcriptional activity. The untreated cells shown in FIG. 14 reveal that promoter activity of pLUC-224 was much higher than pLUC-3600, and pLUC-160. Enhancer activity therefore is believed to be located between nucleotides −224 and −160. In addition, a repressor is believed to be located upstream of nucleotide −224, between nucleotides −224 and −3643.

The hormone response elements are likely located upstream of nucleotide −224, according to the following experiment. Addition of 1 μM thyroid hormone, $T_4$ and 0.1 μM dexamethasone increased transcriptional activity of pLUC-3600 by 2.5-fold in confluent cultures. However, this same amount of thyroid hormone and dexamethasone decreased the activity of pLUC-160 by 40% in subconfluent cultures, and had little effect on pLUC-224. Luciferase activity in each transfection experiment was expressed as % of activity in cells transfected with pGL2-control plasmid.

Figure 15:
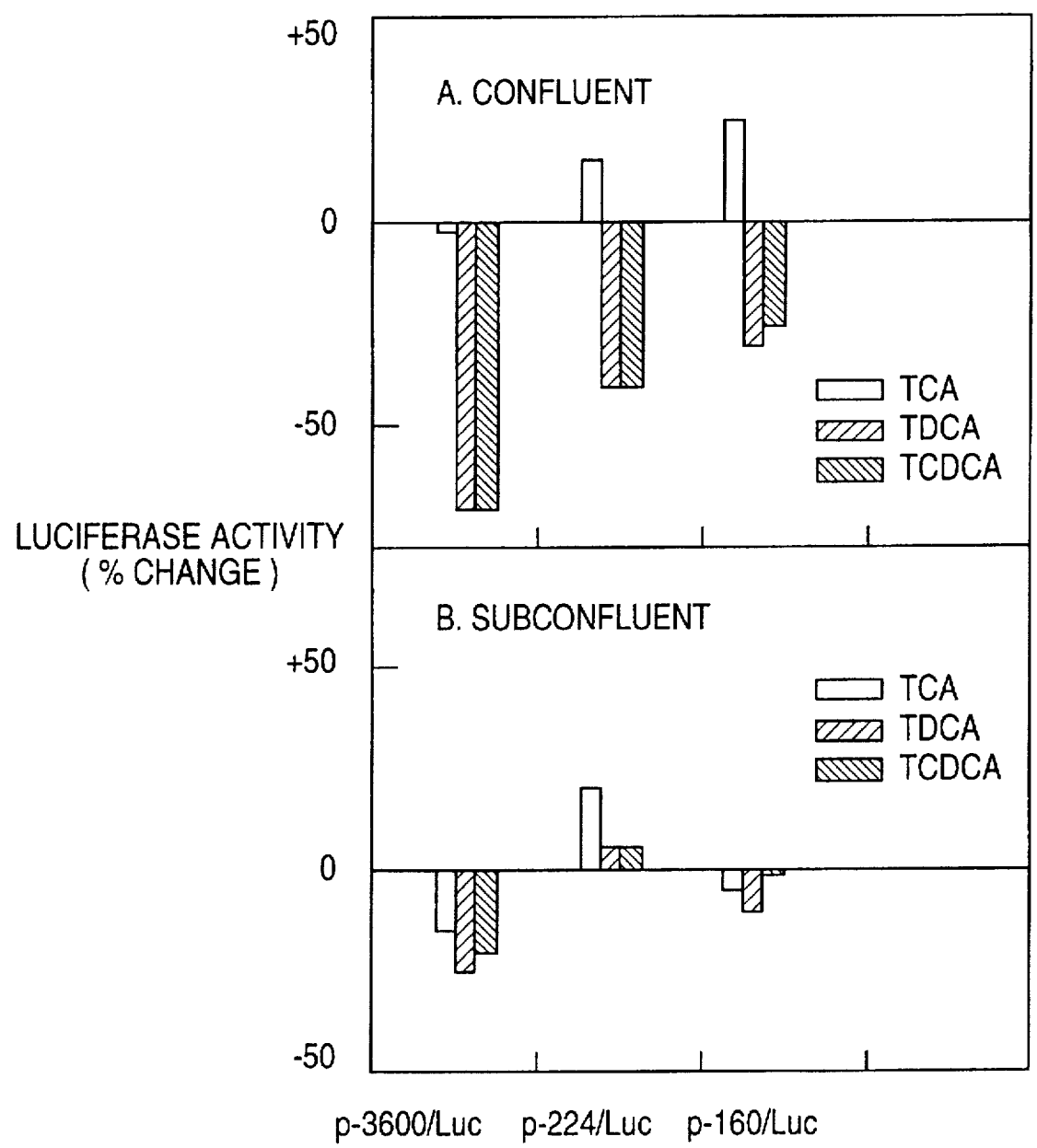
FIG. 15 shows the effect of bile acids on transcriptional activity of CYP7/LUC constructs transiently transfected into cultures of confluent (A) or subconfluent (B) HepG2 cells, as described in Example 3.5.

That bile acid response elements are located in the proximal promoter region, nucleotides −160 to +32, and also in region upstream of nucleotide −224 was revealed by the following experiment. Addition of 200 μM TCA, TDCA or TCDCA did not affect transcriptional activity of the promoter/reporter constructs transfected into subconfluent HepG2 cultures, as shown in FIG. 15B. Luciferase activity in transfected cells was expressed as % of activity in transfected cells without treatment with bile acids. However, in the confluent cells, TDCA and TCDCA repressed transcriptional activity of p-pLUC-3600 by more than 70% and repressed activity of pLUC-224, or pLUC-160 by up to 45% (FIG. 15A). TCA, however, did not affect transcriptional activities of these gene constructs in HepG2 cultures.

It will be apparent to those skilled in the art that various modifications and variations can be made to the compositions of matter and processes of this invention. In particular, various kinds of screening assays are encompassed that employ human CYP7 regulatory elements or its analogs. Thus, it is intended that the present invention cover the modifications and variations provided they fall within the scope of the appended claims and their equivalents.

All references to publications set forth above are expressly incorporated by reference in their entirety herein.

What is claimed is:

1. A culture of HepG2 cells transfected with CYP7 DNA that is regulatory with respect to CYP7 expression in the presence of bile acids, wherein (a) said culture is confluent, and (b) said culture is responsive to the presence of bile acids.

2. A culture according to claim 1, wherein said culture is matured to at least about 4 days prior to initiation of transfection.

3. A culture according to claim 1, wherein said CYP7 DNA comprises a fragment of human CYP7 from a region between about −223 to about +32, measured relative to the transcription start site, +1.

4. A culture according to claim 3, wherein said human CYP7 DNA fragment is selected from DNA fragments in the group consisting of from about −104 to about −30, from about −78 to about −36, from about −159 to about −124, from about −147 to about −128, from about −169 to about −152, from about −104 to about −79, from about −71 to about −54 and from about −89 to about −68, measured relative to the transcription start site, +1.

5. A culture according to claim 1, wherein the CYP7 DNA comprises a fragment of rat CYP7 from a region between about −224 to about +32, measured relative to the transcription start site, +1.

6. A culture according to claim 1, wherein said cells are transfected with a construct comprising said CYP7 DNA and a reporter molecule that is capable of indicating regulatory activity of said CYP7 DNA.

7. A culture according to claim 6, wherein said reporter molecule is non-CYP7 DNA.

8. A culture according to claim 7, wherein said non-CYP7 DNA encodes luciferase.

9. A method for determining an agent's effect on CYP7 DNA comprising the steps of:

(a) bringing into contact with an agent, a culture of HepG2 cells transfected with CYP7 DNA that is regulatory with respect to bile acids, wherein (i) said culture is confluent, and (ii) said culture is responsive to the presence of bile acids, and (b) determining whether said agent inhibits or stimulates the regulatory activity of said CYP7 DNA.

10. A method according to claim 9, wherein said culture is matured for at least about 4 days prior to the initiation of transfection.

11. A method according to claim 9, wherein said CYP7 DNA comprises a fragment of human CYP7 from a region between about −223 to about +32, measured relative to the transcription start site, +1.

12. A method according to claim 11, wherein said human CYP7 DNA fragment is selected from DNA fragments in the group consisting of from about −104 to about −30, from about −78 to about −36, from about −159 to about −124, from about −147 to about −128, from about −169 to about −152, from about −104 to about −79, from about −71 to about −54 and from about −89 to about −68, measured relative to the transcription start site, +1.

13. A method according to claim 9, wherein the CYP7 DNA comprises a fragment of rat CYP7 from a region between about −224 to about +32, measured relative to the transcription start site, +1.

14. A method according to claim 9, wherein in step (a), a reporter molecule is operatively linked to said CYP7 DNA, and wherein in step (b) said determining comprises monitoring the expression of said reporter molecule.

15. A method according to claim 14, wherein said reporter molecule is non-CYP7 DNA that is operatively linked to said CYP7 DNA, and wherein said determining comprises monitoring the expression of a protein encoded by said non-CYP7 DNA.

16. A method according to claim 15, wherein said non-CYP7 DNA encodes the protein luciferase.

17. A method according to claim 9, wherein said agent is a physiological agent endogenous to a human.

18. A method according to claim 9, wherein said agent is an agent exogenous to a human.

19. A method of obtaining a culture of HepG2 cells responsive to the presence of bile acids, comprising:

(a) transfecting a culture of HepG2 cells with CYP7 DNA having a bile acid responsive element; and (b) culturing said culture to substantially complete confluency such that said culture is capable of responding to the presence of bile acids.

20. A method according to claim 19, wherein said culture is matured to at least about 4 days prior to initiation of transfection.

21. A method according to claim 19, wherein said CYP7 DNA comprises a fragment of human CYP7 from a region between about −223 to about +32, measured relative to the transcription start site, +1.

22. A method according to claim 21, wherein said human CYP7 DNA fragment is selected from DNA fragments in the group consisting of from about −104 to about −30, from about −78 to about −36, from about −159 to about −124, from about −147 to about −128, from about −169 to about −152, from about −104 to about −79, from about −71 to about −54 and from about −89 to about −68, measured relative to the transcription start site, +1.

23. A method according to claim 19, wherein the CYP7 DNA comprises a fragment of rat CYP7 from a region between about −224 to about +32, measured relative to the transcription start site, +1.

24. A method according to claim 19, wherein said cells are transfected with a construct comprising said CYP7 DNA and a reporter molecule that is capable of indicating regulatory activity of said CYP7 DNA.

25. A method according to claim 24, wherein said reporter molecule is non-CYP7 DNA.

26. A culture according to claim 25, wherein said non-CYP7 DNA encodes luciferase.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATCCTCTCCC CACTCCCAAG CATCCCTCCA TG        32

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAACTCCTCC CCTATT        16

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGTTTGCTTT GGTCACTCAA GTTCAAGTTA TTGGATCATG GTCC        44

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTATGGACTT AGTTCAAGG        19

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
TGTTCTGGAG CCTCTTCT                                                      18
```

( 2 ) INFORMATION FOR SEQ ID NO:6:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
TCACTGTGGC CTAGTGCCAC ATCTACCTAT TTCTTTGGCT TTACTTTGT                    49
```

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
TGGTCANNNN AGTTCA                                                        16
```

( 2 ) INFORMATION FOR SEQ ID NO:8:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

```
CTAGTAGGAG GACAAATAGT GTTTGCTTTG GTCACTCAAG TTCAAGTTAT TGGATCATGG        60

TCC                                                                      63
```

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

```
CCTCTTCTGA GACTATGGAC TTAGTTCAAG GCCGG                                   35
```

( 2 ) INFORMATION FOR SEQ ID NO:10:

( i ) SEQUENCE CHARACTERISTICS:

(A) LENGTH: 60 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:10:

TCACTGTGGC CTAGTGCCAC ATCTACCTAT TTCTTTGGCT TTACTTTGTG CTAGGTGACC  60

(2) INFORMATION FOR SEQ ID NO:11:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GAAGATCTAG TAGGAGGACA AATAG  25

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:12:

CACTATTTGT CCTCCTAC  18

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GATCCTTGGT CACTCAAGTT C  21

(2) INFORMATION FOR SEQ ID NO:14:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:14:

GATCCTTGAA CTTGAGTGAC CAAG  24

(2) INFORMATION FOR SEQ ID NO:15:

(i) SEQUENCE CHARACTERISTICS:
(A) LENGTH: 23 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

GATCCAATAG TGTTTGCTTT GGT    23

(2) INFORMATION FOR SEQ ID NO:16:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:16:

GATCCTACCA AAGCAAACAC T    21

(2) INFORMATION FOR SEQ ID NO:17:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

AGATGGCTCG AGACTCTTTG CCTAGCAAA    29

(2) INFORMATION FOR SEQ ID NO:18:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

CAGCACATGA GGGACAG    17

(2) INFORMATION FOR SEQ ID NO:19:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

CTCTTCTGAG ACTATGGAC    19

(2) INFORMATION FOR SEQ ID NO:20:

(i) SEQUENCE CHARACTERISTICS:
(A) LENGTH: 25 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:20:

| | | | |
|---|---|---|---|
| GAAGATCTAG TAGGAGGACA AATAG | | | 25 |

( 2 ) INFORMATION FOR SEQ ID NO:21:

( i ) SEQUENCE CHARACTERISTICS:
        ( A ) LENGTH: 264 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
CAGCACATGA GGGACAGACC TTCAGCTTAT CGAGTATTGC AGCTCTCTGT TTGTTCTGGA      60
GCCTCTTCTG AGACTATGGA CTTAGTTCAA GGCCGGGTAA TGCTATTTTT TTCTTCTTTT     120
TTCTAGTAGG AGGAGGACAA ATAGTGTTTG CTTTGGTCAC TCAAGTTCAA GTTATTGGAT     180
CATGGTCCTG TGCACATATA AAGTCTAGTC AGACCCACTG TTTCGGGACA GCCTTGCTTT     240
GCTAGGCAGG CAAAGAGTCT CGAG                                            264
```

( 2 ) INFORMATION FOR SEQ ID NO:22:

( i ) SEQUENCE CHARACTERISTICS:
        ( A ) LENGTH: 199 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
CTCTTCTGAG ACTATGGACT TAGTTCAAGG CCGGGTAATG CTATTTTTT CTTCTTTTT       60
CTAGTAGGAG GACAAATAGT GTTTGCTTTG GTCACTCAAG TTCAAGTTAT TGGATCATGG    120
TCCTGTGCAC ATATAAAGTC TAGTCAGACC CACTGTTTCG GACAGCCTT GCTTTGCTAG     180
GCAGGCAAAG AGTCTCGAG                                                 199
```

( 2 ) INFORMATION FOR SEQ ID NO:23:

( i ) SEQUENCE CHARACTERISTICS:
        ( A ) LENGTH: 145 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
GAAGATCTAG TAGGAGGACA AATAGTGTTT GCTTTGGTCA CTCAAGTTCA AGTTATTGGA     60
TCATGGTCCT GTGCACATAT AAAGTCTAGT CAGACCCACT GTTTCGGGAC AGCCTTGCTT    120
TGCTAGGCAG GCAAAGAGTC TCGAG                                          145
```

( 2 ) INFORMATION FOR SEQ ID NO:24:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GAAGATCTAG TAGGAGGACA AATAGTGTTT GATTGGTCA CTCAAGTTCA AGTTATTGGA    60

TCATGGTCCT GTGCACATCC TAGGGC    86

( 2 ) INFORMATION FOR SEQ ID NO:25:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GAGTATTGCA GCTCTCTGTT TGTTCTGGAG CCTCTTCTGA GACTATGGAC TTAGTTCAAG    60

GCCGGGTAAT GCTATTTTTT TCTTCTTTTT TCTAGTAGGA GGACAAATAG TGTTTGCTTT    120

GGTCACTCAA GTTCAAGTTA TTGGATCATG GTCCTGTGCA CATATAAAGT CTAGTCAGAC    180

CCACTGTTTC GGGACAGCCT TGCTTTGCTA GGCAAAGAGT CTCCCCTTTG GAAATTTTCC    240

TGCTTTTGCA AAATG    255

( 2 ) INFORMATION FOR SEQ ID NO:26:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TATCAAGTAT TGAAGCTCTC TGCTTGTTTT GGAGCCTCTT CTGATACTAT GGACTTAGTT    60

CAAGGCTGGG CAATACTATT TTTTCTTTT TTCTAATAGG AGGACAAATA GTTAGTTGTT    120

TGCTTTGGTC ATCCAAGTTC AAGTTATTGG ATCATGGTCC TATGTGTATA AAGAGTCTAG    180

TTTGAGCCTT TCAGGGGCAG CCTTGCTGGC TAAGCACAGA CTCTCCTCTT GGGAGTTTTC    240

CTGCTTTGCA AAATG    255

( 2 ) INFORMATION FOR SEQ ID NO:27:

( i ) SEQUENCE CHARACTERISTICS:
        ( A ) LENGTH: 254 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GTATTGCAGG TCTCTGATTG CTTTGGAACC ACTTCTGATA CCTGTGGACT TAGTTCAAGG    60

CCAGTTACTA CCACTTTTTT TTTTCTAATA GAATGAACAA ATGGCTAATT GTTTGCTTTG    120

TCAACCAAGC TCAAGTTAAT GGATCTGGTA CTATGTATAT AAAAAGCCTA GCTTGAGTCT    180

CTTTTCAGTG GCATCCTTCC CTTTCTAATC AGAGATTTTC TTCCTCAGAG ATTTGGCCT    240

AGATTTGCAA AATG    254

( 2 ) INFORMATION FOR SEQ ID NO:28:

( i ) SEQUENCE CHARACTERISTICS:

( A ) LENGTH: 504 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

```
Met Met Thr Thr Ser Leu Ile Trp Gly Ile Ala Ile Ala Ala Cys Cys
1               5                   10                  15
Cys Leu Trp Leu Ile Leu Gly Ile Arg Arg Gln Thr Gly Glu Pro
            20                  25                  30
Pro Leu Glu Asn Gly Leu Ile Pro Tyr Leu Gly Cys Ala Leu Gln Phe
            35                  40                  45
Gly Ala Asn Pro Leu Glu Phe Leu Arg Ala Asn Gln Arg Lys His Gly
        50                  55                  60
His Val Phe Thr Cys Lys Leu Met Gly Lys Tyr Val His Phe Ile Thr
65                  70                  75                  80
Asn Pro Leu Ser Tyr His Lys Val Leu Cys His Gly Lys Tyr Phe Asp
                85                  90                  95
Trp Lys Lys Phe His Phe Ala Thr Ser Ala Lys Ala Phe Gly His Arg
                100                 105                 110
Ser Ile Asp Pro Met Asp Gly Asn Thr Thr Glu Asn Ile Asn Asp Thr
        115                 120                 125
Phe Ile Lys Thr Leu Gln Gly His Ala Leu Asn Ser Leu Thr Glu Ser
130                 135                 140
Met Met Glu Asn Leu Gln Arg Ile Met Arg Pro Pro Val Ser Ser Asn
145                 150                 155                 160
Ser Lys Thr Ala Ala Trp Val Thr Glu Gly Met Tyr Ser Phe Cys Tyr
                165                 170                 175
Arg Val Met Phe Glu Ala Gly Tyr Leu Thr Ile Phe Gly Arg Asp Leu
                180                 185                 190
Thr Arg Arg Asp Thr Gln Lys Ala His Ile Leu Asn Asn Leu Asp Asn
        195                 200                 205
Phe Lys Gln Phe Asp Lys Val Phe Pro Ala Leu Val Ala Gly Leu Pro
210                 215                 220
Ile His Met Phe Arg Thr Ala His Asn Ala Arg Glu Lys Leu Ala Glu
225                 230                 235                 240
Ser Leu Arg His Glu Asn Leu Gln Lys Arg Glu Ser Ile Ser Glu Leu
                245                 250                 255
Ile Ser Leu Arg Met Phe Leu Asn Asp Thr Leu Ser Thr Phe Asp Asp
                260                 265                 270
Leu Glu Lys Ala Lys Thr His Leu Val Val Leu Trp Ala Ser Gln Ala
        275                 280                 285
Asn Thr Ile Pro Ala Thr Phe Trp Ser Leu Phe Gln Met Ile Arg Asn
290                 295                 300
Pro Glu Ala Met Lys Ala Ala Thr Glu Glu Val Lys Arg Thr Leu Glu
305                 310                 315                 320
Asn Ala Gly Gln Lys Val Ser Leu Glu Gly Asn Pro Ile Cys Leu Ser
                325                 330                 335
Gln Ala Glu Leu Asn Asp Leu Pro Val Leu Asp Ser Ile Ile Lys Glu
        340                 345                 350
Ser Leu Arg Leu Ser Ser Ala Ser Leu Asn Ile Arg Thr Ala Lys Glu
        355                 360                 365
Asp Phe Thr Leu His Leu Glu Asp Gly Ser Tyr Asn Ile Arg Lys Asp
370                 375                 380
```

```
Asp  Ile  Ile  Ala  Leu  Tyr  Pro  Gln  Leu  Met  His  Leu  Asp  Pro  Glu  Ile
385                      390                 395                      400

Tyr  Pro  Asp  Pro  Leu  Thr  Phe  Lys  Tyr  Asp  Arg  Tyr  Leu  Asp  Glu  Asn
                    405                      410                      415

Gly  Lys  Thr  Lys  Thr  Thr  Phe  Tyr  Cys  Asn  Gly  Leu  Lys  Leu  Lys  Tyr
               420                      425                      430

Tyr  Tyr  Met  Pro  Phe  Gly  Ser  Gly  Ala  Thr  Ile  Cys  Pro  Gly  Arg  Leu
               435                 440                      445

Phe  Ala  Ile  His  Glu  Ile  Lys  Gln  Phe  Leu  Ile  Leu  Met  Leu  Ser  Tyr
     450                      455                      460

Phe  Glu  Leu  Glu  Leu  Ile  Glu  Gly  Gln  Ala  Lys  Cys  Pro  Pro  Leu  Asp
465                      470                      475                      480

Gln  Ser  Arg  Ala  Gly  Leu  Gly  Ile  Leu  Pro  Pro  Leu  Asn  Asp  Ile  Glu
                    485                      490                      495

Phe  Lys  Tyr  Lys  Phe  Lys  His  Leu
               500
```

( 2 ) INFORMATION FOR SEQ ID NO:29:

( i ) SEQUENCE CHARACTERISTICS:
        ( A ) LENGTH: 503 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Met  Met  Thr  Ile  Ser  Leu  Ile  Trp  Gly  Ile  Ala  Val  Leu  Val  Ser  Cys
1                   5                   10                      15

Cys  Ile  Trp  Phe  Ile  Val  Gly  Ile  Arg  Arg  Arg  Lys  Ala  Gly  Glu  Pro
               20                       25                      30

Pro  Leu  Glu  Asn  Gly  Leu  Ile  Pro  Tyr  Leu  Gly  Cys  Ala  Leu  Lys  Phe
               35                       40                      45

Gly  Ser  Asn  Pro  Leu  Glu  Phe  Leu  Arg  Ala  Asn  Gln  Arg  Lys  His  Gly
     50                       55                      60

His  Val  Phe  Thr  Cys  Lys  Leu  Met  Gly  Lys  Tyr  Val  His  Phe  Ile  Thr
65                  70                       75                      80

Asn  Ser  Leu  Ser  Tyr  His  Lys  Val  Leu  Cys  His  Gly  Lys  Tyr  Phe  Asp
                    85                       90                      95

Trp  Lys  Lys  Phe  His  Tyr  Thr  Thr  Ser  Ala  Lys  Ala  Phe  Gly  His  Arg
               100                      105                     110

Ser  Ile  Asp  Pro  Asn  Asp  Gly  Asn  Thr  Thr  Glu  Asn  Ile  Asn  Asn  Thr
          115                      120                     125

Phe  Thr  Lys  Thr  Leu  Gln  Gly  Asp  Ala  Leu  Cys  Ser  Leu  Ser  Glu  Ala
     130                      135                     140

Met  Met  Gln  Asn  Leu  Gln  Ser  Val  Met  Arg  Pro  Pro  Gly  Leu  Pro  Lys
145                      150                     155                     160

Ser  Lys  Ser  Asn  Ala  Trp  Val  Thr  Glu  Gly  Met  Tyr  Ala  Phe  Cys  Tyr
                    165                      170                     175

Arg  Val  Met  Phe  Glu  Ala  Gly  Tyr  Leu  Thr  Leu  Phe  Gly  Arg  Asp  Ile
               180                      185                     190

Ser  Lys  Thr  Asp  Thr  Gln  Lys  Ala  Leu  Ile  Leu  Asn  Asn  Leu  Asp  Asn
          195                      200                     205

Phe  Lys  Gln  Phe  Asp  Gln  Val  Phe  Pro  Ala  Leu  Val  Ala  Gly  Leu  Pro
     210                      215                     220
```

```
Ile  His  Leu  Phe  Lys  Thr  Ala  His  Lys  Ala  Arg  Glu  Lys  Leu  Ala  Glu
225                      230                     235                     240

Gly  Leu  Lys  His  Lys  Asn  Leu  Cys  Val  Arg  Asp  Gln  Val  Ser  Glu  Leu
                    245                      250                     255

Ile  Arg  Leu  Arg  Met  Phe  Leu  Asn  Asp  Thr  Leu  Ser  Thr  Phe  Asp  Asp
               260                      265                     270

Met  Glu  Lys  Ala  Lys  Thr  His  Leu  Ala  Ile  Leu  Trp  Ala  Ser  Gln  Ala
          275                      280                     285

Asn  Thr  Ile  Pro  Ala  Thr  Phe  Trp  Ser  Leu  Phe  Gln  Met  Ile  Arg  Ser
     290                      295                     300

Pro  Glu  Ala  Met  Lys  Ala  Ala  Ser  Glu  Glu  Val  Ser  Gly  Ala  Leu  Gln
305                      310                     315                     320

Ser  Ala  Gly  Gln  Glu  Leu  Ser  Ser  Gly  Gly  Ser  Ala  Ile  Tyr  Leu  Asp
                    325                      330                     335

Gln  Val  Gln  Leu  Asn  Asp  Leu  Pro  Val  Leu  Asp  Ser  Ile  Ile  Lys  Glu
               340                      345                     350

Ala  Leu  Arg  Leu  Ser  Ser  Ala  Ser  Leu  Asn  Ile  Arg  Thr  Ala  Lys  Glu
          355                      360                     365

Asp  Phe  Thr  Leu  His  Leu  Glu  Asp  Gly  Ser  Tyr  Asn  Ile  Arg  Lys  Asp
     370                      375                     380

Asp  Met  Ile  Ala  Leu  Tyr  Pro  Gln  Leu  Met  His  Leu  Asp  Pro  Glu  Ile
385                      390                     395                     400

Tyr  Pro  Asp  Pro  Leu  Thr  Phe  Lys  Tyr  Asp  Arg  Tyr  Leu  Asp  Glu  Ser
                    405                      410                     415

Gly  Lys  Ala  Lys  Thr  Thr  Phe  Tyr  Ser  Asn  Gly  Asn  Lys  Leu  Lys  Cys
               420                      425                     430

Phe  Tyr  Met  Pro  Phe  Gly  Ser  Gly  Ala  Thr  Ile  Cys  Pro  Gly  Arg  Leu
          435                      440                     445

Phe  Ala  Val  Gln  Glu  Ile  Lys  Gln  Phe  Leu  Ile  Leu  Met  Leu  Ser  Cys
     450                      455                     460

Phe  Glu  Leu  Glu  Phe  Val  Glu  Ser  Gln  Val  Lys  Cys  Pro  Pro  Leu  Asp
465                      470                     475                     480

Gln  Ser  Arg  Ala  Gly  Leu  Gly  Ile  Leu  Pro  Pro  Leu  His  Asp  Ile  Glu
                    485                      490                     495

Phe  Lys  Tyr  Lys  Leu  Lys  His
               500
```

( 2 ) INFORMATION FOR SEQ ID NO:30:

( i ) SEQUENCE CHARACTERISTICS:
        ( A ) LENGTH: 504 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Met  Met  Thr  Ile  Ser  Leu  Ile  Trp  Gly  Ile  Ala  Met  Val  Val  Cys  Cys
1                   5                        10                      15

Cys  Ile  Trp  Val  Ile  Phe  Asp  Arg  Arg  Arg  Lys  Ala  Gly  Glu  Pro
               20                      25                     30

Pro  Leu  Gln  Asn  Gly  Leu  Ile  Pro  Tyr  Leu  Gly  Cys  Ala  Leu  Lys  Phe
               35                      40                     45

Gly  Ser  Asn  Pro  Leu  Glu  Phe  Leu  Arg  Ala  Asn  Gln  Arg  Lys  His  Gly
     50                      55                     60

His  Val  Phe  Thr  Cys  Lys  Leu  Met  Gly  Lys  Tyr  Val  His  Phe  Ile  Thr
```

-continued

```
 65                      70                      75                      80
Asn Ser Leu Ser Tyr His Lys Val Leu Cys His Gly Lys Tyr Phe Asp
                85                      90                      95
Trp Lys Lys Phe His Tyr Thr Thr Ser Ala Lys Ala Phe Gly His Arg
            100                     105                     110
Ser Ile Asp Pro Asn Asp Gly Asn Thr Thr Glu Asn Ile Asn Asn Thr
        115                     120                     125
Phe Thr Lys Thr Leu Gln Gly Asp Ala Leu His Ser Leu Ser Glu Ala
    130                     135                     140
Met Met Gln Asn Leu Gln Phe Val Leu Arg Pro Pro Asp Leu Pro Lys
145                     150                     155                     160
Ser Lys Ser Asp Ala Trp Val Thr Glu Gly Met Tyr Ala Phe Cys Tyr
                165                     170                     175
Arg Val Met Phe Glu Ala Gly Tyr Leu Thr Leu Phe Gly Arg Asp Thr
            180                     185                     190
Ser Lys Pro Asp Thr Gln Arg Val Leu Ile Leu Asn Asn Leu Asn Ser
        195                     200                     205
Phe Lys Gln Phe Asp Gln Val Phe Pro Ala Leu Val Ala Gly Leu Pro
    210                     215                     220
Ile His Leu Phe Lys Ala Ala His Lys Ala Arg Glu Gln Leu Ala Glu
225                     230                     235                     240
Gly Leu Lys His Glu Asn Leu Ser Val Arg Asp Gln Val Ser Glu Leu
                245                     250                     255
Ile Arg Leu Arg Met Phe Leu Asn Asp Thr Leu Ser Thr Phe Asp Asp
            260                     265                     270
Met Glu Lys Ala Lys Thr His Leu Ala Ile Leu Trp Ala Ser Gln Ala
        275                     280                     285
Asn Thr Ile Pro Ala Thr Phe Trp Ser Leu Phe Gln Met Ile Arg Ser
    290                     295                     300
Pro Asp Ala Leu Arg Ala Ala Ser Glu Glu Val Asn Gly Ala Leu Gln
305                     310                     315                     320
Ser Ala Gly Gln Lys Leu Ser Ser Glu Gly Asn Ala Ile Tyr Leu Asp
                325                     330                     335
Gln Ile Gln Leu Asn Asn Leu Pro Val Leu Asp Ser Ile Ile Lys Glu
            340                     345                     350
Ala Leu Arg Leu Ser Ser Ala Ser Leu Asn Ile Arg Thr Ala Lys Glu
        355                     360                     365
Asp Phe Thr Leu His Leu Glu Asp Gly Ser Tyr Asn Ile Arg Lys Asp
    370                     375                     380
Asp Ile Ile Ala Leu Tyr Pro Gln Leu Met His Leu Asp Pro Ala Ile
385                     390                     395                     400
Tyr Pro Asp Pro Leu Thr Phe Lys Tyr Asp Arg Tyr Leu Asp Glu Asn
                405                     410                     415
Lys Lys Ala Lys Thr Ser Phe Tyr Ser Asn Gly Asn Lys Leu Lys Tyr
            420                     425                     430
Phe Tyr Met Pro Phe Gly Ser Gly Ala Thr Ile Cys Pro Gly Arg Leu
        435                     440                     445
Phe Ala Val Gln Glu Ile Lys Gln Phe Leu Ile Leu Met Leu Ser Tyr
    450                     455                     460
Phe Glu Leu Glu Leu Val Glu Ser His Val Lys Cys Pro Pro Leu Asp
465                     470                     475                     480
Gln Ser Arg Ala Gly Leu Gly Ile Leu Pro Pro Leu Asn Asp Ile Glu
                485                     490                     495
```

Phe Lys Tyr Lys Leu Lys His Leu
                500

( 2 ) INFORMATION FOR SEQ ID NO:31:

( i ) SEQUENCE CHARACTERISTICS:
        ( A ) LENGTH: 7997 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
GAGCTCTACC CTTGCTCTGC TATTGTACTT TTTAATACAC AGTTCAATCA AATGTGCCAC      60
CAGAATATGC ATGCTAACAG CTGTAGTGGT TGATTTTTCT TTCTACTCTT CTGTGTGTAA     120
GACCCCATGT TTTATCAATT ATTTTTAAT  GATTTCTTTC TTCATGCATA TGTGTGGTTG     180
TCAGTGTGAG TCTGTGTGTA CAGCAGGTGC ACAGGTATCC ACAGAGGCCA GAGGTTCCCT     240
GTAACTAGAA TTACAGGCAC TTGTGAACTT TCCTGTATGG GTGCTGGGAA GCAATCTGAG     300
GTCTTCTGCA AGGGATCTTA ACCACTGACT TTCTAGCCTG CTTTGCCCAT TTCTATTTAT     360
GATGACTGGA AACTGGGCTT AGGCCTTATA TTCTCTGAGG CCAAAATCAA GTTCTTCCAA     420
ACTGCAGGAT TTATGGTCTT CTATAGTATC CCACAGAAAT GGAAAAGAAA GTGACCCATT     480
AGAGCAGTAT TAGAGTCGAA ATAAACTCAA CTTGGTATGC CAGGACTTTG GACAATAATA     540
ACCCTGTCTT TTCAGGGCAT CTATCTGTAC TGCTGCAATA GAAACTCCAC AGGTCAGGGT     600
CACAGCTGTT GTGTTTTACA CAGTGTCCCC AGGATTAGTT CAGTGCCCAC CATGCAATAG     660
GTGTCATGGT GTGTGTGTGT GTGTGTGTGC GTGTGTCGTG CTTGTGTGCA TGTGTGTGAG     720
ACACACACAC AGAGAGATAC AAAGACAGAA ACAGAAAATT AATAAAATTT TACCAACTAA     780
AATAGGGAAT TAAAGAAAAG GAGGAGAAAA AGTTGGGCAT TCAACACCAT AAAGTCCCAG     840
TACTATGCTA AGAACACCCA GCTGTCCTCA CACCCGGGCA TGAAACTTCA TGCACTGTTC     900
ATCAGAAAAT CGTTTACACA CATCCCCTTG CAGTCTACTT GTAGTTTTAA CAACTTCAGA     960
GAGCACTAGC ATTTCCAGCC CCAGGTTAGA AGCTTGGTA  GATGCTGTTT GCGAGCACAG    1020
GATAGCAGCA AGAAGTGGAC TTGTTAGAAG GAAAGCCAAT GCCTATGTAA CAACGAAAAC    1080
TAAGTATGAA TCTCGAATCT CCACTCTCGT GTGTCTGTGT CTCCATATAC GTGCTTGGGT    1140
GCCTGACATG GCAAGGTGTT ACAAGTAAGG GAGGAACAAG AAAAGGACAG GGTAGTGGAC    1200
ATCAGGATGA ATGCCAGCCA GGGCGACTGG AGAGAGTCTA CGCTGCTCTG AAGGTGGGTG    1260
AAGAAGACCT CAGGAAGCTT TCTGAGGCTC CGAGAGTGCT TTTCCCTTCC CATGTTGAAA    1320
CATCCTTATT TGCAGAGAAT TCCAGGTTCA TGGGAATTTG TAAAGAGAAT ACTAAGAGGC    1380
CACCTGTGGC TTCTCCTATT TTTGTCTGCT GTCATTTATG GGACAGGGTT AGAGACCTGG    1440
CTTGCTTGGC TATGAGGCTG TTGCTTCCTC GGTTACTCTG CTGTGGTTGG ATGCATTAGG    1500
GTTAGGCCCC TCAAGAGCCA TGTGTCATTT TATAAAAGCA ATATAAATAT ACTTAAGGTG    1560
CACAAAGCAT TAGGAGGTCT GAGATAATAG ATTCTGAGAA AATCTATCCT GCTGTGTAGC    1620
AACTGATGTT TATGATTATA GTCCCAGACC ACACGATAAA GGATCTGTGG ACTCTGTTTA    1680
GGGAGGTCAA AAAACTATTG CAAATGGAGT CTATAGAGAA AACTAGACAG GACTCAATGC    1740
TCACCAATCG AGAATTAGTT GATGAGCTGG GGTAGTGACT TAGTGGATAA GAACACGGTC    1800
CTTTCAGAGG TCCTGAGTTA AATCCCCAGC AAACACATGG TGGCTCATAA CCATCTATAT    1860
TGTGATTTGA TGCCCTCTTC TGGCATGCAG GTGTACATGC AGACTCGTAT ACATAAAATA    1920
```

| | | | | | | |
|---|---|---|---|---|---|---|
| AATAAATCTT | GAAAAAATGA | ATACGTTGAA | TAAGTGTCCC | CTCGGATAAC | TTTCTGCAGA | 1980 |
| ATTTTAAGCA | CATGTCAATG | GTAATAACAC | ACACACACAC | ACACACACAC | ACACACACAC | 2040 |
| ACACACATAC | ACACACCATA | CAGATATGTA | TCTAGAGACA | TACACATGTA | CATTTTATCT | 2100 |
| CTTTTATTTT | CTTCTCCCCT | CTTTGACATC | AAGGAATAGA | ATGCACTCAC | TGTGGCCTAG | 2160 |
| TGCCACACTC | TACCTATTTC | TTTGGCTTTA | CTTTGTGCTA | GGTGACCCGA | AAGGTTTAAA | 2220 |
| TATCAAAAAT | GCTAATGGCT | CGACATTTAC | ATCCCCAATT | TCTCCTTTCT | CCTTACCTCA | 2280 |
| GACTCTTACA | TTCAGTTGAC | AATTTGACAT | CGTCTCCTGG | ATTTTCAAAT | GTTCAGCACA | 2340 |
| CTGTACTGAT | GTACTGCCTT | CCAAGGCAAC | CGGCACGATC | CTCTCCCCAC | TCCCAAGCAT | 2400 |
| CCCTCCATGA | GCCAGTGTTT | GCTTATCTTC | TTGACTCTTG | TTTTAACCCA | ACTCCTCCCC | 2460 |
| TATTCACTCT | GCTCTAATTC | ATTCATTCTA | TATTTCGCA | CATCAGGCTC | ATCCTTTGCT | 2520 |
| CAGGAACTTC | ACTTTTGCTT | TCCGGTCTCC | TGGAAATGTG | TTTTCTTGGC | TATTCCATCT | 2580 |
| CAAGACCATC | TTTTCAGAAA | AGCTTTTCCT | ATCAACATAT | TTAAAGCCCT | CTTCATCCCC | 2640 |
| CAGTAGCTCT | GGACACCTCA | TTTTATGGAT | ACACAACACA | TATTTGCCAC | CTGTCTCCCC | 2700 |
| ATTAAAATAT | AATCTTCAGT | AGAGAAACTC | CATATCTTGT | TAATACCTGA | AACAAGAATA | 2760 |
| TCTTCAAAGA | GTTCCTGGGA | CATAAAAACG | CTCAATTAAT | ATTTATGTTA | AACAGGGATC | 2820 |
| TGGGGTATAT | CACAGAGGTA | GAGGGCTTAC | CTAGGAGGAG | TTGGGCCATG | GGTTCAACTT | 2880 |
| CCAGCACAGA | ATGAAAGATT | ATGTTAAATA | AAGTTGGGAA | GGATGTATGC | CAGTCTATGA | 2940 |
| GTAGTATAGG | AGGTAAATTA | TGAATTCATA | TTTACTTTTC | GGACAAGAAG | TGTTGTAGTC | 3000 |
| TTTATTTGAA | ATAAAATACA | TCTTAATTAC | CAATAACAAT | TGGTAAGGAG | TGAATTCTCA | 3060 |
| AGCTGTGGCT | TCCTGGTAGA | TGAGTCCTGG | GAGGTTTTCT | ATTTCGATGA | TGGTAGATAG | 3120 |
| GTAACCTGTC | ATATACCACA | TGAAATACCT | GTGGCTTTGT | AAACACACCG | AGCAGTCAAG | 3180 |
| CAGGAGAATA | GTTCCATACA | GTTCGCGTCC | CTTAGGATTG | GTTTCGGGAT | ACTTCTGGAG | 3240 |
| GTTCATTTAA | ATAATTTTCC | CCGAAGTACA | TTATGGGCAG | CCAGTGTTGT | GATGGGAAGC | 3300 |
| TTCTGCCTGT | TTTGCTTTGC | GTCGTGCTCC | ACACCTTTGA | CAGATGTGCT | CTCATCTGTT | 3360 |
| TACTTCTTTT | TCTACACACA | GAGCACAGCA | TTAGCTGCTG | TCCCGGCTTT | GGATGTTATG | 3420 |
| TCAGCACATG | AGGGACAGAC | CTTCAGCTTA | TCGAGTATTG | CAGCTCTCTG | TTTGTTCTGG | 3480 |
| AGCCTCTTCT | GAGACTATGG | ACTTAGTTCA | AGGCCGGGTA | ATGCTATTTT | TTTCTTCTTT | 3540 |
| TTTCTAGTAG | GAGGACAAAT | AGTGTTTGCT | TTGGTCACTC | AAGTTCAAGT | TATTGGATCA | 3600 |
| TGGTCCTGTG | CACATATAAA | GTCTAGTCAG | ACCCACTGTT | TCGGGACAGC | CTTGCTTTGC | 3660 |
| TAGGCAAAGA | GTCTCCCCTT | TGGAAATTTT | CCTGCTTTTG | CAAAATGATG | ACTATTTCTT | 3720 |
| TGATTTGGGG | AATTGCCGTG | TTGGTGAGCT | GTTGCATATG | GTTATTGTT | GGAATAAGGA | 3780 |
| GAAGGTATGG | AAAGATTTTT | AAAAATTTGT | CTTTTAGCTT | ATTTCTAGTA | TTCATTGCCT | 3840 |
| TCACTATTAT | GTAGTGCAAA | AAATACTAAT | GCATTAATAT | TTTTAAATTT | AAAATTTAAA | 3900 |
| GACGTACTTC | TTTGACTAAA | TCTAGTAAGA | TGTAGAGAGT | CCCCCTTGGA | ACATTCACAT | 3960 |
| ATGCCACTGG | TAATGCAGAT | CTTGTGAAAT | ATAACTAAAG | AAATCACAAG | TCATCGATGT | 4020 |
| AAGTTTGTGT | CTGCATGGGC | GGAACAAACC | TAAGCTAAGA | AGAGTAGTAT | TGGGAGGGA | 4080 |
| TCTTTCTGTG | ACATGAACTG | AATAGACGCA | CTGCCTCAGC | AAACACACAT | TCATTTGAAT | 4140 |
| TTTCCTCAGA | CTCAGTCTAA | GCCTGGTGAG | AGCACCAAGT | GTGAGTCTGT | CTGCCACTAA | 4200 |
| CGTTTCCTTC | CAGTGGTAAT | CAGCTGTGTG | GCTGTGAAAC | CTTGGCGCCT | GCACATGACA | 4260 |
| GCCATTTGAA | TAGTTCAAAG | AACATTTAGG | GACAGGATAT | TAAGATATTT | TCTGTGATGT | 4320 |

```
CAACATCAAA ATAGGAGAAT GCCCCTGGCA TTATCTTCAG AGAGGTAGAC TACTGTGCGT    4380
TGTCTTACTT TAAAGAAATT TCTTTGCCCC TTTGGCTATT TTAATTCAAA CCTGAAAGTT    4440
TTCAGTTTTA ATTAAACTGT TGATTTTCAT GCTAGGAAAG GAAATATCAA TTATACTTAA    4500
TTGTTCTTAC AAGAAATAAA ATCATTTATG TCGGAGATA  AATAAGCTCA TAATTTTAAT    4560
AAAACATTTA AGAGAGAGAA AAAGAGTAGT GGATTATAGT TCATTGTCTG TCAATGTTTA    4620
CCTGACCCAG TTTCATTTTA TAATTATCTA ATTTTTCAAA TGAGATTCCT GTTCTTTCCA    4680
AATATCATTG CAGAATACTA ACATTCTTTT TTTCAGAGTT GAGAATCAAA TGGAGGGTTT    4740
TTTCATCCTG GCACAAGCTC CGCTCTTCAG TAACACCTCC AGCCCTCAGA ATGCCAATAT    4800
TTTAAATTAT GTAGGTTGTT AAAACTTTAG TGCTGGGGCT GGGGATTTAG CTCAGTGGTA    4860
GAGCACTTGC CTAGCAAGCG CAAGGCCCTG GGTTCGGTCC CCAGCTCTGA AAAAAGAAA    4920
AAGAAAAAAA AAAACTTTAG TGCTGTAGCC CTTTCTGTTA TTTGATGTTT CACATCTGTT    4980
AAAAAACAAA ACAAAACAAA AAAACAAGC  AAATGGAACA TTTTAGGCAT TCTTTGGGGG    5040
AAATGATTCT TAGAGCAAGT CTAATCATTA GGTGATAGTT TCATTTTTAC ACCAAGAACA    5100
AGAATCTTGT TGGCTGTGTT AACACTTTAA GCCCTGTTGT AGGGAAAAG  CAATCAGACA    5160
CAGGCACAGA AAAGAATTTG GATGAGTACT TGATGATGTA TGTATATATG GTGAATAGAC    5220
TGATGGGTGG GCTGCTGGCT GGGTTGGTAA GTGGGTAGAT TTTTTTTAA  AGATTTATTC    5280
ATTTATTATA TATCAGTACA CTGTAGCTAT CTTCAGATAC ACCAGAAGGG CATCGGATCT    5340
CTTACAGAT  GGTTGTGAGC CACCATGTTT TCCTAACCTC TCAAGTCTCT GTCTTCCAGG    5400
AAAGCTGGTG AACCTCCTTT GGAGAACGGG TTGATTCCGT ACCTGGGCTG TGCTCTGAAA    5460
TTTGGATCTA ATCCTCTTGA GTTCCTAAGA GCTAATCAAA GGAAGCATGG TCACGTTTTT    5520
ACCTGCAAAC TGATGGGGAA ATATGTCCAT TTCATCACAA ACTCCCTGTC ATACCACAAA    5580
GTCTTATGTC ATGGAAAATA TTTTGACTGG AAAAAATTTC ATTACACTAC TTCTGCGAAG    5640
GTAATTAATT CGTTATACAG ATTCTGTTTG TTTCCTGGTC TGTTGATGTA TTAGTGTATT    5700
TAGTTGTTCC AATTTTGTTA GGTTGCAGAA TAGAGGTAAC ATAAAATCAG GGCGTTTCTT    5760
AGTAATAAGC ATTAGACATT TAAGGCAGAT GTAAACCTGT CATTGATGAT TCCGGAGACA    5820
GAGGACACTG CAGGAATCAG GAAGGTACAG ATTCATAGCA CCACTCGTCC CTTAACAACA    5880
CCCTGAGCAG GGTGTTGGCA CTCTTAGCCT TCAGTCCTTG TACACACGTT TCATTCCTAA    5940
GATATAGGCT GTATATTTAA ACACGATTTG GAAGCCATCA AGAATCTGTT CTAGAGAAAA    6000
CAGCATTTAA TGATCTTTTG CAAGAAAATA TCAGTTATAG TCTCTGTCAT TAAGTACATT    6060
GTAATCTGGT TAAAGAGTAT CTACTAAGAA AGTAAAGGCA GATTAGAACA ATACCAATGG    6120
ATGATGGGCC ATCCAGAGAA ATCCTACTGT AAATGCTGGG ATTTAAACTT GACCCCAAGG    6180
AAGAGTATGA CTTGATTCTA CCTTTGGAAT GTGCTGTAAA ATCATATTAG GAAGGTTCC    6240
AGACAGAGAA GTGGATGTA  TTTAATCTAT CTTCCAGCCC ACTCTCTAAC ACTAGCTAGC    6300
TTTGGGCTTT AGACCCTCCC CATTTCATGG ATTCTATTTT CTACCAGGCA TTTGGACACA    6360
GAAGCATTGA CCCAAATGAT GGAAATACCA CGGAAAATAT AAACAACACT TTACCAAAA    6420
CCCTCCAGGG AGATGCTCTG TGTTCACTTT CTGAAGCCAT GATGCAAAAC CTCCAATCTG    6480
TCATGAGACC TCCTGGCCTT CCTAAATCAA AGAGCAATGC CTGGGTCACG GAAGGGATGT    6540
ATGCCTTCTG TTACCGAGTG ATGTTTGAAG CCGGCTATCT AACACTGTTT GGCAGAGATA    6600
TTTCAAAGAC AGACACACAA AAAGCACTTA TTCTAAACAA CCTTGACAAC TTCAAACAAT    6660
TTGACCAAGT CTTTCCGGCA CTGGTGGCAG GCCTTCCTAT TCACTTGTTC AAGACCGCAC    6720
```

```
ATAAAGCTCG GGAAAAGCTG GCTGAGGGAT TGAAGCACAA GAACCTGTGT GTGAGGGACC    6780
AGGTCTCTGA ACTGATCCGT CTACGTATGT TTCTCAATGA CACGCTCTCC ACCTTTGACG    6840
ACATGGAGAA GGCCAAGACG CACCTCGCTA TCCTCTGGGC ATCTCAAGCA AACACCATTC    6900
CTGCAACCTT TTGGAGCTTA TTTCAAATGA TCAGGTAACT TTCCAGTGAC AGAAATTGCA    6960
TTTTAAACTC AAAACCCAAA AAGACTTATA GAGCTTTCTG TGCTATCAAC AAAGAAAGTA    7020
ATACTCAATG TCCGTGTTTA GCATGTGCGT AACAGAAGCA GCAATTTTTA GGTGCACAGT    7080
CCCATCGAAA GGGATGTCCC AGAAGCCACA GAACTCAGAC AGGTTGGTGC TCCATTAGTA    7140
CAGGTTCCCT GGCCTAGTCT TGCTCCTCAC CCGATATGTT CCTCTTAATA TCAAATTAAA    7200
TCCCCGAGTG CAGTCGTCAC CACCATATAA ACATTTGAAA TGATGACTGA CTTGCAGGTG    7260
TGATAAGAGC AGTGACCATA CCTTACTAAT TCACTGGAAT TCATAGGCAA AGTAACACCA    7320
TCGATTTTGT ATTCATATAG GAGCTGCAGC CATATTTTAA ATAGCACAAC TACTTGTTAG    7380
TCAAGCATTC TGAGGCTCAC TGTAATCAGG TAAAGTAGGT TTAACTCAGC GTCCTACCAG    7440
TTCCAGGCAT TGAAATGGAA TATCCTTTAT CCCACCCATT CAAAACGTAA TATATAAATG    7500
GAAGGCACAG TTTTGAAGGC CATGGTATGA TTTAGGGAAT TTACTCTCAT GGTCCAATCC    7560
CTTGTAATTG TATGCTAGGT GACATATCCT TCTGACTTAC TATGTTCATC GTATATTCAA    7620
TCCTTAGTTT ATAGAGACTG ACCAAAGCTC TGCTTTTGCA TAGCAAAGCT CCTTTTAATG    7680
CCCATTCCTA AACTCAAGGA CACGAATCCA GTTCAGTGCC CTTTTGCATA CTCCCTGGCA    7740
GACTCCCGTT GCCATACATC CTCCCTCGCT CGATTCCCAT GACCTCGCCC TTGCACACCC    7800
TGGTACTAGG ACCTCTCCTG GCGATACTTC CTACTACCTA TGCCACCTCA TTAAAAGGAA    7860
GGGATAATTG CTATTTACTT GCAGTTCTCT GAATGAGGAC ATTTTCCCCA TACGGCTCTT    7920
TCCACAGGAG TCCTGAAGCA ATGAAAGCAG CCTCTGAAGA AGTGAGTGGA GCTTACAGA     7980
GTGCTGGCCA AGAGCTC                                                   7997
```

( 2 ) INFORMATION FOR SEQ ID NO:32:

( i ) SEQUENCE CHARACTERISTICS:
        ( A ) LENGTH: 5537 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
TTTTTGGTTA TCTTTTCAGC CGTGCCCCAC TCTACTGGTA CCAGTTTACT GTATTAGTCG      60
ATTTCATGC TGCTGATAAA GACATACCTG AAACTGGACA ATTTACAAAA GAAAGAGGTT      120
TATTGGACTT ACAATTCTAC ATCACTTGGG AGGCCTCACA ATCATGATGG AAGGAGAAAG     180
GCACATCTCA CATGGCAGCA GACAAGAAAA GAGCTTGTGC AGGGAAACTC CTCTTTTTAA     240
AACCATCAGA TCTCATGAAA TTTATTCATT ATCATGACAA TAGCACAGGA AAGAACTGCA     300
CCCATAATTC AGTCACCTCC TACCAGGTTC CTCCCACAAC ACGTGAGAAT TCAAGATGAG     360
ATTTGGATGG GGACACAGCC AAACCATGTC ACACTACCAT GCCTGACTTC CTTTCCATTT     420
TTGTATATTT GCTTGTTCTT CATTTGCCCG AGAAGTAACT CTAAAGGGCT GTATTATTTG     480
GATATTAGAT TGGCATTTTA TCTGACTGGG ATATCTTGCT GTGATTGTCC ATGTATAAGA     540
TCAGCTTTTC TATAAGCCAT ATTTTTAAAA AGATATATTA ATTTTTAAA AATCCACCTG      600
TCTAAATAAA TGCACAAAGC CCCCCAAAAA CCTAGATTCT AAGAAAAATC TATGTACTGC     660
CATACAATGA TTGATATTAA TATTTATGGT GATAAATTAC ACACAAAAAA TGTGTGATCT     720
```

```
CTGTTTAAAC AGGCAAAAAC AAAAAACACA TGAAATAAAT CTATGGCATC TATAGCCAAA      780
ACTGGAAACA ACCCACATAT CCATCAATAG GAAATCAGTT AAATAAATTA TAGTACATTT      840
ATCCAATGGA AGATTAAGCA CATATTCAAT ATAATTATTT ATACACACAT ATAGATACAC      900
ACATGTATAA ATATAGAGAA TACTGTGGGT GTATGTGTGT GTGTGTTTAT ATACATATAT      960
ATACACACAC AGTACTGTTG CCTACCTTCT TTTGTCTTAA TTCTGTGAAC TCTCATTCAC     1020
TCTGCTTCAG TAGGATACCT CCTTCTTTTT GGTTCTTAGA CTCACCAAGT TGATCCTTGA     1080
CTCAAGACAT TGCATTTGCT GCTTCCTCTT CCTGGAATAT CCTTCCTTCT GATATTCACA     1140
TGAGTAGTCT CTTCTTGTCA TTCAGATCTC AAATGTCACA ATTTCAGAGA GCCCATCTCT     1200
GATCATCATA TCTAAAGTTG TCCTCATTCC CCATAGCTT TCTATACCAT GTTTATTTT      1260
TTTCATAACA TGTATTTTAT TACTCCTTTC TCCATTGGAA TAGAATCTCC ATTAGATTAG     1320
GAAATCTGCC TATCTTATTA ATGCCTGCAA CTGGAATACT TTGAAGAGT TCTTGGCACG      1380
TAATAAATAC TCAACTAATA TTTTGTGTA CACAGAAATA AAGTTTGGAA GAACAGATGC      1440
CAAATTGTTA CTAGTGGTTA CTTCTGAGTA AAGGAGTAGC ATGGTAGGTA AATTATTAAT     1500
AGATGTTCAC TTTCCACCAA GATATGTTTT AGTTAGTCTT AACTTACTTG AAATGAAATT     1560
TATTACTTTA ATAATTAGAA ACATTGATAA ACATTTAGT CACAAGAATG ATAGATAAAA      1620
TTTTGATGCT TCCAATAAGT TATATTTATC TAGAGGATGC ACTTATGTAG AATACTCTCT     1680
TGAGGATGTT AGGTGAGTAA CATGTTACTA TATGTAGTAA AATATCTATG ATTTATAAA      1740
AGCACTGAAA CATGAAGCAG CAGAAATGTT TTTCCCAGTT CTCTTTCCTC TGAACTTGAT     1800
CACCGTCTCT CTGGCAAAGC ACCTAAATTA ATTCTTCTTT AAAAGTTAAC AAGACCAAAT     1860
TATAAGCTTG ATGAATAACT CATTCTTATC TTTCTTTAAA TGATTATAGT TTATGTATTT     1920
ATTAGCTATG CCCATCTTAA ACAGGTTTAT TTGTTCTTTT TACACATACC AAACTCTTAA     1980
TATTAGCTGT TGTCCCCAGG TCCGAATGTT AAGTCAACAT ATATTTGAGA GACCTTCAAC     2040
TTATCAAGTA TTGCAGGTCT CTGATTGCTT TGGAACCACT TCTGATACCT GTGGACTTAG     2100
TTCAAGGCCA GTTACTACCA CTTTTTTTT TCTAATAGAA TGAACAAATG GCTAATTGTT      2160
TGCTTTGTCA ACCAAGCTCA AGTTAATGGA TCTGGATACT ATGTATATAA AAAGCCTAGC     2220
TTGAGTCTCT TTTCAGTGGC ATCCTTCCCT TTCTAATCAG AGATTTCTT CCTCAGAGAT      2280
TTTGGCCTAG ATTTGCAAAA TGATGACCAC ATCTTTGATT TGGGGATTG CTATAGCAGC      2340
ATGCTGTTGT CTATGGCTTA TTCTTGGAAT TAGGAGAAGG TAAGTAATGT TTATCTTTA      2400
AATTGCTCTT TGATTCATCC ATTTAATTTT TTTACCTTCA TTTTTATACA GTAAATTTGG     2460
TTTTCTATAC TTACACATAT TAGCATTATC TTCCTTATGT TTTAAATGAA AAATTTGATT     2520
TGAATTTTTA AAGTAATATC TTTTTTACTA TATCTCACAA GACATATGAC AGCTTCCCTT     2580
TTTAGTATTG GCATATACCG ATGGTAATAT ATAAATGTAT ATTGGTGTTA AACATAACTG     2640
ACAGAAATTG TATAAGGTCT CTATGTACAT TTATATGTGT ATCTAAAGAG GAAGCCCAGA     2700
TTAGTAAGGA TACAAGTAGC AAGTGGGAAT CTACAATGGA AAGGATTGCT TTCTCTCACA     2760
TGGCTTCAAT AGATACTCTT GCTTAAATAA ATGTTCTCTT TTAAGCTCAT TCTTGTGCAT     2820
CGCATAGACT CAGCCTAAGC CTGAACAAGA GCATAGAGCC TGAGCTGATC ATTCTATTAC     2880
TGTTTTTAAA TAAATGTTAA TCAACTGTGG TGAATTGGGA AAGTTTGCTG AGTGTATGTG     2940
ACATCGATTT CATTTATTTA CAACTGGTTC AAGAATGCAA GAAAACAAA TACAGTCAGA      3000
TCCAGAACCA TAGTTTATTT AACTTCTAAT TGGCTCAAGG AGTAATTGTG GGGAGGCATA     3060
TAGATATTCT CTGCTATGTC AATCTCAAAA AGAGAAAATA ACCCTAACCA TCTTTCAGCT     3120
```

```
TTGTAGATTG CTATGTGTTT TCTGCCTTTG CAGTTTCTTT CAGGCCTGAT AGTTTTTACT    3180
TTTAATTAAA CTACTTATCT TCAAACTAAG AAAAGAAAGG TAATTACTTT ATACTGTATT    3240
ATTCTATCAA GAGGTACAGA AGTTTATGTT GGAAAATAAG TTTACATGTT CTAATAAAAA    3300
CATTTTAAAG GAGCACTGAA TTACAATAGA TGATTCCGTC AGTGTTTATC TTACTCAATT    3360
TCATTTTATA ATAAGCTGAT TTCTCACATG AGATTCTTCT TCTCTGAAAC CATCCTTATA    3420
GAATATAATA TAGATATCTT TAAACTAGGA ATATTTCAA  AACCTCAGTT CTGAAATCCT    3480
CCCTTATTCA GTGATCTGTG TCTTTAAAGA AAATAATCAA AGAAACATT  TTGAGATATT    3540
TAGAAAAATG ATGCTTAGCA AAGTGATAAA CACTAGAATG TAGTTTTGTT TCCGCACTGA    3600
CAACAAGAAT CTTGTTGGTC TTGTAAATCC TTTTGCCTGT ATCACTGGGA AAAGTGATGA    3660
GCACATAGTA GACGGGTGCT TGTTGAATGT GTATATGGAC GGATGCATGA ATGGATGGAT    3720
TTAGTAATCC TTTCCACCAA CATATCATGT TACTAGGTTA ATATAACCTA TTACTGTAGT    3780
AAAAGAGCAG GGCCCATCCA ACAAAAGAAA TATCTATAAA CTATAGGGTT TCAAAGTTTG    3840
AAGTCAGTGG GAAAAATTTT AAAACCTGAT GTAAGTAAAA ACCCAAAACT GTAATCATCC    3900
ATGTCTATCA TACACTTGTG TCTGACAGGC AAACGGGTGA ACCACCTCTA GAGAATGGAT    3960
TAATTCCATA CCTGGGCTGT GCTCTGCAAT TTGGTGCCAA TCCTCTTGAG TTCCTCAGAG    4020
CAAATCAAAG GAAACATGGT CATGTTTTA  CCTGCAAACT AATGGGAAAA TATGTCCATT    4080
TCATCACAAA TCCCTTGTCA TACCATAAGG TGTTGTGCCA CGGAAAATAT TTGATTGGA    4140
AAAAATTTCA CTTTGCTACT TCTGCGAAGG TAAGCAGTTT TACATTTATA TACCATTCTG    4200
TTTGTCTTCT ACCTTTTTAT GTGCTTGTCT ATTTAGAAAT TTTGATGTAC TTAGATTTTA    4260
TGATAAAGGT GTTGAAGAGA GTTATCCTTA TGTGGAGATT CTTAGAAACA TAAATAAATT    4320
ATACGTAGCT TCTTAGTAAT AATCATTTAG AAAGTCAAAA TAGGTATAGA TTTCCGTCAT    4380
TTGCTTTGCA CGAGCTAATG AGGGTGAAAT ACAGATTAAA TGCTCTACTG AGACAGGTGG    4440
CACTGTACGA ATAAGATAGA TTAAAATTCA TCACATCAGC AATGTCTATG CAGAGCGAAG    4500
TGACGGAAAC CTAACATTCA GCAGTTGTCT CACCACACTT GTGCCACACA GTGTTTCATT    4560
TTGATAAGGA ATTGGCAAGA TATTTAACA  TCATTTAGAT GTAATAAAAG AAGATCTGTT    4620
ACTGAGAAAA AAAACCAATA ACTACTTACT TACTGCAAAT AAATATTAGC TTTGGTCTTT    4680
GTGACTAAGT AGCTTAAAGT TTGGTTAAAA TACATCTACA GCTGGACACA ATGGAACACA    4740
CCTGTAGTCC CTGCTATTTG AGAGGCTGAG GCAGGAGGAT CGCTTGAGTC CAGGAGTTTG    4800
AGGCTGCAGT GAGCTATCAT TGTGTCACTG CACTCCAGCC TGGGTGACAA TGTGAGACCC    4860
CATCTCTAAA AGAAAAAGAA AAAGAAATCT ACAAATAATA TAAAAGATAA CTAATGATTT    4920
TAAAACATTA TCAATTAGTT TATGTGCAAT AGCTGTAAAT AAGTGCAGTA GCATAAGAAA    4980
TAAGACATAG ATGACTTGAG TGATCCAGGG GAGTGCCACT GAAGTTGGCT TTAAAGGAAA    5040
GGTACAGTTT GGTCATTTAT TTGTAAAGTG CTATGAACTT GTACAAGGGA AAGCCAATTT    5100
CCCGTGTTTA CCAAGTAAGG AACTATGAAA GTATCTAATC CGTTTTCAG  TCATTTACTA    5160
TGACTAGGTC AGGTTTAACT TCTTTTTCTG CATGTTTTAT TTGCTATCAG GCATTTGGGC    5220
ACAGAAGCAT TGACCCGATG GATGGAAATA CCACTGAAAA CATAAACGAC ACTTTCATCA    5280
AAACCCTGCA GGGCCATGCC TTGAATTCCC TCACGGAAAG CATGATGGAA AACCTCCAAC    5340
GTATCATGAG ACCTCCAGTC TCCTCTAACT CAAAGACCGC TGCCTGGGTG ACAGAAGGGA    5400
TGTATTCTTT CTGCTACCGA GTGATGTTTG AAGCTGGGTA TTAACTATC  TTTGGCAGAG    5460
ATCTTACAAG GCGGGACACA CAGAAAGCAC ATATTCTAAA CAATCTTGAC AACTTCAAGC    5520
```

```
AATTCGACAA AGTCTTT                                                                    5537
```

(2) INFORMATION FOR SEQ ID NO:33:

(i) SEQUENCE CHARACTERISTICS:
    (A) LENGTH: 2575 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:33:

```
GAATTCTACT CTTTAAAGGG GTGAATATTA TGGTACTTGA ATTTTATCTC AAGAAAAATG     60
AATAAAAAGT AACTAAATCA TTGAAAATAT CTGATGGCAT GGGGTTTGTG GGTAACTGG    120
CATTCCACAG TGATTTTCAA AGGGCTTGTG CTGTTTTCAT TTTGCTTTGT TTTAGTTATG   180
GAGCCCTTCC TTGAAACAAA CTTCATACTA CAGTCCTCTT TCATGAAGCA GAAGAGGGCA   240
GTGGGCAGAG CTCTCCTTTG GCTTTCTCCC CCACCACAAC AGGGAGCCCT GGAGCTCTAG   300
GAGAGAAAAT CTGAAATATA AAGGGCATGC ATGTGAGCTG TGGAGTCCCA GAGCCCTGGG   360
TTTGCATCCT AGATCTGCAA CTCCCGTGAA TTGAGTTTTG GGAAGTTGCT GAAACTCTGA   420
CCTCCTGTTT TCTCATGGTA TTGTTGTAAG GGTTAAATGA GACAATGTAT GTGAAGACCC   480
TGGCCCCACA GTAGAGGCTC TGCACACATT TCAGCGATAC TTTCCTCATG TATTTCCAAA   540
AATGTTTTCT CATTTTCTTA AAATGTCAGA AAGAAGACAA CAGAACTTAC TTGCCTTTTA   600
CAACAGAACA AATGGAGCAA GTCAGAGGTC AAGGTGCTAA CATTCTTCAT GGTTCCTCAC   660
CACCTTTTGT TCTGTTAGCC TATAGGGAAA AGTCTTCTTT CTCATCTCAT TATCTGCAGG   720
GGAAAATAGT ACTTCAGCAA GTGATCCAGT TGAAGAACAT CTCCAGGGCC ATTAACATAC   780
AGAGGTTTGT TCTACTCTCT CTGTGCTCCA TGTCTAAGAA CCTCAGCCTT CCTCCTAGGA   840
GCTAGGGAAA GTCAGGAAAG TGAAAATAGT ACCCCAGCTA ATGAACTGCC CTGTGCTGGC   900
CTGAGAAGAC AAGACCAGCT TCCTCAATGG CTCAAGATTT GGTTTCCTTC AATATGTCCT   960
TTTGGAAATA TGTCCATGAC ATCGGAGAGA TAAAGGAGC CAGGATTGCT CACATTCAGG   1020
AAAAAGCTC CACTATCTTT CTCTCTCTCC CTCTTTCTCT CCCTCCCCCT GACTGCCCTC   1080
TTCTCTATCT CTCTCTCTCC CTGAGCTGGC AAGGTTAATT GGTCGCAGAA AGCCGAAGAA   1140
ACAAGTGGGC CTCCTGGAAC AAAGTTCAAA AAGCCGAAAA CGGGAAGAAA ACTAACCACA   1200
AAAGTAAAGG AACCACTTAG CCTTCTTTGA TTCCAGGCCC CCAAGCCTGT CTTTAACTTG   1260
GATGAATGGA GTTCTTCCTG TGCTACAGCA CCGCATAGTA GGGGCTGCCC TGGGCCTGAA   1320
GCCAGAGCTT CACCATATTC AGTCATCTGT ACATTGAGGC AACAGTGCCT GCTTCATGGT   1380
GCTACCCTGT GGATTAAATG AAGCAAGTTT TTGATGATCT TGACACTGAA TATTGATGCA   1440
TTGGTCAGAC TTTTTCTGAT AGTAAAAAAT GGTGGTTTCT TGTTGTCAGA AATCAAATCA   1500
ATATATTTGT TCTCCTGTTG ATTAGCTATG TCCCTAGAG GGCAGCGACT TTGCCTGTCT   1560
TATTTATCTC TGCATCTCCA GCACTTAAAA GGTGCCTTGC ATAAGGTACA TATTAAGTTC   1620
ATATGAATGA ATGAATGAAA TGCATATGAT TTATTCATAC CCAGTTGGTG GTGTGTTTAC   1680
CCTTTCCTAA ACCTGTAGTC AGATGGCCTT TGAATCCCCT GTACTTCTTG TGAGGTACTG   1740
TGCTGTAAAG GTGGACTATC ACACTTCAGT TCAGAGCAAT CTGGGCTTGA ATCCTGGATT   1800
TGCCAGTTTA TTAACTATAG CAAACATTTT TGAGCATACA TTGTGCCAAG TGCTAGGCTA   1860
ACTGTCTTAC ACACATTGTC TTATTTCGTC TTAATATCTA TGAGTCATGC ACTATAATCA   1920
```

-continued

| | | | | | |
|---|---|---|---|---|---|
| TCCCCATTTT | ACAGATAAGA | AAGCAAAGAC | TTGGAGAGGA | AAAGCATCTT | GTTCAAAGGT | 1980 |
| AAATACTTAA | TGGCCAAGCC | AACATGCAAA | TCTAGATTTA | ATTGCAGCTT | CCTCTTCATC | 2040 |
| TACCATTCGA | ACTAATTCAA | GCTATGTAAT | ATTTCCCACT | GAACCTTCTT | GCCTCTACTT | 2100 |
| CCTCATCTTT | AACATGGTCA | AAATACCTGT | CCTGCCCAAG | TTAGTTATTT | CATTAAAGTA | 2160 |
| GAAAATACA | AGAGAAGCTT | TTAAAATGTG | AAACCTCAAA | TGAATGTAAA | ATTATGATGA | 2220 |
| TTCCTTTAGA | ATTTGTCAAC | ACCTTCTTTT | CTCTACTCCT | GCTAGGCATT | TACAATCTCA | 2280 |
| AAACCATGTA | TTTAAGATGC | AAAACTATAT | TTGTATTTGC | CATAACTGGT | TTCTTTCCCT | 2340 |
| ATGGCTTCAT | GAAAATGTGG | CTCGAATGTG | TTTATTATGA | AAGCCCCAAA | TTAATCACGA | 2400 |
| CAAGACTTCA | CCAGCCCATT | CCACAATAGA | CTCCCATTAC | TTTGCCCTGA | CTTAGAAACC | 2460 |
| TCATATACAG | TCTTGATTCA | GTACAGCTCT | GTGATGCTCT | TGGAAAATGC | AAAGTGCTTT | 2520 |
| CTTAATTGAG | GCAATCTGTG | TCCCACTACA | GAGAGGTGGT | TTAACTTGTG | AATTC | 2575 |

( 2 ) INFORMATION FOR SEQ ID NO:34:

( i ) SEQUENCE CHARACTERISTICS:
        ( A ) LENGTH: 2316 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

| | | | | | |
|---|---|---|---|---|---|
| AGAGCAACCT | GGGCAACATA | GCAAACCCT | GTCTCTGCAA | ACAATAAAAA | GAAGAAAATT | 60 |
| AGCTGGGTAT | GGTGGCACAT | GCTATAGTCG | CAGCTACTCG | AGAGGTTGAG | GTGGGAGGAT | 120 |
| CAGTTCAGCC | TGGGAGGTTG | AGGCTGCAGT | GAGCCAGATC | ATGCCACTGC | ACTGCAGCAT | 180 |
| GGGCAACAGA | ATGAGACCCT | GGCTAAAAGA | AAACAAAATA | AAAAATTCAG | ACACAGGTTG | 240 |
| AATCATTGAT | AACAGCATAG | TGGTAACAGA | AAGAAAGTTT | GGGAAATTTT | TATCTGATCA | 300 |
| GCTTCCCATA | CCCTGTTCAT | CTTTGTGTTA | TGCACTGCCA | GGCTGTCTGT | AGGTTCAGAC | 360 |
| TCTATATCAT | ATGACCTTCA | AACACTTGGT | TTGTTCTTCT | CCTTCCTTCC | TCCCTTCTTC | 420 |
| TTTCATTTTT | TATCTTTTTT | TCTTTTAAAA | TGTTTAGATA | GTATAATAAG | GAACTGCTGA | 480 |
| GGCTTTCCAG | TGCCTCCCTC | AACATCCGGA | CAGCTAAGGA | GGATTTCACT | TTGCACCTTG | 540 |
| AGGACGGTTC | CTACAACATC | CGAAAAGATG | ACATCATAGC | TCTTTACCCA | CAGTTAATGC | 600 |
| ACTTAGATCC | AGAAATCTAC | CCAGACCCTT | TGGTAAAGTC | GCAGTGTGCC | CGAATTGAAA | 660 |
| TTCAATATCC | AGGTGATAGC | TACCTAGATC | TAAATAAAGA | GGAAATTTAC | AATGGTAGAA | 720 |
| TTGATTTTCT | CATAGTAGTC | ACAGGAATTG | TCTGACTTAA | TTGTGTTAAA | TATTCATATA | 780 |
| TTTTGGAAAA | TTTAGATAGT | GGTCTGAATT | TTTCATTTTA | GTCCTGATAT | TTGCCATCAC | 840 |
| ACAGTCTTTG | CTAGATTATA | TTTGCAGTCA | TGATAATAAA | CCTGCCACTT | TTTTTTTCTT | 900 |
| AAAAAGCACC | TCCTCCCAAA | TCCAGGAAAT | TGGAGGCTAA | TATATTGATT | ATTCTAGTTT | 960 |
| CTTCTGGGAA | CCCTTCTCTC | TCTAGCTCTG | CCTGACTAAG | GAACTAATCG | TTCAAGCAGG | 1020 |
| ATAGGAAGGT | ATCACAAGGC | TTCCTTAGCT | GCATTAAGCT | CCTGTTCCTT | ATTACTTTCT | 1080 |
| GATTCAATGT | GGAGTATTTG | CTAAATCACT | AATGGGGTAG | AATTAAAAAG | AAAATTACTC | 1140 |
| TTTGGAGCTT | CCAGGTTTAG | AAAGAGATAA | ATTTCTTTAA | AACTAGCTTA | AAGGCGGTTT | 1200 |
| TCTTTGTATT | TTTATTGCAG | ACTTTTAAAT | ATGATAGGTA | TCTTGATGAA | AACGGGAAGA | 1260 |
| CAAAGACTAC | CTTCTATTGT | AATGGACTCA | AGTTAAAGTA | TTACTACATG | CCCTTTGGAT | 1320 |
| CGGGAGCTAC | AATATGTCCT | GGAAGATTGT | TCGCTATCCA | CGAAATCAAG | CAATTTTTGA | 1380 |

```
TTCTGATGCT TTCTTATTTT GAATTGGAGC TTATAGAGGG CCAAGCTAAA TGTCCACCTT    1440

TGGACCAGTC CCGGGCAGGC TTGGGCATTT TGCCGCCATT GAATGATATT GAATTTAAAT    1500

ATAAATTCAA GCATTTGTGA ATACATGGCT GGAATAAGAG GACACTAGAT ATTACAGGAC    1560

TGCAGAACAC CCTCACCACA CAGTCCCTTT GGACAAATGC ATTTAGTGGT GGCACCACAC    1620

AGTCCCTTTG GACAAATGCA TTTAGTGGTG GTAGAAATGA TTCACCAGGT CCAATGTTGT    1680

TCACCAGTGC TTGCTTGTGA AATCTTAACA TTTGGTGAC AGTTCCAGA TGCTATCACA      1740

GACTCTGCTA GTGAAAAGAA CTAGTTTCTA GGAGCACAAT AATTTGTTTT CATTTGTATA    1800

AGTCCATGAA TGTTCATATA GCCAGGGATT GAAGTTTATT ATTTCAAAG GAAAACACCT     1860

TTATTTTATT TTTTTCAAA ATGAAGATAC ACATTACAGC CAGGTGTGGT AGCAGGCACC     1920

TGTAGTCTTA GCTACTCGAG AGGCCAAAGA AGGAGGATGC TTGAGCCCAG GAGTTCAAGA    1980

CCAGCCTGGA CAGCTTAGTG AGATCCCGTC TCCAAAGAAA AGATATGTAT TCTAATTGGC    2040

AGATTGTTTT TTCCTAAGGA AACTGCTTTA TTTTTATAAA ACTGCCTGAC AATTATGAAA    2100

AAATGTTCAA ATTCACGTTC TAGTGAAACT GCATTATTTG TTGACTAGAT GGTGGGGTTC    2160

TTCGGGTGTG ATCATATATC ATAAAGGATA TTTCAAATGT TATGATTAGT TATGTCTTTT    2220

AATAAAAAGG AAATATTTTT CAACTTCTTC TATATCCAAA ATTCAGGGCT TTAAACATGA    2280

TTATCTTGAT TTCCCAAAAA CACTAAAGGT GGTTTT                              2316
```

( 2 ) INFORMATION FOR SEQ ID NO:35:

( i ) SEQUENCE CHARACTERISTICS:
        ( A ) LENGTH: 10614 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

```
GAATTCTAAA CACATATTAA TATCAATGAC TTATATGTAT GTATATATAT ATCTAATATA      60

GATAATGTAT CTAGGGATAT ATATATATGT ATATTTTATC TTTCTTCCTT TTATTCTTTC     120

TTCTCCCCTC TCTGTTCAAC ACCGAGGAAT AGAATGCACT GTGGTGTCAT ACTCTGCTTA     180

CTCAGCCTCT TATTGACCTC TGAGTCAATA CAGTGCTGAT GTACATCTCC AAATGCCCTC     240

TTTTCTCCTA ACCACAGACT TTTACATTCA GTAATCAATT TGACATTGTC CCATGATTTA     300

CAAATGTTCA CAATAGTATA TTGACCTATT GCTGCCTTCC AAGGTCCTCT CCCACTCCCA     360

AACATCCCAA TATGAACCAG CTTTTGCCTA TCTTCTTGTC TCTTACTTTA ACTCAATGTC     420

ATTCCCTATT CACTTTGCTG TAATAGATGC TACCTTGATT CTGGTTTTTA GCACCTTAAT     480

TTCGCTCTCT GCTCAGGAAC TCTGCCTTTG CTGTTCCCTC TTCTGGGAAC GCTTTTCCTT     540

TGCTGTTATA TCTCTTCAAA ACAGCTTCTC TATTCAATAT GCTCAAGCTG CCTTCAGCCC     600

TCAACAGCTC TCCCTACCTC ATTCTAGTCC CTCCACTAGA ATAGAATCTT CATGAGAGTA     660

GCGAACTTCC CTATCTTGCT AGTACCCAAA GGCAGAAAAA TCTTTAAAGA GTTCCTGGGA     720

CATAGAAAAA GTGCTCAATT AATATTTGTA TTAAATAGGG ACCTCAGGTG TAACTCCGTG     780

GTAGAGCGTT TGCCTTAGAG AAGTAGGGCC ATGGGTTCAA ATTCCAGCAC AGAACAAAAA    840

ATTGTGCTGA ATAAAGTTTG GGAGGATGTG TAGCAGTTTA TAGTGCAAGT GGCATAAGCA    900

GTAAATAATG AATTTGTATC CACTTTTCTA GCAAGAAGTA TTTTATTCTT TATTTGAAGG    960

ATAACAATTG GTAAAGACTG CATTCTCAAA ATAAACTATG GCTTATGGCT ACGTGGAAGA   1020
```

```
TGAGATAGGG AGAAGGTTTT TTTTTGATGA TGGCAAAATA ACATGTCATA GTCCACACGA   1080
AACACCTGTG AAGTTGTAAA CACACCTAGC AATCAAACAA GAAAATTGTC CCACCCTATT   1140
ATCATTCTTT TGGATTGGTT GTGGCATATT TCTGGAAAAT GATTAAATT AATTCCTTCT    1200
AAAGGTAACA ACACAAACAA CCACTATCAT GACGAAAAGC TTCTGCCTGT TTCAGTTTAC   1260
ATCATGCTCA ATGTCTACAA CAGACGTGCT CATCTTCAGA GTGTTTACCT CTGCTTTTA    1320
CACACATTGA AGCACAATGT GAGCTGCTGT CCCTGGGTCT GAATGTTATG TCAGCACACA   1380
AGGGACAGAG CTTCGGCTTA TCAAGTATTG AAGCTCTCTG CTTGTTTTGG AGCCTCTTCT   1440
GATACTATGG ACTTAGTTCA AGGCTGGGCA ATACTATTTT TTTCTTTTTT CTAATAGGAG   1500
GACAAATAGT TAGTTGTTTG CTTTGGTCAT CCAAGTTCAA GTTATTGGAT CATGGTCCTA   1560
TGTGTATAAA GAGTCTAGTT TGAGCCTTTC AGGGGCAGCC TTGCTGGCTA AGCACAGACT   1620
CTCCTCTTGG GAGTTTTCCT GCTTTGCAAA ATGATGACCA TCTCTTTGAT TTGGGGGATT   1680
GCTATGGTAG TGTGCTGTTG TATATGGGTT ATCTTGACA GAAGGAGAAG GTATGTCTTT    1740
TAGCTTATTT CTAGTGTTTT CACTATTATA CAGTTCCAAA AAAATACTAG TACATTAGTA   1800
TTTTTATTTA AAATTTAAAG CCATGCTTCT TTGACTAAAC CTGACAAGAT GTAGAGTTTC   1860
CCTTTGAATA TCCACATACA CTGATGGTAA TGCTGATCTT GTTAAACATA ACTAAAAAAA   1920
TTATAAGTAT TGATGCATGT TTGTGTGCAC TTCTGTGGAG TACACCTAAG CTGGGAAGGG   1980
TGCATTTGGC AAGGGTGACG TTTGGAAAGG ATCTTTCTCT CACAATAACT GGTTATGCAT   2040
ATGCTCTTCT GGGTTCTCTG TTACATCAAC ATTAAAATAC AGGAATACCC TTGGCATATC   2100
TTTGGCAAGG TAGACTGTGT CTGCTGTCTT AGTTTTAATA ACTTCTTTGC CTTTTGAGTT   2160
ATTTGAATTT ATGCCTGATC GTTCCAGTT TTAGTTGTCT TAATGCTAAG AAAGGACAAA    2220
TCAATTATAT TTAGTTATTC TAACAAGAGA TAACTAGTTT ACGTTGAAAA ATAAATTATC   2280
TTATAATTTC TAATAAAAAC ATTAAGAGA GTTAGAAATC AGCGAATTAT AGCTGATGAT    2340
CTGCCAATGT TTACCTCACT CAACTTCATT TTAGATACTT TTTCAAGTGG GATTCCTATT   2400
CTCTTCAAAT ATCCGCACAG AATTATAGTC CCCTTCTTTC AGAGTGGGGG GAATCAAATG   2460
AAAGGTTTCA TGTGTGCTAG GCAAGAGCAC CACCGTTGAG CCACACCTCC AGACCCCACA   2520
ATGCCAACAT TTTTAAACTA TGTAGAGTTT AAAAAACTTT AGTTCTGTAG CCTTTTCTAT   2580
TAGCTGGTGT TTCATGTCTT CAAAGAAAAG GAAAACTGAA ACATTTTAGA CATATGGACA   2640
AATGATTCCT TGAACAAGTC TAAGCACTGA TGATAGCTTC TTTTCTACAG TGAGATCAAG   2700
AATCTTGTTA GCCCTGTTGA TACTTGTAGC CCTGTCACTT GGAAAAGCAA TCAATTTTAT   2760
GATCTAGAAA ATAGAGCTTG CCTAAAGATC AGAGTGCAGA GCTAGTCACA CTAGTCAGCC   2820
ATACAGGTTA GGCAGTGGTG GCACATACCT TTAATCCCTG CAGCCACTCA AGTTACCCAT   2880
AGAAGCTGGG TGGTGGTGGT GCACACCCTT AATATAAGGT GGAGCACACT TTAATGTAAG   2940
GTGGGTAGAG TCAGGAGTGC AGTGTATTCA GTCTGCAGTC ACACTGAGAA CAATATCACC   3000
CCAGTCTTGT TAGAGGTAAG AACTCTCTAG TGATTGGCTG CTTTGCTCTT CTGATCTTCA   3060
GTTTGAACTT CTGTCTCTGG GTTTTATTA TTCGTGCTGC AGACATAGAC ATAGCAAACA    3120
ATTTAATGAG TGATTGATGA ATGTAGATAT GTATGTACAT ATTGTGCTGG ATAGACTGTA   3180
GATGGGTTGG TGGATGGGTT GATGAGTGGG TAGATTTAGT AATCACCTTC ACCAATATCT   3240
TAGTAGGCTA AAAAGCCCAC TGTTTTAGTA AAAGAGTGGG GTATCCAACA AAGAAGTATC   3300
TATAAACTGT AGTTATGTGG TAGAAATAAG GGGTAGAAAC CAGTAAAAAT TCGGCTTATG   3360
TACAAATGCT AAACATGTAA TTTCCTAAAC CTCTCAATCT GTCTCACAGG AAAGCAGGTG   3420
```

```
AACCTCCTTT GGAGAATGGG TTGATTCCAT ACCTGGGCTG TGCTCTGAAA TTTGGCTCTA  3480
ATCCTCTTGA GTTCCTGAGA GCAAATCAAA GAAAGCACGG TCATGTTTTT ACCTGCAAAT  3540
TAATGGGGAA ATATGTTCAC TTCATCACAA ACTCCTTGTC ATACCATAAG GTGTTATGTC  3600
ATGGAAAATA CTTTGATTGG AAAAAATTTC ATTACACTAC TTCTGCAAAG GTAACTAGTT  3660
TTTACAGATT TTGCTTGTTT ACTAGCCTGT TTATTTATTA GTTATTTAG TTGTTCCAAT  3720
GTTATTAGAT TGTAGGATAA AGGGAACATA AAATCAGGAA GTCTCTTGGT ACTAAGCATT  3780
AAAAAGTCAA GGTAAATGTG AATTTGTGAT TGATGATGAC ATACACAAAT TAAGCACTTT  3840
GTAAGTACTT TCTGAGCCAG AAGACACTAC AGGAAGGCAC AGACTCATAA CATCCATGCT  3900
GCCATCTACA CAACACTCAG AGCACTCAAT TACCACATCA TGCACACGAA CTCGTTCGTT  3960
AAGAAGTCGA CAGTATATTT AAGCATCATT CAGATGTTAT CAAGAATCTC TATTCTAGAG  4020
AAAACAACAC TTAGCTGAAT TTTACAAGA AAATATTAGA CATGGTCTCT GTCTTAAGTA  4080
GATTAAAGTC TGGCTAAAGT GCATCTGCAG AGAACAAAAG GTAAAGATAA AATCAATGGC  4140
CCATTAGTCC AGAGAAGCTT ACCTGAAAAT CTGGGATTTA AACTTGACCT TAAAGGAAGA  4200
GTATGTCTTA AGTTTGACTT TGAAAAATGT TATGAAATTG TATTGGGAAG GCTAGACAGA  4260
GAAGTATGAT ATACTTTAAT CCATCTTCCA GCCATTTCCT AACACCCAGG TTTAGCTGCT  4320
CCCCCTCTGA CGAATTTCAT TTTCTACCAG GCATTTGGAC ACAGAAGCAT TGACCCAAAT  4380
GATGGAAATA CCACAGAAAA CATAAACAAC ACTTTTACCA AGACCCTCCA GGGAGATGCT  4440
TTGCATTCAC TCTCTGAAGC CATGATGCAA AACCTTCAAT TTGTTCTGAG GCCTCCTGAT  4500
CTTCCTAAAT CAAAGAGTGA TGCCTGGGTC ACCGAAGGGA TGTATGCCTT CTGCTACCGA  4560
GTGATGTTTG AAGCTGGATA TCTAACTCTG TTTGGCAGGG ATACTTCAAA GCCAGACACA  4620
CAAAGAGTGC TTATCCTGAA CAACCTTAAC AGCTTCAAGC AATTTGATCA AGTCTTTCCG  4680
GCGTTGGTGG CAGGCCTCCC TATTCACTTG TTCAAGGCGG CACATAAGGC CCGGGAACAG  4740
CTGGCTGAGG GCTTGAAGCA TGAGAACCTC TCTGTGAGGG ACCAGGTCTC GGAACTGATA  4800
CGTCTACGCA TGTTTCTCAA TGACACTCTC TCTACCTTTG ATGACATGGA GAAGGCCAAG  4860
ACACACCTCG CTATCCTCTG GGCCTCTCAG GCAAACACTA TTCCTGCAAC CTTCTGGAGC  4920
TTATTTCAAA TGATCAGGTG GATAGCAATT TGAGTGTTTA TTCTTCATAG TGACAGAAAT  4980
TAACAATTTT TAATAAACCC CCCAAAAGAC TAGCAGAGCT TTCTTTGCTG TTGGTCAAGA  5040
ATGTGATACT CAGTGCCTGT GTTTGACATA TATATATAAC AAAAGTAGCA TTTTGTAAGA  5100
ATATAGTCTC ACCAGAAAGG GATGTCCAG AAGCCGCAGA ACTTAGATCT GCTGGCACTT  5160
GTCATTAAAG GTCCCCTTGC CCAGTCTTGC TTTTAACTCC ATAGTGTTCT TCTTAGTGTC  5220
AAGTTAAATC TATGACTGCA GTCTTCATCA CAACTTTAAA TAATGACTGA CTTGTCAATG  5280
TGGTAAGTGC AGAGGCCACA CCTTACTAGT TTGAACATTC CTGTTTTCTG CGGCCTCACA  5340
GATTACAGC AGAGTTGCAA CATCAATTTC ATATTACCTA TGAACTACAA CCATATTTTA  5400
AGTTCAACAA CTACTTGTTA GTAACATTTC TGAGGCTCAG TTCACTTTAA CCAGATAAAG  5460
GAGATTTCAA ACAGCTGCCA ACAAATTTCC ATGCACTGAA TGGAAGTATT CTTTATCGCA  5520
CAGTTCAAAA ATAATAACAT AAATATTCTG AAGCTGTGGT ATGAATTTAA AGAGTAAATT  5580
TGAATTTCTA CTTGGGAATT CACCAATACC CTGTAATTGT ATGTTAGAGG AAGTATTCGG  5640
AATGAATTAC TCTACTCATC ACACGAATGT CTAGCCCTTA TTAGAATCAT TGGTTTATAG  5700
AGATCTGACC AAAGCTTTGC TTTTACATAG CAACGCCCCT TTAATGCTTC TTCATAAATT  5760
CAAGGACATG AATCCAGTTC AGAATACAGT ACAAGTAAAT GACAATGCCC TTTGCATGTT  5820
```

-continued

| | | | | | |
|---|---|---|---|---|---|
| CCTGGAACCA | CTTCCCTTTT | CATGCTCCCA | TGCTAACGCG | ATCACCTCAT | TAAAAGAAAT | 5880 |
| GGAGTTCTTA | TTTACTTGCA | GCTCTCTGAA | TAAGGCAATA | TCTTCCATAT | GTCTCTTTTC | 5940 |
| ATAGGAGTCC | TGACGCATTG | AGAGCAGCCT | CTGAAGAAGT | GAATGGAGCA | TTACAGAGTG | 6000 |
| CTGGTCAAAA | GCTCAGCTCT | GAAGGGAATG | CAATTTATTT | GGATCAAATA | CAACTGAACA | 6060 |
| ACCTGCCAGT | ACTAGGTGTG | TTCCCTATGC | TATCCCTCAC | TAACATGTCA | CTAGTAACAA | 6120 |
| TGCTCAACAT | ATAATGAATG | TACTATATTC | TTGATATTTT | TGCAACGCTG | CAACAGTCTA | 6180 |
| ATAACTAGGG | TCATCTTCAT | TTTTCTAAC | AAACAAGGAA | CTGAGACCCA | GAGCGTGGGA | 6240 |
| CAGTGGCAAC | CCTGGCATAG | AACATTTGAT | ACTCAGTTGC | TCTAGGTCCT | TGGCCTCCTT | 6300 |
| TCTTAGTCCT | CCAAAACCAC | AAACCCAGGG | TTAAGGAAGC | ATGGAATTAA | TGTGAACAAA | 6360 |
| GCAACACCAT | TGGTTTGGGC | GATGAGACTG | AGGCTTTTCT | TCCTTTGTTT | CTGTATTTTC | 6420 |
| TAGAATGCAG | TAGTACCATG | TATTACAGTA | AAACAGCCAT | ATTTTGTGT | CCTGTTCTGT | 6480 |
| AAAGGACAGA | AGCCCCCATA | TGCTTTGAGG | GCAGTTTAGT | TTATTAGAAG | CAACAGAGCC | 6540 |
| TAGATTCAGC | ACTGCCTGGT | TTGGGACCTC | CCTTTAGACA | CCTCCCTTTT | CTCACCTGTA | 6600 |
| AATAAAGGCT | AAGTAAGCAT | TTGTGACTGC | ATACTCAGTC | ATGGCCTGAA | TCCTGGGAAC | 6660 |
| AAGGCAGCTA | GCAGCTAGAG | GCTGGAAAAC | AGGACTGGAC | CTCAGCAGCT | CTACTGCATT | 6720 |
| ACTTCCCCTA | GAAGCAGGGT | GTGGCTACAC | AAAACCAGAC | AGATAATGTA | TGGCTGAATG | 6780 |
| TAGATTCATG | AAATGCTTGG | AAAGACATTT | ACTTATCAGT | ATGTTTAATT | CCCAAAATGG | 6840 |
| TCAGCAACAA | TTCACACAAA | ATTGATTATA | AGTTTTTCA | ATTGCTTAG | CTGTTAGTG | 6900 |
| TCCAGTAGAA | ATAAGATTAC | TATTCTATAA | AGTGACAGAT | GTTCATCTAG | TTCCCATTGA | 6960 |
| TGGTGAAGAA | CATTATGTCA | TCCCAAAAGA | TCGTTAACTT | AGATCGTGGT | TCTCTACCTT | 7020 |
| CCTGATGTTG | TGTGACCCCC | AACTGTGAAA | TTATTTCAT | TGCTACTTCA | CAACTATAAT | 7080 |
| TTTGCTTCTG | TCATGAATCA | TAAAGCAAAT | ATCTGTGTTT | CTGATGGTC | TTAGGTGACC | 7140 |
| CCTGTGAAAG | GGTCATTTGA | CTCTACCCCC | TACATGGGTT | GTGATCCACA | GGTTGAGAAG | 7200 |
| CACTGACTTA | GATTCTCAGA | TTGCAAGTAG | AGCAGCAGAA | TTTCGAAGAA | CAGCAGTGGC | 7260 |
| GACAGAAGCT | GCTTTGGGCA | GTTGTCATTT | GTTAGCTTTC | ATTGGCTCAT | TTGTATACA | 7320 |
| GATTTTCGGA | AGTATTTCAG | ACTTTATGTT | ATGTAGCCTT | TAGAGGCAAC | AGTTCAGGAC | 7380 |
| TGGAGAGATG | GCTCAAGGGT | TAAGAGCACT | GGCTGTTTTT | TCAGAGGACC | CATGTTTGAC | 7440 |
| TCACAGCACA | CACATGGTGG | CTCACAGCCA | TCATGACTCC | TGTTCCAAAG | GATCTGATGT | 7500 |
| CTTCTTCTGA | CCTCTGCAGA | CACCAGGCAT | GCATACATGC | AGGCAAAATA | CCCATCAATA | 7560 |
| TAAAAATAAA | TAACTGGGAA | ATATGCAAAT | TCTTTAATAT | GCAAATTCTT | CTCTCCCCAA | 7620 |
| CTGCCATTTC | CCATGCTCCA | CCCTCATCCC | TTCCCTCCTC | TCTTACTTCT | TTGTTTGGA | 7680 |
| ATTCTTTAGA | TAGCATCATC | AAGGAGGCTC | TGAGGCTTTC | CAGTGCATCC | TTGAATATCC | 7740 |
| GGACTGCTAA | GGAGGATTTC | ACTCTGCACC | TTGAGGATGG | CTCCTATAAC | ATCCGAAAAG | 7800 |
| ACGACATCAT | CGCTCTTTAT | CCACAGTTAA | TGCATTTGGA | TCCTGCAATC | TACCCAGACC | 7860 |
| CTCTGGTAAG | TTTTTCTGCT | CATCAAAGTT | ATGTATCGAG | GTGACAGTCA | CCCAGGAATG | 7920 |
| TATTTGTAAT | TACAGCTTTG | ATTTGATCAT | TAAAGTGAAG | CCATAGGGAT | TGTCCCTCTT | 7980 |
| TATTGCGGCA | AATATTCATG | TTTTGGAAAC | TTTGGGTAGA | GGCAAGAGTT | TTGAACTTTT | 8040 |
| ACACCTAATA | TTCATTTCAT | AGTTTCTGCT | AGACTATGTT | TTCAGTCATA | ACAAAACTAC | 8100 |
| CACCTTTTTT | CCCCCTCACA | AAGTACCCTC | TCCCAAATTT | ACACTAATGG | AGGGTAATGC | 8160 |
| ATTTGACTTG | ATCCTTAGAG | TAGTTGTTTA | GAGCCATTTT | GCTTCTTTTG | TCTAACTGAA | 8220 |

| | | | | | |
|---|---|---|---|---|---|
| GAATTAGTCT | ACAGGTAGAA | CAGGAGGTCC | CTAGAGCTTC | TTGGTCCACC | AGCTCTTCAT | 8280 |
| AAGCTCTTTC | CAGTATCACC | TGGTTCAGTG | CTTGGTGTTT | GCTAACTTGT | AGAGGATGGA | 8340 |
| TTTATTAGTA | GAAAATTACT | CTTTGGATCC | TCCAGGTCAA | GAAGGCAACA | ACTTTCTATC | 8400 |
| ATAATAGCTC | ATTGGCTTCT | TGTCTCTTTG | TTGCAGACTT | TAAATATGA | TCGATACCTG | 8460 |
| GATGAGAACA | AGAAGGCAAA | GACCTCCTTC | TATAGCAATG | GAAACAAACT | AAAGTATTTC | 8520 |
| TATATGCCAT | TTGGATCCGG | AGCTACAATA | TGCCCTGGGA | GACTATTTGC | TGTCCAAGAA | 8580 |
| ATCAAGCAAT | TTTTGATTCT | GATGCTTTCA | TACTTTGAAC | TGGAGCTTGT | GGAGAGTCAT | 8640 |
| GTCAAGTGTC | CTCCTCTAGA | CCAGTCCAGG | GCAGGCTTGG | GGATTTTGCC | ACCATTAAAT | 8700 |
| GATATTGAGT | TTAAATATAA | ACTGAAACAT | CTGTGACATG | TGGTTGGAAG | AAGAGGACAC | 8760 |
| TGGATGATGT | TGCTGGACTG | CAGCGAGTCT | CACTAAACAA | GCCCTTGGGA | CAAATGCTCT | 8820 |
| CCTTTGCTTC | CCAGCAACTG | ACTGTGCCTA | GGAAAAGAAC | TGGTACCCCC | GGCACCACTC | 8880 |
| TCTGTTCTCA | CTGCCTGAGT | TCCTGGGTGT | TCAGATAGCT | GAGGTCAGAG | TTTCACCACT | 8940 |
| CTTAGAAGCA | ATGTCTTTTG | TTTTTATTTT | CAAAATGAAG | ATACTCCAAT | TGGCAGATTT | 9000 |
| TTTTTCCTAA | GGAAATTGCT | TCATACTTTT | ATGAAAACTG | ATTAATTATG | AAAAGGCTTC | 9060 |
| AAATTCACGT | TTAGTGAAA | CTGTTATTTT | TTTCACTAGT | GAAGTTCTTC | ATGTGTGAAC | 9120 |
| ATATACTATA | AAAACATTTT | AAGGGATCAT | ATCATGCTTT | GCATAAAGGG | AAAGGAAAAT | 9180 |
| ATTATTCAAC | TTTTTTTTTT | GGTTTTTCTA | GACAGGGTTT | CTCTGTGTAG | CTTTGGAGCC | 9240 |
| TATCCTGGCA | CTCACTCTGT | AGAGCAGGCT | TGGTCTTGAA | CTCACAGAGA | TCTGCCTGCC | 9300 |
| TTTGCCTTCC | GAGTGCTGGG | ATTAAAGTCG | TGCGTCACCA | ATGCCTGGCT | ATTTAACTTT | 9360 |
| TTCGATGTCT | AGTGGTGAGA | GCTTTGAAAA | TGATGCTACT | GTGTTGGGAA | TACTATGGGA | 9420 |
| AATTTGATG | CTTCGCTGTT | ACATTTAAAT | TTATTGCTGC | TGGAAATTGT | CACCCCAGTT | 9480 |
| TTCAATTGCC | CCTCTCTCTC | CCTTTTAATA | TTCACACTGA | TGAGCAGAGT | TTTTTAGAGA | 9540 |
| TTAAAAAGAC | CTCCCCAGAG | CCCTGTCTCT | GATGTTTTA | AGCCTTTAAT | CTCAGTACTC | 9600 |
| AGGAGGCAGA | GGCAGGCAGA | GCTCTGTGAG | TTCGAGGCCA | GCCTGATCTA | CAGATCGAGT | 9660 |
| TCCAGGCAAG | CCGGGGCTAC | AGAATGAGAC | CTTGTCACTA | AAAGAAATAA | ATAAGGTCAA | 9720 |
| TTTTATGTCA | CAACTGATTA | TGAATCATTG | TAAAGGATAA | ATTGAAAAAA | AAGAACTCCA | 9780 |
| CGGGAATGAC | CATTTAAATG | GTCTATTTTA | GCTAAAATTA | ACTATGAATT | ATGTGGAGTT | 9840 |
| CATTAAGTGT | ATGTTGACGT | TATATGTTCC | TTTAAAATGT | CTTATGTTTT | ATCTCTGAAT | 9900 |
| GTCTTGTAGA | TGGAGAGCAA | TAATAGTGTT | TAAATACTGA | GTCAATAAGG | TTTTATCTAT | 9960 |
| GTACTTTAAG | AGCATTATTA | GCTGTGTCAT | TTTACTGAT | ATATCTAATA | TATTTATATG | 10020 |
| TAAATTATAT | TTATCTTTTA | TCTTATACTA | CAAATATAAG | TAAATATTTT | AAAACCAGTA | 10080 |
| ACTTTAAAAT | TACCTACCTT | TCAGAAATGA | AATAAGAAC | ATTTGTGCTT | TAACCTTTGA | 10140 |
| AATAGAATGT | TTATTCATCC | ACTGATAAGT | TAAAATAATT | TTATCTGATT | TGTTCAAGA | 10200 |
| AACTCAAAAA | TATTCAAAGT | AATCATGCAC | TCAAGGTCT | TCGTAAGGTT | ACAGAAAATT | 10260 |
| CAATAAAATC | TTTTTTGTGT | AGGGACTGAG | TCAGGGTCTA | GAAGATGCTT | GGCAGGTACT | 10320 |
| CCAGTAGTGA | GCTGGATCCA | GAAGATTCCT | TAAACTTTAA | AATCTTAACA | CTAAGTATTA | 10380 |
| TCACAGAGTT | ATTACCTAAG | TAGAATATTT | TTCCTTTCCT | TTTCAATTGA | CAGAGTCCCA | 10440 |
| CAGCAACACA | GCTGGCTGTA | ACTCTTCACA | TAGCTTGCGC | AGGCTTTGAA | CTCACTGTAC | 10500 |
| TCCTGCCTTT | CCTTTTCTAG | GAAATTATTT | TCCACATCAA | GAAAATTTAA | TTGTTCCGAT | 10560 |
| GAGGTATAGA | GTAACAAATT | TCTGTTATAT | ATTCATCTGT | ATTAAACTGA | ATTC | 10614 |

(2) INFORMATION FOR SEQ ID NO:36:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

TCAAGTTCAA GT        12

(2) INFORMATION FOR SEQ ID NO:37:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CCAAGCTCAA GT        12